(12) United States Patent
Nielsen et al.

(10) Patent No.: US 7,423,181 B2
(45) Date of Patent: Sep. 9, 2008

(54) AMINOALKOXY-FUNCTIONAL CHALCONES

(75) Inventors: Simon Feldbæk Nielsen, Herlev (DK); Thomas Boesen, Copenhagen Ø (DK); Mogens Larsen, Smørum (DK); Mette Bjerg Nielsen, Roskilde (DK); Hasse Kromann, Copenhagen V (DK)

(73) Assignee: Lica Pharmaceuticals A/S, Copenhagen O (DK)

( * ) Notice: Subject to any disclaimer, the term of this patent is extended or adjusted under 35 U.S.C. 154(b) by 177 days.

(21) Appl. No.: 10/514,829

(22) PCT Filed: May 19, 2003

(86) PCT No.: PCT/DK03/00332

§ 371 (c)(1),
(2), (4) Date: May 24, 2005

(87) PCT Pub. No.: WO03/097574

PCT Pub. Date: Nov. 27, 2003

(65) Prior Publication Data

US 2005/0227990 A1 Oct. 13, 2005

(30) Foreign Application Priority Data

May 17, 2002 (DK) .............................. 2002 00762
May 17, 2002 (DK) .............................. 2002 00763
Jul. 18, 2002 (DK) .............................. 2002 01114

(51) Int. Cl.
*C07C 217/54* (2006.01)
*A61K 31/135* (2006.01)

(52) U.S. Cl. ....................... 564/354; 564/307; 564/337; 514/651

(58) Field of Classification Search ........................ None
See application file for complete search history.

(56) References Cited

FOREIGN PATENT DOCUMENTS

WO 93/17671 9/1993
WO 99/00114 1/1999

OTHER PUBLICATIONS

Database CAPLUS on STN, Acc. No. 1992:629356, Bourguet et al., Biochemical and Biophysical Research Communications (1992), 187(2), p. 711-716 (abstract).*
Bradlerova et al., "Preparation and properties of dialkylaminoethoxyazachacones," Chem. Zvesti 37 (2) 251-262 (1983).
Bradlerova et al., "Preparation and Properties of Heterocycloalkylethoxyazachalcones" Acta Facultatis pharmaceuticae, Tom.XLIV.1990, pp. 85-102.
Abstract of Patent CS218450 to Bradlerova, Alena, Feb. 25, 1983.
Abstract of Patent CS218446 to Bradlerova et al., Feb. 25, 1983.
Doshi et al., "Synthesis and biological evaluation of some novel isoxazoles and cyanopyridnes, a new class of potential anti-tubercular agents," Indian Journal of Chemistry, vol. 38B, Mar. 1999, pp. 348-352.

* cited by examiner

*Primary Examiner*—Brian J Davis
(74) *Attorney, Agent, or Firm*—Hunton & Williams LLP

(57) ABSTRACT

The invention provides novel alkoxyaminochalcone derivatives and analogues thereof. Use of the compounds, or compositions comprising them, as pharmaceutically active agents, in particular against bacterial and parasitic infections, is also disclosed. The invention further relates to a method for detecting inhibitory effects against e.g., bacteria, parasites, fungi, and helminths. The chalcones of the invention carry amino substituents and exhibit enhanced biological effects combined with improved metabolic and physicochemical properties, making the compounds useful as drug substances, in particular as antiparasitic, bacteriostatic, and bacteriocidal agents.

11 Claims, 7 Drawing Sheets

AMINOALKOXY-FUNCTIONAL CHALCONES

CROSS-REFERENCE TO RELATED APPLICATIONS

This application is a national stage of International Application No. PCT/DK/03/00332, filed 19 May 2003, which claimed priority from Denmark Applications PA 2002 00762, filed 17 May 2002, PA 2002 00763, filed 17 May 2002, and PA 2002 01114, filed 18 Jul. 2002. The entire contents of the above-identified International Application and the Denmark Applications are incorporated herein by reference.

FIELD OF THE INVENTION

The present invention relates to a novel class of chalcone derivatives and analogues thereto as well as to use of a class of chalcone derivatives as pharmaceutically, active agents, in particular against bacterial and parasitic infections.

Furthermore, the invention relates to a method of predicting whether a chemical compound has a potential inhibitory effect against an organism such as *Helicobacter pylori* and *Plasmodium falciparum*. The prediction is based on the ability of the chemical compound to act as an inhibitior of the enzyme dihydroorotate dehydrogenase which is involved in the synthesis of pyrimidine in prokaryotic as well as eukaryotic cells such as bacteria; parasites, fungi, helminths and any type of mammalian cells such as human cells.

BACKGROUND OF THE INVENTION

Chalcones, e.g., for use against parasitic infections are known from earlier patent applications assigned to the applicant, e.g. WO 93/17671 and WO 99/00114.

Moderate antibacterial activity has been reported for a limited number of chalcones in earlier publications, e.g. Haraguchi, H. et al *Phytochemistry* 1998, 48, 125-129 and Hatano, T. et al *Chem. Pharm. Bull* (Tokyo) 2000,48, 1286-92.

The bioavailability of several of the known chalcones is low due to the low solubility of the compounds. The compounds do not typically dissolve in the intestine and are therefore not available for absorption.

The spread of antimicrobial resistance determinants particular among nosocomial bacterial pathogens is an increasing problem. Such resistant pathogens include *Staphylococcus aureus* resistant to methicillin and thus to all β-lactam-antibiotics and Enterococci resistant to vancomycin (VRE). Such resistant bacteria pose a significant therapeutic challenge and bacterial strains resistant to all currently available antimicrobials are emerging. Furthermore, bacterial species intrinsically resistant to commonly employed antimicrobials are being recognized as important opportunistic pathogens in the setting of long-term immunocompromized patients. An example of this is *Stenotrophomonas maltophilia* which possesses a β-lactamase rendering the bacteria intrinsically resistant to carbapenems. As cross-resistance within a given class of antibiotics often occurs the development of new classes of antibiotics is a necessity to counter the emerging threat of bacterial resistance.

The resistance of *Plasmodium falciparum* to chloroquine and other antimalarial drugs have created an urgent need for new drugs that are safe and effective for the prophylaxis and treatment of malaria.

Furthermore, the increasing appearance of resistance to first line antileishmanial drugs, e.g. Pentostam or Glucantime, emphasizes the need for new drugs for the treatment of *Leishmania* infections.

Thus, there is a need for chalcone derivatives with improved therapeutic or prophylactic activities against parasites and bacteria.

DESCRIPTION OF THE INVENTION

Figure 1:
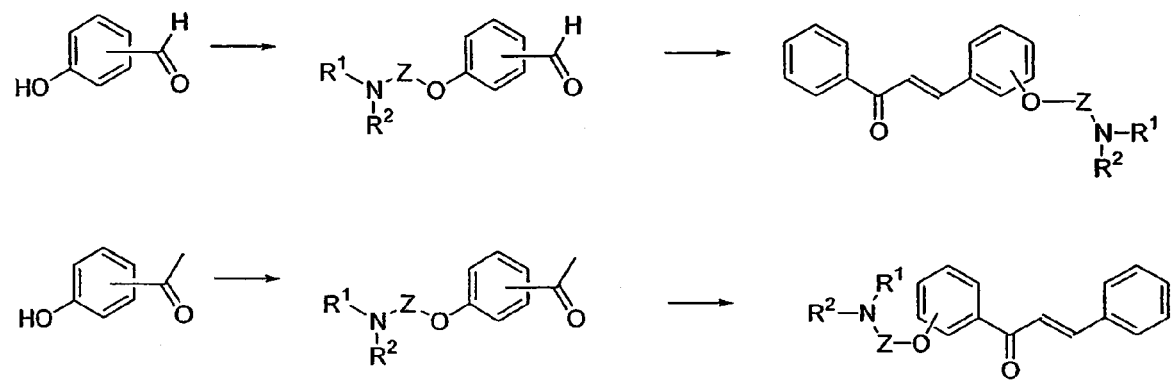
FIG. 1 illustrates the general synthetic scheme for the preparation of aminoalkoxy-functional chalcones where the aromatic rings are phenyl rings. $R^1$, $R^2$ and Z are as defined herein.

In an attempt to identify novel antimicrobial or antiparasitic agents, the present inventors have found that the aminoalkoxy-functional chalcones defined herein exhibit interesting biological properties combined with improved metabolic and physicochemical properties which make the compounds useful as drug substances, in particular as antiparasitic agents, bacteriostatic agents, and bacteriocidal agents.

It is believed that the aminoalkoxy group or groups of the aminoalkoxy-functional chalcone will be charged according to pH of the medium and the pKa of the compound. The aqueous solubility of the charged form is significantly higher than the solubility of the neutral species. As the aminoalkoxy-functional chalcones will be partially charged (i.e. soluble) at physiologically relevant pH values, e. g. in the intestine and stomach, they will dissolve in the gastric juices and be available for absorption. The bioavailability of the aminoalkoxy-functional chalcones will therefore be improved compared to the known neutral chalcones, thus making the compounds generally useful as drug candidates. Also, the present aminoalkoxy-functional chalcones display a range of pKa values which allows the selection of a chalcone derivative with optimal charged/non-charged ratio at a given pH value.

The introduction of an alifatic amino-group and hence a positive charge (at the pH value of the target site) affects the mode of interaction with the biological target. It is anticipated that the compounds interact with the target in a different way than neutral chalcones, due to the possibility of strong electrostatic interactions (attraction as well as repulsion). This is indeed reflected in the activity of the compounds, being more potent than the previously described neutral chalcones.

Furthermore, the application of the known chalcones as drug candidates have been limited due to the extensive metabolism of the compounds resulting in short half-lives in vivo. The inventors have now found that introduction of an aminoalkoxy group in the chalcone molecule changes the metabolic properties so as to achieve improved metabolic stability.

Of particular interest, the present inventors have found that the amino-functional chalcones defined herein are far more potent against malaria and *leishmania* parasites than the earlier described neutral chalcone compounds, and that they exhibit excellent bacteriocidal and bacteriostatic properties, even against multi-resistant bacteria strains.

Thus, in a first aspect, the present invention provides chalcone derivatives and analogues of the general formula:

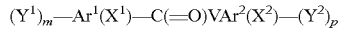

and salts thereof,
wherein $Ar^1$ and $Ar^2$ may independently be selected from aryl or heteroaryl;
V designates —$CH_2$—$CH_2$—, —CH=CH— or —C≡C—, preferably —CH=CH—;
m is 0, 1, or 2,
p is 0, 1, or 2,
wherein the sum of m and p is at least 1;
each $Y^1$ independently may represent an aminoalkoxy-functional substituent of the formula

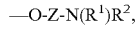

each $Y^2$ independently may represent an aminoalkoxy-functional substituent of the formula

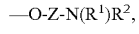

wherein Z is a biradical —$(C(R^H)_2)_n$—, wherein n is an integer in the range of 1-6, preferably 2-4, such as 2-3, and each $R^H$ is independently selected from hydrogen or $C_{1-6}$-alkyl;
$R^1$ and $R^2$ may independently be selected from hydrogen, optionally substituted $C_{1-12}$-alkyl, optionally substituted $C_{2-12}$-alkenyl, optionally substituted $C_{4-12}$-alkadienyl, optionally substituted $C_{6-12}$-alkatrienyl, optionally substituted $C_{2-12}$-alkynyl, optionally substituted $C_{1-12}$-alkoxycarbonyl, optionally substituted $C_{1-12}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl)aminocarbonyl, amino-$C_{1-6}$-alkyl-aminocarbonyl, or mono- and di($C_{1-6}$-alkyl)amino-$C_{1-6}$-alkyl-aminocarbonyl; or $R^1$ and $R^2$ together with the nitrogen atom to which they are attached (—$N(R^1)R^2$) form an optionally substituted nitrogen-containing heterocyclic ring;

$X^1$ may designate 0-5, preferably 0-4, such as 0-3, e.g. 0-2, substituents, and $X^2$ may designate 1-5, preferably 1-4, such as 1-3, e.g. 1-2 substituents, where such substituents independently may be selected from optionally substituted $C_{1-12}$ alkyl, optionally substituted $C_{2-12}$alkenyl, optionally substituted $C_{4-12}$-alkadienyl, optionally substituted $C_{6-12}$-alkatrienyl, optionally substituted $C_{2-12}$alkynyl, hydroxy, optionally substituted $C_{1-12}$-alkoxy, optionally substituted $C_{2-12}$-alkenyloxy, carboxy, optionally substituted $C_{1-12}$-alkoxycarbonyl, optionally substituted $C_{1-12}$-alkylcarbonyl, formyl, $C_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroaryloxycarbonyl, optionally substituted heteroaryloxy, optionally substituted heteroarylcarbonyl, optionally substituted heteroarylamino, heteroarylsulphonylamino, optionally substituted heterocyclyl, optionally substituted heterocyclyloxycarbonyl, optionally substituted heterocyclyloxy, optionally substituted heterocyclylcarbonyl, optionally substituted heterocyclylamino, heterocyclylsulphonylamino, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, amino-$C_{1-6}$-alkyl-amino, mono- and di($C_{1-6}$-alkyl)amino-$C_{1-6}$-alkyl-amino, cyano, guanidino, carbamido, $C_{1-6}$-alkanoyloxy, $C_{1-6}$-alkylsulphonyl, $C_{1-6}$-alkylsulphinyl, $C_{1-6}$-alkylsulphonyloxy, aminosulfonyl, mono- and di($C_{1-6}$-alkyl)aminosulfonyl, nitro, optionally substituted $C_{1-6}$-alkylthio, or halogen, where any nitrogen-bound $C_{1-6}$-alkyl may be substituted with hydroxy, $C_{1-6}$-alkoxy, $C_{2-6}$-alkenyloxy, amino, mono- and di($C_{2-6}$-alkyl)amino, carboxy, $C_{1-6}$-alkylcarbonylamino, halogen, $C_{1-6}$-alkylthio, $C_{1-6}$-alkyl-sulphonyl-amino, or guanidine.

The substituents $R^1$ and $R^2$ carried by the nitrogen atom of the aminoalkoxy substituent, are believed to slightly alter the pKa value of the chalcone derivative. Thus, the particular selection of the groups $R^1$ and $R^2$ may be used to fine-tune the pKa value in view of the particular condition or disease and the intended route of administration.

In one embodiment, $R^1$ and $R^2$ may be independently selected from hydrogen, optionally substituted $C_{1-12}$-alkyl, optionally substituted $C_{2-12}$-alkenyl, optionally substituted $C_{2-12}$-alkynyl, optionally substituted $C_{1-12}$-alkylcarbonyl, arylcarbonyl, heteroarylcarbonyl, aminocarbonyl, mono- and di($C_{1-6}$-alkyl)aminocarbonyl, amino-$C_{1-6}$-alkyl-aminocarbonyl, and mono- and di($C_{1-6}$-alkyl)amino-$C_{1-6}$-alkyl-aminocarbonyl. In particular $R^1$ and $R^2$ are independently selected from hydrogen, optionally substituted $C_{1-6}$-alkyl, optionally substituted $C_{1-6}$-alkylcarbonyl, heteroarylcarbonyl, aminocarbonyl, mono- and di($C_{1-6}$-alkyl)aminocarbonyl, amino-$C_{1-6}$-alkyl-aminocarbonyl, or mono- and di($C_{1-6}$-alkyl)amino-$C_{1-6}$-alkyl-aminocarbonyl.

In another embodiment, $R^1$ and $R^2$ together with the nitrogen atom to which they are attached (—$N(R^1)R^2$) may form an optionally substituted nitrogen-containing heterocyclic ring.

In still a further embodiment, $X^1$ may designate 0-4, such as 0-3, e.g. 0-2, substituents, and $X^2$ may designate 1-4, such as 1-3, e.g. 1-2, substituents, where such optional substituents may independently be selected from optionally substituted $C_{1-12}$-alkyl, hydroxy, optionally substituted. $C_{1-12}$-alkoxy, optionally substituted $C_{2-12}$-alkenyloxy, carboxy, optionally substituted $C_{1-12}$-alkylcarbonyl, formyl, $C_{1-6}$-alkylsulphonylamino, optionally substituted aryl, optionally substituted aryloxycarbonyl, optionally substituted aryloxy, optionally substituted arylcarbonyl, optionally substituted arylamino, arylsulphonylamino, optionally substituted heteroaryl, optionally substituted heteroarylamino, optionally substituted heteroarylcarbonyl, optionally substituted heteroaryloxy, heteroarylsulphonylamino, optionally substituted heterocyclyl, optionally substituted heterocyclyloxy, optionally substituted heterocyclylamino, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, amino-$C_{1-6}$-alkyl-amino, mono- and di($C_{1-6}$-alkyl)amino-$C_{1-6}$-alkyl-amino, guanidino, carbamido, $C_{1-6}$-alkylsulphonyl, $C_{1-6}$-alkylsulphinyl, $C_{1-6}$-alkylsulphonyloxy, optionally substituted $C_{1-6}$-alkylthio, aminosulfonyl, mono- and di($C_{1-6}$-alkyl)aminosulfonyl, or halogen, where any nitrogen-bound $C_{1-6}$-alkyl may be substituted with hydroxy, $C_{1-6}$-alkoxy, and/or halogen. In particular, $X^1$ may designate 0-3, e.g. 0-2, substituents, and $X^2$ designates 1-3, e.g. 1-2, substituents, where such optional substituents may independently be selected from optionally substituted $C_{1-6}$-alkyl, hydroxy, optionally substituted $C_{1-6}$-alkoxy, carboxy, optionally substituted $C_{1-6}$-alkylcarbonyl, $C_{1-6}$-alkylsulphonylamino, optionally substituted aryl, optionally substituted aryloxy, optionally substituted arylamino, arylsulphonylamino, optionally substituted heteroaryl, optionally substituted heteroarylamino, heteroarylsulphonylamino, amino, mono- and di($C_{1-6}$-alkyl)amino, carbamoyl, $C_{1-6}$-alkylcarbonylamino, amino-$C_{1-6}$-alkyl-carbonylamino, mono- and di($C_{1-6}$-alkyl)amino-$C_{1-6}$-alkyl-carbonylamino, amino-$C_{1-6}$-alkyl-amino, mono- and di($C_{1-6}$-alkyl)amino-$C_{1-6}$-alkyl-amino, guanidino, carbamido, optionally substituted $C_{1-6}$-alkylthio, optionally substituted heterocyclyl, optionally substituted heterocyclyloxy, optionally substituted heterocyclylamino or halogen, where any nitrogen-bound $C_{1-6}$-alkyl may be substituted with hydroxy, $C_{1-6}$alkoxy, and/or halogen.

The group V is relevant with respect to the spatial orientation of the rings $Ar^1$ and $Ar^2$. Thus, the group V may be —$CH_2$—$CH_2$—, —CH=CH— or —C≡C—. In a currently particularly interesting embodiment V designates —CH=CH—.

In the context of the present invention the expression "chalcone derivative" has been assigned to the compounds of the above formula in that the overall structure namely $Ar^1$—C(=O)—C—C—$Ar^2$ resembles that of the chalcone structure: This being said, $Ar^1$ and $Ar^2$ are selected from aromatic rings and heteroaromatic rings. It is currently believed that particularly interesting compounds are those where at least one of $Ar^1$ and $Ar^2$, preferably both, are aryl, in particular phenyl. This being said, the inventors envisage that the functionality of the compounds may be substantially preserved (or even improved) when one or both of $Ar^1$ and $Ar^2$ are heteroaromatic rings.

In one embodiment, at least one of $Ar^1$ and $Ar^2$ is selected from thiazolyl, pyrrolyl, imidazolyl, pyrazolyl, pyridinyl, pyrimidinyl, pyrazinyl, pyridazinyl, thienyl, quinolyl, isoquinolyl, and indolyl.

In another embodiment, both of $Ar^1$ and $Ar^2$ are phenyl and $Y^2$ represents at least one aminoalkoxy-functional substituent, one of which being located in the 2-position of the phenyl ring, and $X^2$ represents at least one substituent, one of which being located in the 4- or 5-position of the phenyl ring.

In yet another embodiment, both of $Ar^1$ and $Ar^2$ are phenyl and $Y^2$ represents at least one aminoalkoxy-functional substituent, one of which being located in the 3-position of the phenyl ring, and $X^2$ represents at least one substituent, one of which being located in the 5-position of the phenyl ring.

In a further embodiment, $X^2$ represents at least one substituent selected from $C_{1-6}$-alkyl, hydroxy, $C_{1-6}$-alkoxy, $C_{1-6}$-alkylcarbonyl, optionally substituted aryl, optionally substituted aryloxy, optionally substituted arylamino, optionally substituted heteroaryl, optionally substituted heteroarylamino, mono- and di($C_{1-6}$-alkyl)amino, $C_{1-6}$-alkylcarbonylamino, optionally substituted $C_{1-6}$-alkylthio, optionally substituted heterocyclyl, optionally substituted heterocyclyloxy, optionally substituted heterocyclylamino or halogen, in particular from $C_{1-6}$-alkyl, optionally substituted phenyl, or hydroxy, e.g. from $C_{1-6}$-alkyl or optionally substituted phenyl. Such compounds have shown excellent bacteriostatic and bacteriocidal effects as well as antiparasitic effects (see the Examples).

In a further embodiment, which may combined with other embodiments herein, both of $Ar^1$ and $Ar^2$ are optionally substituted phenyl, and $X^1$ represents at least one substituent, one of which being located in the 2- or 3-position of the phenyl ring, and preferably being selected from amino-$C_{1-6}$-alkyl or mono- and di($C_{1-6}$-alkyl)amino-$C_{1-6}$-alkyl. Such compounds have shown excellent as antiparasitic effects (see the Examples).

In a still further embodiment, which may combined with other embodiments herein, both of $Ar^1$ and $Ar^2$ are phenyl, and $X^1$ represents at least one substituent, one of which being located in the 4-position of the phenyl ring, and preferably being selected from hydroxy, amino-$C_{1-6}$-alkylamino or mono-, and di($C_{1-6}$-alkyl)amino-$C_{1-6}$-alkylamino. Such compounds have also shown excellent as antiparasitic effects (see the Examples).

The group Z is typically a biradical —$(C(R^H)_2)_n$—, wherein n is an integer in the range of 1-6, preferably 2-4, such as 2-3, wherein each $R^H$ may independently be selected from hydrogen or $C_{1-6}$-alkyl. A particular example of Z is —$(CH_2)_n$— wherein n is 2-4, such as 2-3.

Thus, in a particular embodiment, one of $Y^1$ and $Y^2$ represents a substituent of the formula

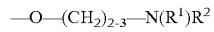

wherein $R^1$ and $R^2$ may be selected from hydrogen or $C_{1-6}$-alkyl. Furthermore, V is preferably —CH=CH—, and $Ar^1$ and $Ar^2$ are both optionally substituted phenyl.

In one preferred embodiment, m is 1 and p is 0. 1in another preferred embodiment m is 0 and p is 1. In a further interesting embodiment, m and p are both 1.

In an additional interesting embodiment, one or both of $X^1$ and $X^2$ independently designates one optionally substituted $C_{1-12}$-alkyl group of the formula

wherein A is a biradical —$(C(R^H)_2)_n$—, wherein n is an integer in the range of 1-6, preferably 1-4, such as 1-3, and each $R^H$ is independently selected from hydrogen or $C_{1-6}$-alkyl, and $R^k$ and $R^m$ may independently be selected from hydrogen, optionally substituted $C_{1-12}$-alkyl, optionally substituted $C_{2-12}$-alkenyl, optionally substituted $C_{4-12}$-alkadienyl, optionally substituted $C_{6-12}$-alkatrienyl, optionally substituted $C_{2-12}$-alkynyl, optionally substituted $C_{1-12}$-alkoxycarbonyl, optionally substituted $C_{1-12}$-alkylcarbonyl, optionally substituted aryl, optionally substituted aryloxycarbonyl, optionally substituted arylcarbonyl, optionally substituted heteroaryl, optionally substituted heteroaryloxycarbonyl, optionally substituted heteroarylcarbonyl, aminocarbonyl, mono- and di($C_{1-6}$-alkyl)aminocarbonyl, amino-$C_{1-6}$-alkyl-aminocarbonyl, or mono- and di($C_{1-6}$-alkyl)amino-$C_{1-6}$-alkyl-aminocarbonyl; or $R^k$ and $R^m$ together with the nitrogen atom to which they are attached (—N($R^k$)$R^m$) may form an optionally substituted nitrogen-containing heterocyclic ring.

In another interesting embodiment, one or both of $X^1$ and $X^2$ independently designates one mono- or di($C_{1-6}$-alkyl)amino-$C_{1-6}$-alkyl-amino group of the formula

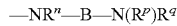

wherein B is a biradical —$(C(R^H)_2)_n$—, wherein n is an integer in the range of 1-6, preferably 2-4, such as 2-3, and each $R^H$ is independently selected from hydrogen or $C_{1-6}$-6alkyl, or two $R^H$ on the same carbon atom may designate =O;

$R^p$ and $R^q$ may independently be selected from hydrogen or optionally substituted $C_{1-6}$-alkyl which may be substituted with hydroxy, $C_{1-6}$-alkoxy, $C_{2-6}$-alkenyloxy amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonylamino, or guanidine;

or $R^p$ and $R^q$ together with the nitrogen atom to which they are attached (—N($R^p$)$R^q$) may form an optionally substituted nitrogen-containing heterocyclic ring;

$R^n$ is selected from hydrogen or $C_{1-6}$-alkyl;

or $R^p$ and $R^n$ may together form a biradical B* which is as defined for B.

In a highly preferred embodiment, the compound of the general formula above may be selected from the group comprising 3-[2-(2-Dimethylamino-ethoxy)-phenyl]1-(2,3,4-trimethoxy-phenyl)-propenone,
3-[2-(2-Dimethylamino-ethoxy)-5-methyl-phenyl]-1-(2-fluoro-4-methoxy-phenyl)-propenone,
3-[2-(2-Dimethylamino-ethoxy)-5-methyl-phenyl]-1-(2,3,4-trimethoxy-phenyl)-propenone,
3-[5-tert-Butyl-2-(2-dimethylamino-ethoxy)-phenyl]-1-(2-fluoro-4-methoxy-phenyl)-propenone,
3-[5-tert-Butyl-2-(2-dimethylamino-ethoxy)-phenyl]-1-(2,3,4-trimethoxy-phenyl)-propenone,
3-[2-(2-Dimethylamino-ethoxy)-5-hydroxy-phenyl]-1-(2,3,4-trimethoxy-phenyl)-propenone,
3-[2-(2-Dimethylamino-ethoxy)-phenyl]-1-(2-fluoro-4-methoxy-phenyl)-propenone,
3-[2-(2-Dimethylamino-ethoxy)-5-methyl-phenyl]-1-(2-dimethylaminomethyl-phenyl)-propenone,
N-(2-{3-[2-(2-Dimethylamino-ethoxy)-5-methyl-phenyl]-acryloyl}-phenyl)-benzenesulfonamide,
3-[4-(2-Dimethylamino-ethoxy)-biphenyl-3-yl]-1-(4-methoxy-phenyl)-propenone,
3-[4-(2-Dimethylamino-ethoxy)-biphenyl-3-yl]-1-(2-fluoro-4-methoxy-phenyl)-propenone,
3-[4-(2-Dimethylamino-ethoxy)-biphenyl-3-yl]-1-(2,3,4-trimethoxy-phenyl)-propenone,
1-(2-Chloro-4-methoxy-phenyl )-3-[4-(2-dimethylamino-ethoxy)-biphenyl-3-yl]-propenone,
3-[4-(2-Dimethylamino-ethoxy)-2'-methoxy-biphenyl-3-yl]-1-(4-methoxy-phenyl)-propenone,
3-[4-(2-Dimethylamino-ethoxy)-2'-methoxy-biphenyl-3-yl]-1-(2-fluoro-4-methoxy-phenyl)-propenone,
3-[4-(2-Dimethylamino-ethoxy)-2'-methoxy-biphenyl-3-yl]-1-(2,3,4-trimethoxy-phenyl)-propenone,
1-(2-Chloro-4-methoxy-phenyl)-3-[4-(2-dimethylamino-ethoxy)-2'-methoxy-biphenyl-3-yl]-propenone,
3-[2'-Chloro-4-(2-dimethylamino-ethoxy)-biphenyl-3-yl]-1-(2,3,4-trimethoxy-phenyl)-propenone,
3-[4-(2-Dimethylamino-ethoxy)-2'-methyl-biphenyl-3-yl]-1-(4-methoxy-phenyl)-propenone,
3-[4-(2-Dimethylamino-ethoxy)-2'-methyl-biphenyl-3-yl]-1-(2-fluoro-4-methoxy-phenyl)-propenone,
3-[4-(2-Dimethylamino-ethoxy)-2'-methyl-biphenyl-3-yl]-1-(2,3,4-trimethoxy-phenyl)-propenone,
1-(2-Chloro-4-methoxy-phenyl)-3-[4-(2-dimethylamino-ethoxy)-2'-methyl-biphenyl-3-yl]-propenone,
3-[4-(2-Dimethylamino-ethoxy)-3',5'-dimethyl-biphenyl-3-yl]-1-(4,-methoxy-phenyl)-propenone,
3-[4-(2-Dimethylamino-ethoxy)-3',5'-dimethyl-biphenyl-3-yl]-1-(2-fluoro-4-methoxy-phenyl)-propenone,
3-[4-(2-Dimethylamino-ethoxy)-3',5'-dimethyl-biphenyl-3-yl]-1-(2,3,4-trimethoxy-phenyl)-propenone,
1(2-Chloro-4-methoxy-phenyl)-3-[4-(2-dimethylamino-ethoxy)-3',5'-dimethyl-biphenyl-3-yl]-propenone,
N-(2-{3-[5-tert-Butyl-2-(2-dimethylamino-ethoxy)-phenyl]-acryloyl}-phenyl)-benzenesulfonamide,
3-[3,5-Di-tert-butyl-2-(2-dimethylamino-ethoxy)-phenyl]-1-(2-fluoro-4-methoxy-phenyl)-propenone,
3-[4-(2-Dimethylamino-ethoxy)-[1,1';4',1"]terphenyl-3-yl]-1-(2-fluoro-4-methoxy-phenyl)-propenone,
1-(2-Diethylaminomethyl-phenyl)-3-[4-(2-dimethylamino-ethoxy)-3',5'-dimethyl-biphenyl-3-yl]-propenone,
3-[4-(2-Dimethylamino-ethoxy)-2'-methoxy-biphenyl-3-yl]-l1-[2-(4-methyl-piperazin-1ylmethyl)-phenyl]-propenone,
3-[4-(2-Dimethylamino-ethoxy)-2'-methyl-biphenyl-3-yl]-1-[2-(4-methyl-piperazin-1-ylmethyl)-phenyl]-propenone,
3-[2-(2-Dimethylamino-ethoxy)-5-methyl-phenyl]-1-[2-(2-dimethylamino-ethoxy)-phenyl]-propenone,
3-[4-(2-Dimethylamino-ethoxy)-biphenyl-3-yl]-1-[4-(2-dimethylamino-ethylamino)-phenyl]-propenone,
3-[4-(2-Dimethylamino-ethoxy)-2'-methyl-biphenyl-3-yl]-1-(2-dimethylaminomethyl-phenyl)-propenone,
3-[4-(2-Dimethylamino-ethoxy)-2'-methoxy-biphenyl-3-yl]-1(2-dimethylaminomethyl-phenyl)-propenone,
3-[4-(2-Dimethylamino-ethoxy)-biphenyl-3-yl]-1-(3-dimethylaminomethyl-phenyl)-propenone,
3-[5-tert-Butyl-2-(2-dimethylamino-ethoxy)-phenyl]-1-(2-diethylaminomethyl-phenyl)-propenone,
3-[2-(2-Dimethylamino-ethoxy)-4-hydroxy-5-propyl-phenyl]-1-(2-fluoro-4-methoxy-phenyl)-propenone,
3-[4-(2-Dimethylamino-ethoxy)-biphenyl-3-yl]-1-(4-hydroxy-phenyl)-propenone,
3-[5-tert-Butyl-2-(2-dimethylamino-ethoxy)-phenyl]-1-(4-hydroxy-phenyl)-propenone,
N-(2-{3-[5-tert-Butyl-2-(3-dimethylamino-propoxy)-phenyl]-acryloyl}-phenyl)-benzenesulfonamide,
3-[3-(2-Dimethylamino-ethoxy)-phenyl]-1-(2,3,4-trimethoxy-phenyl)-propenone,
3-[3-(2-Dimethylamino-ethoxy)-phenyl]-1-(2-fluoro-4-methoxy-phenyl)-propenone,
1-(2,4-Dimethoxy-phenyl)-3-[3-(2-dimethylamino-ethoxy)-phenyl]-propenone,
1-(2,5-Dimethoxy-phenyl)-3-[3-(2-dimethylamino-ethoxy)-phenyl]-propenone,
3-[3-(2-Dimethylamino-ethoxy)-phenyl]-1-(2-methoxy-phenyl)-propenone, 3-[3-(2-Dimethylamino-ethoxy)-phenyl]-1-(4-methoxy-phenyl)-propenone,
3-[3-(2-Dimethylamino-ethoxy)-phenyl]-1-[2-(2-dimethylamino-ethoxy)-phenyl]-propenone,
3-[3-(3-Dimethylamino-propoxy)-phenyl]-1-(2-fluoro-4-methoxy-phenyl)-propenone,
1-(2,4-Dimethoxy-phenyl)-3-[3-(3-dimethylamino-propoxy)-phenyl]-propenone,
3-[3-(3-Dimethylamino-propoxy)-phenyl]-1-(2-methoxy-phenyl)-propenone,
1-(2,5-Dimethoxy-phenyl)-3-[3-(3-dimethylamino-propoxy)-phenyl]-propenone,
3-[3-(3-Dimethylamino-propoxy)-phenyl]-1-(2,3,4-trimethoxy-phenyl)-propenone,
1-(3-Dimethylaminomethyl-phenyl)-3-[3-(3-dimethylamino-propoxy)-phenyl]-propenone,
3-[4-(2-Dimethylamino-ethoxy)-phenyl]-1-(2,3,4-trimethoxy-phenyl)-propenone,
3-(2,5-Dimethoxy-phenyl)-1-[2-(2-dimethylamino-ethoxy)-phenyl]-propenone,
1-[2-(2-Dimethylamino-ethoxy)-phenyl]-3-(3-dimethylaminomethyl-phenyl)-propenone,
1-[2-(2-Dimethylamino-ethoxy)-phenyl]-3-(2-dimethylaminomethyl-phenyl)-propenone,
3-(2,4-Dichloro-phenyl)-1-[2-(2-dimethylamino-ethoxy)-phenyl]-propenone,
3-(2,5-Dimethoxy-phenyl)-1-[2-(3-dimethylamino-propoxy)-phenyl]-propenone,
3-(2,4-Dichloro-phenyl)-1-[2-(3-dimethylamino-propoxy)-phenyl]-propenone,
3-(2,5-Dimethoxy-phenyl)-1-[3-(2-dimethylamino-ethoxy)-phenyl]-propenone,
3-(2,5-Dimethoxy-phenyl)-1-[4-(2-dimethylamino-ethoxy)-phenyl]-propenone,
3-[4-(2-Dimethylamino-ethoxy)-3',5'-dimethyl-biphenyl-3-yl]-1-(2-ethoxy-phenyl)-propenone,
3-[4-(2-Dimethylamino-ethoxy)2'-methyl-biphenyl-3-yl]-1-(2-ethoxy-phenyl)-propenone,
3-[4-(2-Dimethylamino-ethoxy)-3',5'-dimethyl-biphenyl-3-yl]-1-(2-isopropoxy-phenyl)-propenone,
3-[4-(2-Dimethylamino-ethoxy)-2'-methyl-biphenyl-3-yl]-1-[2-(2-hydroxy-ethylamino)-phenyl]-propenone,
3-[4-(2-Dimethylamino-ethoxy)-3',5'-dimethyl-biphenyl-3-yl]-1-[2-(2-hydroxy-ethylamino)-phenyl]-propenone,
3-[3-(2-Dimethylamino-ethoxy)-phenyl]-1-(2-dimethylaminomethyl-phenyl)-propenone,
1-(2-Dimethylaminomethyl-phenyl)-3-[3-(3-dimethylamino-propoxy)-phenyl]-propenone,
3-[4-(2-Dimethylamino-ethoxy)-3',5'-dimethyl-biphenyl-3-yl]-1-(4-fluoro-phenyl)-propan-1-one,
3-[4-(2-Dimethylamino-ethoxy)-2'-methyl-biphenyl-3-yl]-1-(2-dimethylaminomethyl-phenyl)-propan-1-one,
3-[4-(2-Dimethylamino-ethoxy)-3',5'-dimethyl-biphenyl-3-yl]-1-[2-(2-dimethylamino-ethylamino)-phenyl]-propenone,
3-[4-(2-Dimethylamino-ethoxy)-3',5'-dimethyl-biphenyl-3-yl]-1-[3-(2-dimethylamino-ethylamino)-phenyl]-propenone,
3-[4-(2-Dimethylamino-ethoxy)-3',5'-dimethyl-biphenyl-3-yl]-1-{2-[(2-dimethylamino-ethyl)-methyl-amino]-phenyl}-propenone,
1-(2-Butoxy-phenyl)-3-[4-(2-dimethylamino-ethoxy)-3',5'-dimethyl-biphenyl-3-yl]-propenone,
3-[4-(2-Dimethylamino-ethoxy)-3',5'-dimethyl-biphenyl-3-yl]-1-(2-fluoro-phenyl)-propenone,
3-[4-(2-Dimethylamino-ethoxy)-3',5'-dimethyl-biphenyl-3-yl]-1-(3-fluoro-phenyl)-propenone,
1-(2-Bromo-phenyl)-3-[4-(2-dimethylamino-ethoxy)-3',5'-dimethyl-biphenyl-3-yl]-propenone,
1-(3-Bromo-phenyl)-3-[4-(2-dimethylamino-ethoxy)-3',5'-dimethyl-biphenyl-3-yl]-propenone,
1-(4-Bromo-phenyl)-3-[4-(2-dimethylamino-ethoxy)-3',5'-dimethyl-biphenyl-3-yl]-propenone,
3-[4-(2-Dimethylamino-ethoxy)-3',5'-dimethyl-biphenyl-3-yl]-1-(2-hydroxy-phenyl)-propenone,
3-[4-(2-Dimethylamino-ethoxy)-3',5'-dimethyl-biphenyl-3-yl]-1-(3-hydroxy-phenyl)-propenone,
3-[4-(2-Dimethylamino-ethoxy)-3',5'-dimethyl-biphenyl-3-yl]-1-(4-hydroxy-phenyl)-propenone,
1-(4-Cyclohexyl-phenyl)-3-[4-(2-dimethylamino-ethoxy)-3',5'-dimethyl-biphenyl-3-yl]-propenone,
N-(3-{3-[4-(2-Dimethylamino-ethoxy)-3',5'-dimethyl-biphenyl-3-yl]-acryloyl}-phenyl)-acetamide,
3-[4-(2-Dimethylamino-ethoxy)-3',5'-dimethyl-biphenyl-3-yl]-1-(3-dimethylaminomethyl-phenyl)-propenone,
3-[4-(2-Dimethylamino-ethoxy)-3',5'-dimethyl-biphenyl-3-yl]-1-(3-dimethylaminomethyl-4-methoxy-phenyl)-propenone,
3-[4-(2-Dimethylamino-ethoxy)-3',5'-dimethyl-biphenyl-3-yl]-1-(2-dimethylaminomethyl-phenyl)-propenone,
3-[4-(2-Dimethylamino-ethoxy)-3',5'-dimethyl-biphenyl-3-yl]-1-(2-dimethylaminomethyl-4-methoxy-phenyl)-propenone,
1-(2-Amino-phenyl)-3-[4-(2-dimethylamino-ethoxy)-3',5'-dimethyl-biphenyl-3-yl]-propenone,
1-(4-Amino-phenyl)-3-[4-(2-dimethylamino-ethoxy)-3',5'-dimethyl-biphenyl-3-yl]-propenone,
3-[4-(2-Dimethylamino-ethoxy)-3',5'-dimethyl-biphenyl-3-yl]-1-(3-dimethylaminomethyl-4-hydroxy-phenyl)-propenone,
3-[4-(2-Dimethylamino-ethoxy)-2'-methoxy-biphenyl-3-yl]-1-[4-hydroxy-2-(4-methyl-piperazin-1-yl)-phenyl]-propenone,
3-[2'-Chloro-4-(2-dimethylamino-ethoxy)-biphenyl-3-yl]-1-(4-methoxy-phenyl)-propenone,
3-[2'-Chloro-4-(2-dimethylamino-ethoxy)-biphenyl-3-yl]-1-(2-fluoro-4-methoxy-phenyl)-propenone,
3-[4-(2-Dimethylamino-ethoxy)-3',5'-dimethyl-biphenyl-3-yl]-1-[4-hydroxy-3-(4-methyl-piperazin-1-ylmethyl)-phenyl]-propenone,
3-[4-(2-Dimethylamino-ethoxy)-3',5'-dimethyl-biphenyl-3-yl]-1-[4-(2-dimethylamino-ethylamino)-phenyl]-propenone,
3-[4-(2-Dimethylamino-ethoxy)-3',5'-dimethyl-biphenyl-3-yl]-1-[2-(2-dimethylamino-ethoxy)-phenyl]-propenone,
3-[4-(2-Dimethylamino-ethoxy)-3',5'-dimethyl-biphenyl-3-yl]-1-(3-hexyloxy-phenyl)-propenone,
3-[4-(2-Dimethylamino-ethoxy)-3',5'-dimethyl-biphenyl-3-yl]-1-[3-(4-methyl-piperazin-1-yl)-phenyl]-propenone,
3-[4-(2-Dimethylamino-ethoxy)-3',5'-dimethyl-biphenyl-3-yl]-1-[2-(3-dimethylamino-propoxy)-phenyl]-propenone,
3-[4-(2-Dimethylamino-ethoxy)-3',5'-dimethyl-biphenyl-3-yl]-1-(2-fluoro-4-hydroxy-phenyl)-propenone,
1-(6-Amino-benzo[1,3]dioxol-5-yl)-3-[4-(2-dimethylamino-ethoxy)-3',5'-dimethyl-biphenyl-3-yl]-propenone,
3-[4-(2-Dimethylamino-ethoxy)-3',5'-dimethyl-biphenyl-3-yl]-1-phenyl-propenone,
3-[4-(2-Dimethylamino-ethoxy)-2'-methyl-biphenyl-3-yl]-1-(3-dimethylaminomethyl-4-hydroxy-phenyl)-propenone,
3-[4-(2-Dimethylamino-ethoxy)-2'-methyl-biphenyl-3-yl]-1-(3-dimethylaminomethyl-4-methoxy-phenyl)-propenone, 2-Dimethylamino-N-(3-{3-[4-(2-dimethylamino-ethoxy)-2'-methyl-biphenyl-3-yl]-(E)-acryloyl}-phenyl)-acetamide,
3-[4-(4-Dimethylamino-butoxy)-2'-methyl-biphenyl-3-yl]-1-(2-dimethylaminomethyl-phenyl)-propenone,
3-[2'-Chloro-4-(2-dimethylamino-ethoxy)-biphenyl-3-yl]-1-(2-dimethylaminomethyl-5-methoxy-phenyl)-propenone,
3-[4-(2-Dimethylamino-3ethoxy)-2'-methyl-biphenyl-3-yl]-1-(2-dimethylaminomethyl-5-methoxy-phenyl)-propenone,
3-[4-(2-Dimethylamino-ethoxy)-2-methyl-biphenyl-3-yl]-1-(2-imethylaminomethyl-4-methoxy-phenyl)-propenone,
3-[5-(1,1-Dimethyl-allyl)-2-(2-dimethylamino-ethoxy)-phenyl]-1-[4-(tetrahydro-pyran-2-yloxy)-phenyl]-propenone,
3-[5-(1,1-Dimethyl-allyl)-2-(2-dimethylamino-ethoxy)-phenyl]-1-(4-hydroxy-phenyl)-propenone,
3-[6-(2-Dimethylamino-ethoxy)-2,3,3-trimethyl-2,3-dihydro-benzofuran-5-yl]-1-(2-dimethylaminomethyl-phenyl)-propenone,
3-[4-(2-Dimethylamino-ethoxy)-2'-methyl-biphenyl-3-yl]-1-(2-{[(2-dimethylamino-ethyl)-methyl-amino]-methyl}-phenyl)-propenone,
3-[4-(2-Dimethylamino-ethoxy)-2'-methyl-biphenyl-3-yl]-1-(2-pyrrolidin-1-ylmethyl-phenyl)-propenone,
1-{2-[(tert-Butyl-methyl-amino)-methyl]-phenyl}-3-[4-(2-dimethylamino-ethoxy)-2'-methyl-biphenyl-3-yl]-propenone,
3-[4-(2-Dimethylamino-ethoxy)-2'-trifluoromethoxy-biphenyl-3-yl]-1-(2-dimethylaminomethyl-phenyl)-propenone,
3-[2'-tert-Butoxymethyl-4-(2-dimethylamino-ethoxy)-biphenyl-3-yl]-1-(2-dimethylaminomethyl-phenyl)-propenone,
3-[4-(2-Dimethylamino-ethoxy)-2',5'-dimethoxy-biphenyl-3-yl]-1-(2-dimethylaminomethyl-phenyl)-propenone,
3-[4-(2-Dimethylamino-ethoxy)-2',4'-dimethoxy-biphenyl-3-yl]-1-(2-dimethylaminomethyl-phenyl)-propenone,
3-[4-(2-Dimethylamino-ethoxy)-2',4',6'-trimethyl-biphenyl-3-yl]-1-(2-dimethylaminomethyl-phenyl)-propenone,
3-[4-(2-Dimethylamino-ethoxy)-2'-methoxymethyl-biphenyl-3-yl]-1-(2-dimethylaminomethyl-phenyl)-propenone,
3-[4-(2-Dimethylamino-ethoxy)-2',6'-dimethoxy-biphenyl-3-yl]-1-(2-dimethylaminomethyl-phenyl)-propenone,
3-[2'-Chloro-4-(2-dimethylamino-ethoxy)-biphenyl-3-yl]-1-(2-dimethylaminomethyl-phenyl)-propenone,
3-[4-(2-Dimethylamino-ethoxy)-2'-methylsulfanyl-biphenyl-3-yl]-1-(2-dimethylaminomethyl-phenyl)-propenone,
3-[4-(2-Dimethylamino-ethoxy)-2'-trifluoromethyl-biphenyl-3-yl]-1-(2-dimethylaminomethyl-phenyl)-propenone,
3-[4-(2-Dimethylamino-ethoxy)-2'-hydroxy-biphenyl-3-yl]-1-(2-dimethylaminomethyl-phenyl)-propenone,
3-[4-(2-Dimethylamino-ethoxy)-2'-ethyl-biphenyl-3-yl]-1-(2-dimethylaminomethyl-phenyl)-propenone,
3-[2',6'-Dichloro-4-(2-dimethylamino-ethoxy)-biphenyl-3-yl]-1-(2-dimethylaminomethyl-phenyl)-propenone,
3-[4-(2-Dimethylamino-ethoxy)-2',6'-difluoro-biphenyl-3-yl]-1-(2-dimethylaminomethyl-phenyl)-propenone,
3-{4-[2-(tert-Butyl-methyl-amino)-ethoxy]-2'-methyl-biphenyl-3-yl}-1-(2-dimethylaminomethyl-phenyl)-propenone,
1-(2-Dimethylaminomethyl-phenyl)-3-[2'-methyl-4-(2-pyrrolidin-1-yl-ethoxy)-biphenyl-3-yl]-propenone,
3-[4-(2-Diethylamino-ethoxy)-2'-methyl-biphenyl-3-yl]-1-(2-dimethylaminomethyl-phenyl)-propenone,
3-[4-(3-Dimethylamino-propoxy)-2'-methyl-biphenyl-3-yl]-1-(2-fluoro-4-methoxy-phenyl)-propenone,
3-[4-(2-Dimethylamino-ethoxy)-2'-methoxy-biphenyl-3-yl]-1-(3-fluoro-4-hydroxy-phenyl)-propenone,
3-[4-(2-Dimethylamino-ethoxy)-3',5'-dimethyl-biphenyl-3-yl]-1-(3-fluoro-4-hydroxy-phenyl)-propenone,
3-[5-tert-Butyl-2-(2-dimethylamino-ethoxy)-phenyl]-1-(3-fluoro-4-hydroxy-phenyl)-propenone,
3-[2-(2-Dimethylamino-ethoxy)-5-methyl-phenyl]-1-(3-fluoro-4-hydroxy-phenyl)-propenone,
3-[2-(2-Dimethylamino-ethoxy)-5-methyl-phenyl]-1-(3-fluoro-4-methoxy-phenyl)-propenone,
3-[5-tert-Butyl-2-(2-dimethylamino-ethoxy)-phenyl]-1-(3-fluoro-4-methoxy-phenyl)-propenone,
3-[4-(2-Dimethylamino-ethoxy)-3',5'-dimethyl-biphenyl-3-yl]-1-(3-fluoro-4-methoxy-phenyl)-propenone,
3-(2,4-Dichloro-phenyl)-1-[4-(2-dimethylamino-ethoxy)-phenyl]-propenone,
3-{4-[5-(tert-Butyl-methyl-amino)-pentyloxy]-2'-methyl-biphenyl-3-yl}-1-(2-dimethylaminomethyl-phenyl)-propenone,
3-[4-(4-Diethylamino-butoxy)-2'-methyl-biphenyl-3-yl]-1-(2-dimethylaminomethyl-phenyl)-propenone,
3-{4-[4-(tert-Butyl-methyl-amino)-butoxy]-2'-methyl-biphenyl-3-yl}-1-(2-dimethylaminomethyl-phenyl)-propenone,
1-(2-Dimethylaminomethyl-phenyl)-3-[2'-methyl-4-(4-pyrrolidin-1-yl-butoxy)-biphenyl-3-yl]-propenone,
1-(2-Dimethylaminomethyl-phenyl)-3-[2'-methyl-4-(4-methylamino-butoxy)-biphenyl-3-yl]-propenone,
3-[4-(2-Dimethylamino-ethoxy)-2'-methyl-biphenyl-3-yl]-1-(4-dimethylaminomethyl-phenyl)-propenone,
3-[4-(2-Dimethylamino-ethoxy)-2'-methyl-biphenyl-3-yl]-1-(3-dimethylaminomethyl-phenyl)-propenone,
3-[4-(2-Dimethylamino-ethoxy)-3',5'-dimethyl-biphenyl-3-yl]-1-[4-hydroxy-2-(4piperazin-1-yl)-phenyl]-propenone,
3-(3,5-Di-tert-butyl-2-methoxy-phenyl)-1-[4-(2-dimethylamino-ethoxy)-2-(4-methyl-piperazin-1-yl)-phenyl]-propenone,
3-[4-(2-Dimethylamino-ethoxy)-3',5'-dimethyl-biphenyl-3-yl]-1-(2-fluoro-4-hydroxy-phenyl)-propenone,
3-[4-(2-Dimethylamino-ethoxy)-3',5'-dimethyl-biphenyl-3-yl]-1-[4-(2-dimethylamino-ethoxy)-2-fluoro-phenyl]-propenone,
3-(2,4-Dichloro-phenyl)-1-[4-(2-dimethylamino-ethoxy)-2-fluoro-phenyl]-propenone,
3-(2,4-Dichloro-phenyl)-1-[3-(2-dimethylamino-ethoxy)-phenyl]-propenone,
3-[5-tert-Butyl-2-(2-dimethylamino-ethoxy)-phenyl]-1-(4-hydroxy-phenyl)-propenone,
3-[4-(2-Dimethylamino-ethoxy)-biphenyl-3-yl]-1-(4-hydroxy-phenyl)-propenone,
1-(2-Dimethylaminomethyl-phenyl)-3-[2'-methyl-4-(5-pyrrolidin-1-yl-pentyloxy)-biphenyl-3-yl]-propenone,
3-[2-(2-Dimethylamino-ethoxy)-5-pyridin-3-yl-phenyl]-1-(2-dimethylaminomethyl-phenyl)-propenone,
3-[2-(2-Dimethylamino-ethoxy)-5-pyridin-2-yl-phenyl]-1-(2-dimethylaminomethyl-phenyl)-propenone,
3-[4-(2-Dimethylamino-ethoxy)-3'-methyl-biphenyl-3-yl]-1-(2-dimethylaminomethyl-phenyl)-propenone,
3-[3-(2-Dimethylamino-ethoxy)-2'-methyl-biphenyl-4-yl]-1-(2-dimethylaminomethyl-phenyl)-propenone,
3-[2'-Bromo-4-(2-dimethylamino-ethoxy)-biphenyl-3-yl]-1-(2-dimethylaminomethyl-phenyl)-propenone, 3-[4-(2-Dimethylamino-ethoxy)-4'-methyl-biphenyl-3-yl]-1-(2-dimethylaminomethyl-phenyl)-propenone, 3-[5-(2-Dimethylamino-ethoxy)-biphenyl-3-yl]-1-(2-dimethylaminomethyl-phenyl)-propenone, and salts thereof.

While the above-mentioned group of compounds is intended to include all stereoisomers, including optical isomers, and mixtures thereof, as well as pure, partially enriched, or, where relevant, racemic forms, a generally preferred embodiment of the above-mentioned compounds has the E-configuration at the enone functionality.

The invention further provides combinatorial libraries, mixtures and kits for screening compounds as defined above.

In one aspect, a combinatorial library comprising at least two compounds of the general formula is provided. Such library may be in the form of an equimolar mixture, or in a mixture of any stoichiometry. Typical embodiments comprise at least two, such as at least 10, such as at least 100, such as at least 1000, such as at least 10000, such as at least 100000 compounds as defined above.

In another aspect, combinatorial compound collections in the form of kits for screening for biologically or pharmacologically active compounds are provided. Such kits comprise at least two topologically distinct singular compounds of the general formula defined above. Typical kits comprise at least 10, such as at least 100, such as at least 1000, such as at least 10000, such as at least 100000 compounds as defined above. Kits are preferably provided in the form of solutions of the compounds in appropriate solvents.

Further provided are methods for screening for pharmacologically active compounds, especially bacteriostatic; bacteriocidal and antiparasitic agents, consisting of the steps of preparing a kit or library comprising at least two compounds of the general formula defined above, contacting said kit or library with a target molecule, such as a protein or nucleic acid, a target tissue, or a target organism, such as a bacterium or parasite, and detecting a biological or pharmacological response caused by at least one compound. Optionally, the steps may be repeated as appropriate to achieve deconvolution.

Definitions

In the present context, the term "bacteriostatic" is intended to describe an antimicrobial activity of a test compund, characterized by an inhibition of bacterial growth in the absence of a reduction of viable bacteria (bacterial kill) during incubation with the test compound, as evidenced in the killing curve determination by a stationary number of colony forming units, (CFU) during incubation time.

In the present context, the term "bacteriocidal" is intended to describe an antimicrobial activity of a test compound, characterized by the reduction of viable bacteria (bacterial kill) during incubation with the test compound, as evidenced in the killing curve determination by a reduction of colony forming units (CFU) during incubation time.

In the present contest, the term "antiparasitic" is intended to describe the ability of a test compound to upon incubation in vitro with a culture of parasites, e.g. *Leishmania major* or *Plasmodium falciparum*, to inhibit metabolic labelling of the parasites by at least 50% compared to mock treated control cultures.

In the present context, the term "$C_{1-12}$-alkyl" is intended to mean a linear, cyclic or branched hydrocarbon group having 1 to 12 carbon atoms, such as methyl, ethyl, propyl, iso-propyl, cyclopropyl, butyl, tert-butyl, iso-butyl, cyclobutyl, pentyl, cyclopentyl, hexyl, cyclohexyl, etc. Analogously, the term "$C_{1-6}$-alkyl" is intended to mean a linear, cyclic or branched hydrocarbon group having 1 to 6 carbon atoms, such as methyl, ethyl, propyl, iso-propyl, pentyl, cyclopentyl, hexyl, cyclohexyl, and the term "$C_1$-alkyl" is intended to cover linear, cyclic or branched hydrocarbon groups having 1 to 4 carbon atoms, e.g. methyl, ethyl, propyl, iso-propyl, cyclopropyl, butyl, iso-butyl, tert-butyl, cyclobutyl.

Whenever the term "$C_{1-12}$-alkyl" is used herein, it should be understood that a particularly interesting embodiment thereof is "$C_{1-6}$-alkyl".

Similarly, the terms "$C_{2-12}$-alkenyl", "$C_{4-12}$-alkadienyl", and "$C_{6-12}$-alkatrienyl" are intended to cover linear, cyclic or branched hydrocarbon groups having 2 to 12, 4 to 12, and 6 to 12, carbon atoms, respectively, and comprising one, two, and three unsaturated bonds, respectively. Examples of alkenyl groups are vinyl, allyl, butenyl, pentenyl, hexenyl, heptenyl, octenyl, heptadecaenyl. Examples of alkadienyl groups are butadienyl, pentadienyl, hexadienyl, heptadienyl, heptadecadienyl. Examples of alkatrienyl groups are hexatrienyl, heptatrienyl, octatrienyl, and heptadecatrienyl. Preferred examples of alkenyl are vinyl, allyl, butenyl, especially allyl.

Similarly, the term "$C_{2-12}$-alkynyl" is intended to mean a linear or branched hydrocarbon group having 2 to 12 carbon atoms and comprising a triple bond. Examples hereof are ethynyl, propynyl, butynyl, octynyl, and dodecaynyl.

Whenever the terms "$C_{2-12}$-alkenyl", "$C_{4-12}$-alkadienyl", "$C_{6-12}$-alkatrienyl", and "$C_{2-12}$-alkynyl" are used herein, it should be understood that a particularly interesting embodiment thereof are the variants having up to six carbon atoms.

In the present context, i.e. in connection with the terms "alkyl", "alkoxy", "alkenyl", "alkadienyl", "alkatrienyl", and "alkynyl", the term "optionally substituted" is intended to mean that the group in question may be substituted one or several times, preferably 1-3 times, with group(s) selected from hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkoxycarbonyl, $C_{1-6}$-alkylcarbonyl, formyl, aryl, aryloxycarbonyl, aryloxy, arylamino, arylcarbonyl, heteroaryl, heteroarylamino, heteroaryloxycarbonyl, heteroaryloxy, heteroarylcarbonyl, amino, mono- and di($C_{1-6}$-alkyl)amino, carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkyl-sulphonyl-amino, aryl-sulphonyl-amino, heteroaryl-sulphonyl-amino, $C_{1-6}$-alkanoyloxy, $C_{1-6}$-alkyl-sulphonyl, $C_{1-6}$-alkyl-sulphinyl, $C_{1-6}$-alkylsulphonyloxy, nitro, $C_{1-6}$-alkylthio, halogen, where any aryl and heteroaryl may be substituted as specifically describe below for "optionally substituted aryl and heteroaryl", and any alkyl, alkoxy, and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, or guanidine.

Preferably, the substituents are selected from hydroxy (which when bound to an unsaturated carbon atom may be present in the tautomeric keto form), $C_{1-6}$-alkoxy (i.e. $C_{1-6}$-alkyl-oxy), $C_{2-6}$-alkenyloxy, carboxy, oxo (forming a keto or aldehyde functionality), $C_{1-6}$-alkylcarbonyl, formyl, aryl, aryloxy, arylamino, arylcarbonyl, heteroaryl, heteroarylamino, heteroaryloxy, heteroarylcarbonyl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, guanidino, carbamido, $C_{1-6}$-alkyl-sulphonyl-amino, $C_{1-6}$-alkyl-sulphonyl, $C_{1-6}$-alkyl-sulphinyl, $C_{1-6}$-alkylthio, halogen, where any aryl and heteroaryl may be substituted as specifically describe below for "optionally substituted aryl and heteroaryl".

Especially preferred examples are hydroxy, $C_{1-6}$alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, and guanidine.

"Halogen" includes fluoro, chloro, bromo, and iodo.

In the present context the term "aryl" is intended to mean a fully or partially aromatic carbocyclic ring or ring system, such as phenyl, naphthyl, 1,2,3,4-tetrahydronaphthyl, anthracyl, phenanthracyl, pyrenyl, benzopyrenyl, fluorenyl and xanthenyl, among which phenyl is a preferred example.

The term "heteroaryl" is intended to mean a fully or partially aromatic carbocyclic ring or ring system where one or more of the carbon atoms have been replaced with heteroatoms, e.g. nitrogen (=N— or —NH—), sulphur, and/or oxygen atoms. Examples of such heteroaryl groups are oxazolyl, isoxazolyl, thiazolyl, isothiazolyl, pyrrolyl, imidazolyl, pyrazolyl, pyridinyl, pyrimidinyl, pyrazinyl, pyridazinyl, triazinyl, coumaryl, furyl, thienyl, quinolyl, benzothiazolyl, benzotriazolyl, benzodiazolyl, benzooxozolyl, phthalazinyl, phthalanyl, triazolyl, tetrazolyl, isoquinolyl, acridinyl, carbazolyl, dibenzazepinyl, indolyl, benzopyrazolyl, phenoxazonyl. Particularly interesting heteroaryl groups are oxazolyl, isoxazolyl, thiazolyl, isothiazolyl, pyrrolyl, imidazolyl, pyrazolyl, pyridinyl, pyrimidinyl, pyrazinyl, pyridazinyl, furyl, thienyl, quinolyl, triazolyl, tetrazolyl, isoquinolyl, indolyl in particular pyrrolyl, imidazolyl, pyridinyl, pyrimidinyl, thienyl, quinolyl, tetrazolyl, and isoquinolyl.

The term "heterocyclyl" is intended to mean a non-aromatic carbocyclic ring or ring system where one or more of the carbon atoms have been replaced with heteroatoms, e.g. nitrogen (=N— or —NH—), sulphur, and/or oxygen atoms. Examples of such heterocyclyl groups are imidazolidine, piperazine, hexahydropyridazine, hexahydropyrimidine, diazepane, diazocane, pyrrolidine, piperidine, azepane, azocane, aziridine, azirine, azetidine, pyroline, tropane, oxazinane (morpholine), azepine, dihydroazepine, tetrahydroazepine, and hexahydroazepine, oxazolane, oxazepane, oxazocane, thiazolane, thiazinane, thiazepane, thiazocane, oxazetane, diazetane, thiazetane, tetrahydrofuran, tetrahydropyran, oxepane, tetrahydrothiophene, tetrahydrothiopyrane, thiepane, dithiane, dithiepane, dioxane, dioxepane, oxathiane, oxathiepane. The most interesting examples are imidazolidine, piperazine, hexahydropyridazine, hexahydropyrimidine, diazepane, diazocane, pyrrolidine, piperidine, azepane, azocane, azetidine, tropane, oxazinane (morpholine), oxazolane, oxazepane, thiazolane, thiazinane, and thiazepane, in particular imidazolidine, piperazine, hexahydropyridazine, hexahydropyrimidine, diazepane, pyrrolidine, piperidine, azepane, oxazinane (morpholine), and thiazinane.

In the present context, i.e. in connection with the terms "aryl", "heteroaryl", and heterocyclyl, the term "optionally substituted" is intended to mean that the group in question may be substituted one or several times, preferably 1-5 times, in particular 1-3 times) with group(s) selected from hydroxy (which when present in an enol system may be represented in the tautomeric keto form), $C_{1-6}$-alkyl, $C_{1-6}$-alkoxy, $C_{2-6}$-alkenyloxy, oxo (which may be represented in the tautomeric enol form), carboxy, $C_{1-6}$-alkoxycarbonyl, $C_{1-6}$-alkylcarbonyl, formyl, aryl, aryloxy, arylamino, aryloxycarbonyl, arylcarbonyl, heteroaryl, heteroarylamino, amino, mono- and di($C_{1-6}$-alkyl)amino; carbamoyl, mono- and di($C_{1-6}$-alkyl) aminocarbonyl, amino-$C_{1-6}$-alkyl-aminocarbonyl, mono- and di($C_{1-6}$-alkyl)amino-$C_{1-6}$-alkyl-aminocarbonyl, $C_{1-6}$-alkylcarbonylamino, cyano, guanidino, carbamido, $C_{1-6}$-alkanoyloxy, $C_{1-6}$-alkyl-sulphonyl-amino, aryl-sulphonylamino, heteroaryl-sulphonyl-amino, $C_{1-6}$-alkyl-suphonyl, $C_{1-6}$-alkyl-sulphinyl, $C_{1-6}$-alkylsulphonyloxy, nitro, sulphanyl, amino, amino-sulfonyl, mono- and di($C_{1-6}$-alkyl)aminosulfonyl, dihalogen-$C_{1-4}$-alkyl, trihalogen-$C_{1-6}$-alkyl, halogen, where aryl and heteroaryl representing substituents may be substituted 1-3 times with $C_{1-4}$-alkyl, $C_{1-4}$-alkoxy, nitro, cyano, amino or halogen, and any alkyl, alkoxy, and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, or guanidine.

Preferably, the substituents are selected from hydroxy, $C_{1-6}$-alkyl, $C_{1-6}$-alkoxy, oxo (which may be represented in the tautomeric enol form), carboxy, $C_{1-6}$-alkylcarbonyl, formyl, amino, mono- and di($C_{1-6}$-alkyl)amino; carbamoyl, mono- and di($C_{1-6}$-alkyl)aminocarbonyl, amino-$C_{1-6}$-alkyl-aminocarbonyl, $C_{1-6}$-alkylcarbonylamino, guanidino, carbamido, $C_{1-6}$-alkyl-sulphonyl-amino, aryl-sulphonyl-amino, heteroaryl-sulphonyl-amino, $C_{1-6}$-alkyl-suphonyl, $C_{1-6}$-alkyl-sulphinyl, $C_{1-6}$-alkylsulphonyloxy, sulphanyl, amino, amino-sulfonyl, mono- and di($C_{1-6}$-alkyl)amino-sulfonyl or halogen, where any alkyl, alkoxy and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, or guanidine. Especially preferred examples are $C_{1-6}$-alkyl, $C_{1-6}$-alkoxy, amino, mono- and di($C_{1-6}$-alkyl)amino, sulphanyl, carboxy or halogen, where any alkyl, alkoxy and the like representing substituents may be substituted with hydroxy, $C_{1-6}$-alkoxy, $C_{2-6}$-alkenyloxy, amino, mono- and di($C_{1-6}$-alkyl)amino, carboxy, $C_{1-6}$-alkylcarbonylamino, halogen, $C_{1-6}$-alkylthio, $C_{1-6}$-alkyl-sulphonyl-amino, or guanidine.

In the present context the term "nitrogen-containing heterocyclic ring" is intended to mean heterocyclic ring or ring system in which at least one nitrogen atom is present. Such a nitrogen is, with reference to the formula, carrying the substituents $R_1$ and $R_2$. The "nitrogen-containing heterocyclic ring" may further comprise additional heteroatoms, e.g. nitrogen (=N— or —N—), sulphur, and/or oxygen atoms. Examples of such rings are aromatic rings such as pyridine, pyridazine, pyrimidine, pyrazine, triazine, thiophene, oxazole, isoxazole, thiazole, isothiazole, pyrrole, imidazole, pyrazole, tetrazole, quinoline, benzothiazole, benzotriazole, benzodiazole, benzoxozole, triazole, isoquinoline, indole, benzopyrazole, thiadiazole, and oxadiazole. The most interesting examples of aromatic rings are pyridine, pyridazine, pyrimidine, pyrazine, thiophene, tetrazole, oxazole, isoxazole, thiazole, isothiazole, pyrrole, imidazole, pyrazole, quinoline, triazole, isoquinoline, and indole, in particular pyridine, thiophene, imidazole, quinoline, isoquinoline, indole, and tetrazole.

Other examples of such rings are non-aromatic rings such as imidazolidine, piperazine, hexahydropyridazine, hexahydropyrimidine, diazepane, diazocane, pyrrolidine, piperidine, azepane, azocane, aziridine, azirine, azetidine, pyroline, tropane, oxazinane (morpholine), azepine, dihydroazepine, tetrahydroazepine, and hexahydroazepine, oxazolane, oxazepane, oxazocane, thiazolane, thiazinane, thiazepane, thiazocane, oxazetane, diazetane, and thiazetane. The most interesting examples of non-aromatic rings are imidazolidine, piperazine, hexahydropyridazine, hexahydropyrimidine, diazepane, diazocane, pyrrolidine, piperidine, azepane, azocane, azetidine, tropane, oxazinane (morpholine), oxazolane, oxazepane, thiazolane, thiazinane, and thiazepane, in particular imidazolidine, piperazine, hexahydropyridazine, hexahydropyrimidine, diazepane, pyrrolidine, piperidine, azepane, oxazinane (morpholine), and thiazinane.

In the present context, i.e. in connection with the term "nitrogen-containing heterocyclic ring", the term "optionally substituted" is intended to mean that the group in question may be substituted one or several times, preferably 1-5 times, in particular 1-3 times) with group(s) selected from the same substituents as defined above for "optionally substituted aryl".

As is evident from the formulae defined herein and the definitions associated therewith, certain compounds of the present invention are chiral. Moreover, the presence of certain unsaturated or cyclic fragments or multiple stereogenic atoms provides for the existence of diastereomeric forms of some of the compounds. The invention is intended to include all stereoisomers, including optical, isomers, and mixtures thereof, as well as pure, partially enriched, or, where relevant, racemic forms. In particular, many compounds of the invention may be in the form of E- or Z-stereoisomers, or mixtures of such isomers. The E-isomers are generally preferred.

It should furthermore be understood that the compounds defined herein include possible salts thereof, of which pharmaceutically acceptable salts are of course especially relevant for the therapeutic applications. Salts-include acid-addition salts and basic salts. Examples of acid addition salts are hydrochloride salts, fumarate, oxalate, etc. Examples of basic salts are salts where the (remaining) counter ion is selected from alkali metals, such as sodium and potassium, alkaline earth metals, such as calcium salts, potassium salts, and ammonium ions ($^+N(R')_4$, where the R's independently designate optionally substituted $C_{1-6}$-alkyl, optionally substituted $C_{2-6}$-alkenyl, optionally substituted aryl, or optionally substituted heteroaryl). Pharmaceutically acceptable salts are, e.g., those described in Remington's—The Science and Practice of Pharmacy, 20th Ed. Alfonso R. Gennaro (Ed.), Lippincott, Williams & Wilkins; ISBN: 0683306472, 2000, and in Encyclopedia of Pharmaceutical Technology. However, generally preferred salt forming agents for application in the present invention are organic dicarboxylic acids such as oxalic, fumaric, and maleic acid, and the like.

Thus, chalcones with aminoalkoxy groups can be prepared in their salt-forms thereby making the compounds particularly useful for pharmaceutical formulations. The use of appropriate selected salt form can be used to control the dissolution rate In vivo. Furthermore, the different salt forms have different bulk-properties that is of importance for the manufacturing process.

Preparation of Compounds

The aminoalkoxy-functional chalcones defined herein may be produced by methods known per se for the preparation of chalcones or methods that are analogous to such methods. Examples of excellent methods for preparing compounds of the 1,3-bis-aromatic-prop-2-enone or the 1,3-bis-aromatic-prop-2-ynone types are given in the following. Further examples of methods for the preparation of the compound used according to the present invention are described in WO 95/06628 and WO 93/17671 and in the references cited therein.

Compounds of the general formula I in which V is —CH=CH— can be prepared by reacting a ketone (an acetophenone in the case where $Ar^1$ is phenyl)

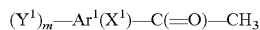

with an aldehyde (a benzaldehyde in the case where $Ar^2$ is phenyl)

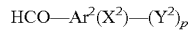

wherein $Ar^1$, $Ar^2$, $X^1$, $X^2$, $Y^1$, $Y^2$, m and p refer to the definitions given elsewhere herein.

This reaction, which is a condensation reaction, is suitably carried out under acid or base catalysed conditions. A review of such processes may be found in Nielsen, A. T., Houlihahn, W. J., Org. React. 16, 1968, p 1-444. In particular the method described by Wattanasin, S. and Murphy, S., Synthesis (1980) 647 has been found quite successful. The reaction may suitably be carried out in protic organic solvents, such as lower alcohols (e.g. methanol, ethanol, or tert-butanol), or lower carboxylic acids (formic, glacial acetic, or propionic acid), or in aprotic organic solvents such as ethers (e.g. tetrahydrofuran, dioxane, or diethyl ether), liquid amides (e.g. dimethylformamide or hexamethylphosphordiamide), dimethylsulfoxide, or hydrocarbons (e.g. toluene or benzene), or mixtures of such solvents. When carrying out the reaction under base catalysed conditions, the catalyst may be selected from sodium, lithium, potassium, barium, calcium, magnesium, aluminum, ammonium, or quaternary ammonium hydroxides, lower alkoxides (e.g. methoxides, ethoxides, tert-butoxides), carbonates, borates, oxides, hydrides, or amides of lower secondary amines (e.g. diisopropyl amides or methylphenyl amides). Primary aromatic amines such as aniline, free secondary amines such as dimethyl amine, diethyl amine, piperidine, or pyrrolidine as well as basic ion exchange resins may also be used.

Acid catalysts may be selected from hydrogen chloride, hydrogen bromide, hydrogen iodide, sulfuric acid, sulfonic acids (such as paratoluenesulfonic or methanesulfonic acid), lower carboxylic acids (such as formic, acetic or propionic acid), lower halogenated carboxylic acids (such as trifluoroacetic acid), Lewis acids (such as $BF_3$, $POCl_3$, $PCl_5$, or $FeCl_3$), or acid ion exchange resins.

A drawback of the base catalysed condensation is the poor yield obtained if the aromatic ring in which the ketone or the aldehyde or both is substituted with one or more hydroxy groups. This drawback can be overcome by masking the phenolic group as described by T. Hidetsugu et al. in EP 0 370 461. Deprotection is easily performed by mineral acids such as hydrochloric acid.

The reaction is typically carried out at temperatures in the range of 0-100° C., e.g. at room temperature. Reaction times are typically from 30 min to 24 hours.

The starting materials for the synthesis (acetophenone and benzaldehyde), may be obtained from commercial sources or may be synthesised according to well-known methods. The aminoalkoxy-benzaldehydes and aminoalkoxy-acetophenones can be synthesized by alkylation of the corresponding hydroxy-benzaldehydes or hydroxy-acetophenones (FIG. 1). Alternatively the aminoalkoxy-chalcones can be prepared by alkylation of the corresponding hydroxy-chalcone.

Compounds of the general formula I in which V is —C≡C— may be prepared by reacting an activated derivative of a carboxylic acid of the general formula

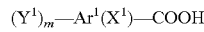

with an ethyne derivative

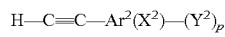

wherein $Ar^1$, $Ar^2$, $X^1$, $X^2$, $Y^1$, $Y^2$, m, and p refer to the definitions given elsewhere herein.

Reactions of this type are described by Tohda, Y., Sonogashihara, K., Haghara, N., *Synthesis* 1977, p 777-778. It is contemplated that the activated derivative of the carboxylic acid may be an activated ester, an anhydride or, preferably, an acid halogenide, in particular the acid chloride. The reaction is normally carried out using the catalysts described by Tohda, Y. et al. cited above, namely copper(I)iodide/triphenylphosphine-palladium dichloride. The reaction is suitably carried out in triethylamine, a mixture of triethylamine and pyridine or triethylamine and toluene under a dry inert atmosphere such as nitrogen or argon. The reaction is generally carried out at reduced temperature such as in the range from −80° C. to room temperature, the reaction time typically being from 30 minutes to 6 hours.

In the above reactions; it may be preferred or necessary to protect various sensitive or reactive groups present in the starting materials to prevent said groups from interfering with the reactions. Such protection may be carried out in a well-known manner, e.g. as described in "Protective Groups in Organic Chemistry" by Wuts and Greene, Wiley-Interscience; ISBN: 0471160199; 3nd edition (May 15, 1999). For example, in the reaction between the activated acid derivative and the acetylene derivative, a hydroxy group on $Ar^1$ and/or $Ar^2$ may be protected in the form of the methoxymethyl ether, N,N-dimethylcarbamoyl ester, or allyl ether. The protecting group may be removed after the reaction in a manner known per se.

The ethyne derivative may be prepared by standard methods, e.g. as described by Nielsen, S. F. Et al., Bioorg. Med. Chem. 6, pp 937-945 (1998). The carboxylic acids may likewise be prepared by standard procedures, e.g. as described in the examples.

Compounds of the general formula I in which V is —$CH_2$—$CH_2$— can be prepared by ionic hydrogenation of the corresponding α,β-unsaturated compound where V is —CH=CH— as it has been described by the inventors in Nielsen, S. F. et al. Tetrahedron, 53, pp 5573-5580 (1997).

Further possible synthetic routes for the preparation of the saturated variants are described in "Advanced Organic Chemistry" by Jerry March, $3^{rd}$ ed. (especially chapter 15, pages 691-700) and references cited therein. Thus, it is possible to obtain a large variety of compounds of the 1,3-bis-aromatic-propan-1-one type from the corresponding prop-2-en-1-ones.

Therapeutic Uses

The present inventors have found that that the novel compound have interesting properties as bacteriostatic, bacteriocidal and antiparasitic agents (see the Examples section). It is, of course, possible that the compounds also have other interesting properties to be utilised in the medical field.

Thus, the present invention provides, in,one aspect, a compound (chalcone derivative) as defined herein for use as a drug substance, i. e. a medicament.

Moreover, further aspects the invention relate to the use of the compounds as defined herein for the preparation of a medicament for the treatment of infections, such as infections associated with bacteria, protozoas or *Leishmania* spp.

The invention also provides, in still further aspects, methods for the treatment of infections such as infections associated with bacteria, protozoa or *Leishmania* spp in a mammal, comprising the administration of the compounds as defined herein to said mammal.

In one aspect, the chalcone derivatives may be used for the treatment of bacterial infections in a mammal in need thereof. Such bacterial infections may be associated with common Gram-positive and/or Gram-negative pathogens or with microaerophilic or anaerobic bacteria. As a particularly relevant example of bacteria against which chalcone derivatives demonstrates an effect can be mentioned antibiotic-sensitive or -resistant strains of *S.aureus* and/or *E.faecium*. Other examples include community acquired and nosocomial respiratory infections, including *S.pneumoniae, S.pyogenes* and members of Enterobacteriaceae (e.g. *E.coli*), microaerophilic bacteria associated with gastric disease (e.g. *Helicobacter pylori*) or pathogenic anaerobic bacteria (e.g. *Bacteroides fragilis* and *Clostridium* species).

According to the present invention, particularly relevant compounds for treatment of such bacterial infections may be defined by the following preferred embodiments.

In one preferred embodiment $Ar^1$ and $Ar^2$ are both phenyl, m is 0, p is 1, and V is —CH=CH—. Further, the location of the group $Y^2$ is preferably the 2-, 3- or 4-position, most suitably the 2-position. Additional substituents defined by $X^2$ may typically be selected from the list, comprising alkyl, alkenyl, and optionally substituted phenyl. $X^2$ typically designates one substituent, preferably located in the 5-position. Further preferred compounds of such embodiments include those wherein $X^1$ represents 0-3, such as one, amino, hydroxy, alkylsulfonylamido, alkylamido, alkyl, or halo group located in the 2-, 3-, or 4-position, and those wherein $X^1$ represents 0-3, such as one, dialkylaminomethyl group located In the 2-, 3-, or 4-position, and those wherein $X^1$ represents 0-3, such as one, dialkyaminomethyl group located in the 2-, or 3-position supplemented by a alkoxy or hydroxy group in the 4- or 5-position, and those wherein $X^1$ represents 0-3, such as one, substituent of the formula —$NR''$—B—$N(R^P)R^q$ located in the 2- or 3-position.

Also preferred are compounds where $Ar^1$ and $Ar^2$ are both phenyl, m is 1, p is 1, and V is —CH=CH—. Further, the location of the group $Y^2$ is preferably the 2-, 3- or 4-position, most suitably the 2-position. The location of the $Y^1$ substituent is suitably the 2-, 3-, or 4-position.

In another preferred embodiment $Ar^1$ and $Ar^2$ are both phenyl, m is 0, p is 1, and V is —$CH_2$—$CH_2$—. Further, the location of the group $Y^2$ is preferably the 2-, 3- or 4-position, most suitably the 2-position. Additional substituents defined by $X^2$ may typically be selected from the list comprising alkyl, alkenyl, and optionally substituted phenyl. $X^2$ typically designates one substituent, preferably located in the 5-position. Further preferred compounds of such embodiments include those wherein $X^1$ represents 0-3, such as one, amino, hydroxy, alkylsulfonylamido, alkylamido, alkyl, or halo group located in the 2-, 3-, or 4-position, and those wherein $X^1$ represents 0-3, such as one, dialkylaminomethyl group located in the 2-, 3-, or 4-position, and those wherein $X^1$ represents 0-3, such as one, dialkyaminomethyl group located in the 2- or 3-position supplemented by a hydroxy group in the 4-, or 5-position, and those wherein $X^1$ represents 0-3, such as one, substituent of the formula —$NR''$—B—N($R^P$)$R^q$ located in the 2- or 3-position.

Also preferred are compounds where $Ar^1$ and $Ar^2$ are both phenyl, m is 1, p is 1, and V is —$CH_2$—$CH_2$—. Further, the location of the group $Y^2$ is preferably the 2-, 3- or 4-position, most suitably the 2-position. The location of the $Y^1$ substituent is suitably the 2-, 3-, or 4-position.

Additionaly, compounds wherein $Ar^1$ and $Ar^2$ are both phenyl, m is 1, p is 0, and V is —CH=CH—are interesting, especially when $Y^1$ is located in the 2-, 3-, or 4-position; and $X^2$ represents 2- and/or 4-substitution, suitably halo.

In still another aspect, the chalcone derivatives as provided herein can be used for the treatment of infections associated with protozoa in a mammal. Examples of infections are those caused by a protozoa selected from *Plasmodium falciparum, Plasmodium vivax, Plasmodium ovale* and *Plasmodium malariae*.

In a still further aspect, the chalcone derivatives as defined herein can be used for the treatment of infections in a mammal associated with *Leishmania* spp. Such infections may be cutaneous and/or visceral.

Preliminary results have shown that compounds wherein the $Y^2$ is the aminoalkoxy-substituent positioned in the 2 position where $Ar^1$ is phenyl, are particularly promising for the treatment of infections caused by Plasmodium. Those in which $X^2$ represents at least one substituent selected from $C_{1-6}$-alkyl, hydroxy, $C_{1-6}$-alkoxy, $C_{1-6}$-alkylcarbonyl, optionally substituted aryl, optionally substituted aryloxy, optionally substituted arylamino, optionally substituted heteroaryl, optionally substituted heteroarylamino, mono- and di($C_{1-6}$-alkyl)amino, $C_{1-6}$-alkyl-carbonylamino, optionally substituted $C_{1-6}$-alkylthio, optionally substituted heterocyclyl, optionally substituted heterocyclyloxy, optionally substituted heterocyclylamino and halogen, in particular from $C_{1-6}$-alkyl, optionally substituted phenyl, and hydroxy, e.g. from $C_{1-6}$-alkyl and optionally substituted phenyl, appear to be particularly promising. Particular examples of efficient chalcone derivatives are those where $X^1$ represents at least one substituent, one of which being located in the 2- or 3-position of the phenyl ring, and preferably being selected from amino-$C_{1-6}$-alkyl and mono- and di($C_{1-6}$-alkyl)amino-$C_{1-6}$-alkyl, or those where $X^1$ represents at least one substituent, one of which being located in the 4-position of the phenyl ring, and preferably being selected from hydroxy, amino-$C_{1-6}$-alkylamino and mono- and di($C_{1-6}$-alkyl)amino-$C_{1-6}$-alkylamino.

One particularly suitable embodiment for such application is the one wherein $Ar^1$ and $Ar^2$ are both phenyl, m is 0, p is 1, and V is —CH=CH—. Further preferred among such compounds are the ones wherein $Y^2$ is located in the 2-position, and designates a group of formula —O—$(CH_2)_{2-3}$—N($R^1$)$R^2$, wherein $R^1$ and $R^2$ are independently alkyl or N-containing heterocyclic ring, such as methyl, ethyl, t-butyl, pyrrolidine; and the like. Also preferred are compounds which additionally carry a substituent as defined by $X^2$, suitably located in the 5-position, and selected from alkyl and optionally substituted aryl, such as optionally substituted phenyl. In such embodiments, substituents defined by $X^1$, if present, may typically be selected so that $X^1$ is dialkylaminomethyl located in the 2-, or 3-position, optionally supplemented by methoxy or hydroxy groups in the 4- and/or 5-positions, or selected so that $X^1$ represents 1-3 halo, alkoxy or hydroxy substituents located in the 2-, 3-, or 4-positions, such as 2,3-dihalo-4-hydroxy, 4-halo, 2-halo-3-hydroxy, 2-butoxy, and the like, or selected so that $X^1$ represents a group of the formula —NR$^n$—B—N(R$^p$)R$^q$, preferably 2- or 3-(4-alkylpiperazin-1-yl), 3- or 4-((2-(dialkylamino)ethyl)amino), or 2-((2-(dialkylamino)ethyl)methylamino).

Another particularly suitable embodiment such for application is the one wherein $Ar^1$ and $Ar^2$ are both phenyl, m is 0, p is 1, and V is —CH=CH—, and $Y^2$ is located in the 3-position, and designates a group of formula —O—$(CH_2)_{2-3}$—N($R^1$)$R^2$, wherein $R^1$ and $R^2$ are independently alkyl. Among such compounds, $X^1$ may typically be a dialkylaminomethyl substituent, such as dimethylaminomethyl, suitably located in the 2-position.

Also interesting for such application are compounds wherein $Ar^1$ and $Ar^2$ are both phenyl, m is 1, p is 1, and V is —CH=CH—. Among such compounds, preferred meanings of $Y^1$ and $Y^2$ include —O—$(CH_2)_{2-3}$—N($R^1$)$R^2$, wherein $R^1$ and $R^2$ are independently alkyl, such as methyl. Suitable selections of $X^1$ and $X^2$, if present, are halo, particularly 2-halo, such as 2-fluoro, and aryl, particularly optionally substituted 5-phenyl.

Other preliminary results have shown that compounds wherein the $Y^2$ is the aminoalkoxy-substituent positioned in the 2 position where $Ar^1$ is phenyl, are particularly promising for the treatment of infections caused by *Leishmania* spp. Those in which $X^2$ represents at least one substituent selected from $C_{1-6}$-alkyl, hydroxy, $C_{1-6}$-alkoxy, $C_{1-6}$-alkylcarbonyl, optionally substituted aryl, optionally substituted aryloxy, optionally substituted arylamino, optionally substituted heteroaryl, optionally substituted heteroarylamino, mono- and di($C_{1-6}$-alkyl)amino, $C_{1-6}$-alkylcarbonylamino, optionally substituted $C_{1-6}$-alkylthio, optionally substituted heterocyclyl, optionally substituted heterocyclyloxy, optionally substituted heterocylylamino and halogen, in particular from $C_{1-6}$-alkyl, optionally substituted phenyl, and hydroxy, e.g. from $C_{1-6}$-alkyl and optionally substituted phenyl, appear to be particularly promising.

Particularly suitable embodiments for such application include those wherein $Ar^1$ and $Ar^2$ are both phenyl, the sum of m and p is 1, and V is —CH=CH—. Typically, in such compounds, n is 2-6, such as 2 or 3, and the location of $Y^1$ or $Y^2$ is in the 2-, 3-, or 4-position, with the 2-position being especially preferred. Further, in such embodiments where m is 1, $Y^1$ may typically be supplemented with additional groups $X^2$, suitably selected from non-charged substituents such as alkyl, alkoxy and halo, and located in the 2-, 3-, or 4-positions. In embodiments where p is 1, $Y^2$ may typically be supplemented by additional substituents, $X^2$, suitably selected from non-charged, bulky groups such as alkyl and aryl and/or by substituents defined by $X^1$, suitably selected from non-charged groups such as alkyl, alkoxy and halo. Further, generally interesting embodiments are those where $X^1$ designates a dialkylaminomethyl group, suitably located in the 2-position.

Still other preliminary results indicate that compounds wherein the $Y^2$ is the aminoalkoxy-substituent positioned in the 2 position where $Ar^1$ is phenyl, are particularly promising for the treatment of infections caused by *S. aureus*. Those in which $X^2$ represents at least one substituent selected from $C_{1-6}$-alkyl, hydroxy, $C_{1-6}$-alkoxy, $C_{1-6}$-alkylcarbonyl, optionally substituted aryl, optionally substituted aryloxy, optionally substituted arylamino, optionally substituted heteroaryl, optionally substituted heteroarylamino, mono- and di($C_{1-6}$-alkyl)amino, $C_{1-6}$-alkylcarbonylamino, optionally substituted $C_{1-6}$-alkylthio, optionally substituted heterocyclyl, optionally substituted heterocyclyloxy, optionally substituted heterocyclylamino and halogen, in particular from $C_{1-6}$-alkyl, optionally substituted phenyl, and hydroxy; e.g. from $C_{1-6}$-alkyl and optionally substituted phenyl, appear to be particularly promising.

Formulation of Pharmaceutical Compositions

The chalcone derivatives are typically formulated in a pharmaceutical composition prior to use as a drug substance.

The administration route of the compounds (aminoalkoxy-functional chalcones) as defined herein may be any suitable route that leads to a concentration in the blood or tissue corresponding to a therapeutic concentration. Thus, e.g., the following administration routes may be applicable although the invention is not limited thereto: the oral route, the parenteral route, the cutaneous route, the nasal route, the rectal route, the vaginal route and the ocular route. It should be clear to a person skilled in the art that the administration route is dependant on the particular compound in question, particularly, the choice of administration route depends on the physico-chemical properties of the compound together with the age and weight of the patient and on the particular disease or condition and the severity of the same.

The compounds as defined herein may be contained in any appropriate amount in a pharmaceutical composition, and are generally contained in an amount of about 1-95% by weight of the total weight of the composition. The composition may be presented in a dosage form which is suitable for the oral, parenteral, rectal, cutaneous, nasal, vaginal and/or ocular administration route. Thus, the composition may be in form of, e.g., tablets, capsules, pills, powders, granulates, suspensions, emulsions, solutions, gels including hydrogels, pastes, ointments, creams, plasters, drenches, delivery devices, suppositories, enemas, injectables, implants, sprays, aerosols and in other suitable form.

The pharmaceutical compositions may be formulated according to conventional pharmaceutical practice, see, e.g., "Remington's Pharmaceutical Sciences" and "Encyclopedia of Pharmaceutical Technology", edited by Swarbrick, J. & J. C. Boylan, Marcel Dekker, Inc., New York, 1988. Typically, the compounds defined herein are formulated with (at least) a pharmaceutically acceptable carrier or exipient. Pharmaceutically acceptable carriers or exipients are those known by the person skilled in the art.

Thus, the present invention provides a pharmaceutical composition comprising a compound as defined herein in combination with a pharmaceutically acceptable carrier.

Pharmaceutical compositions according to the present invention may be formulated to release the active compound substantially immediately upon administration or at any substantially predetermined time or time period after administration. The latter type of compositions are generally known as controlled release formulations.

In the present context, the term "controlled release formulation" embraces i) formulations which create a substantially constant concentration of the drug within the body over an extended period of time, ii) formulations which after a predetermined lag time create a substantially constant concentration of the drug within the body over an extended period of time, iii) formulations which sustain drug action during a predetermined time period by maintaining a relatively, constant, effective drug level in the body with concomitant minimization of undesirable side effects associated with fluctuations in the plasma level of the active drug substance (sawtooth kinetic pattern), iv) formulations which attempt to localize drug action by, e.g., spatial, placement of a controlled release composition adjacent to or in the diseased tissue or organ, v) formulations which attempt to target drug action by using carriers or chemical derivatives to deliver the drug to a particular target cell type.

Controlled release formulations may also be denoted "sustained release", "prolonged release", "programmed release", "time release", "rate-controlled" and/or "targeted release" formulations.

Controlled release pharmaceutical compositions may be presented in any suitable dosage forms, especially in dosage forms intended for oral, parenteral, cutaneous nasal, rectal, vaginal and/or ocular administration. Examples include single or multiple unit tablet or capsule compositions, oil solutions, suspensions, emulsions, microcapsules, microspheres, nanoparticles, liposomes, delivery devices such as those intended for oral, parenteral, cutaneous, nasal, vaginal or ocular use.

Preparation of solid dosage forms for oral use, controlled release oral dosage forms, fluid liquid compositions, parenteral compositions, controlled release parenteral compositions, rectal compositions, nasal compositions, percutaneous and topical compositions, controlled release percutaneous and topical compositions, and compositions for administration to the eye can be performed essentially as described in the applicant's earlier International application No. WO 99/00114, page 29, line 9, to page 40, line 3. Also, and more generally, the formulation and preparation of the above-mentioned compositions are well-known to those skilled in the art of pharmaceutical formulation. Specific formulations can be found in "Remington's Pharmaceutical Sciences".

Dosages

The compound are preferably administered in an amount of about 0.1-50 mg per kg body weight per day, such as about 0.5-25 mg per kg body weight per day.

For compositions adapted for oral administration for systemic use, the dosage is normally 2 mg to 1 g per dose administered 1-4 times daily for 1 week to 12 months depending on the disease to be treated.

The dosage for oral administration for the treatment of parasitic diseases is normally 1 mg to 1 g per dose administered 1-2 times daily for 1-4 weeks, in particular the treatment of malaria is to be continued for 1-2 weeks whereas the treatment of *leishmaniasis* will normally be carried out for 3-4 weeks.

The dosage for oral administration for the treatment of bacterial diseases is normally 1 mg to 1 g per dose administered 1-4 times daily for 1 week to 12 months; in particular, the treatment of tuberculosis will normally be carried out for 6-12 months.

The dosage for oral administration of the composition in order to prevent diseases is normally 1 mg to 75 mg per kg body weight per day. The dosage may be administered once or twice daily for a period starting 1 week before the exposure to the disease until 4 weeks after the exposure.

For compositions adapted for rectal use for preventing diseases, a somewhat higher amount of the compound is usually preferred, i.e. from approximately 1 mg to 100 mg per kg body weight per day.

For parenteral administration, a dose of about 0.1 mg to about 50 mg per kg body weight per day is convenient. For intravenous administration a dose of about 0.1 mg to about 20 mg per kg body weight per day administered for 1 day to 3 months is convenient. For intraarticular administration a dose of about 0.1 mg to about 20 mg per kg body weight per day is usually preferable. For parenteral administration in general, a solution in an aqueous medium of 0.5-2% or more of the active ingredients may be employed.

For topical administration on the skin, a dose of about 1 mg to about 5 g administered 1-10 times daily for 1 week to 12 months is usually preferable.

In many cases, it will be preferred to administer the compound defined herein together with another antiparasitic, antimycotic or antibiotic drug, thereby reducing the risk of development of resistance against the conventional drugs, and reducing the amount of each of the drugs to be administered, thus reducing the risk of side effects caused by the conventional drugs. Important aspects of this is the use of the compound against *Leishmania*, where the compound is combined with another antileishmanial drug, or the antimalarial use of the compound where the compound is used together with another antimalarial drug.

Method of Prediction

In a separate aspect, the present invention also provides a method of predicting whether a chemical compound has a potential inhibitory effect against a microorganism selected from *Helicobacter pylori* and *Plasmodium falciparum*, said method comprising preparing a mixture of a dihydroorotate dehydrogenase, a substrate for dihydroorotate dehydrogenase and the chemcial compound, measuring the enzymatic activity of dihydroorotate dehydrogenase (A), comparing the enzymatic activity of dihydroorotate dehydrogenase (A) with the standard activity of dihydroorotate dehydrogenase (B) corresponding to the activity of a dihydroorotate dehydrogenase in a similar sample, but without the chemical compound, predicting that the chemical compound has a potential inhibitory effect against *Helicobacter pylori* and *Plasmodium falciparum* if A is significantly lower than B.

The method can be performed as described under DHODH Assay in the Examples section. It should be noted that the method is not only applicable for the chalcone derivatives defined herein, but can be generally applied to predict the potential inhibitory effect of any compound. Preferably, however, the chemical compound is a chalcone derivative, e.g. a chalcone derivative as defined herein.

EXAMPLES

Preparation of Compounds

Chemical names presented below were generated using the software ChemDraw Ultra, version 6.0.1, from CambridgeSoft.com.

The general method for the preparation of the A ring or B ring having the aminoalkoxy-functional group is illustrated in FIG. 1.

Characterisation of the Compounds

The compounds were characterised by NMR (300 MHz) and GC-MS or LC-MS. The purity of the chalcone derivatives was >95% determined by HPLC.

General Procedure A

Preparation of alkyl- or dialkyl aminomethyl acetophenones

To a solution of (2-methyl-[1,3]dioxan-2-yl) benzaldehyde (165 mmol) and amine (247 mmol) in dry THF (1.5 L) was added sodium triacetoxyborohydride (257 mmol) under argon. The resulting suspension was stirred at room temperature for 18 hr. A solution of sodium hydroxide (2M) was added and stirring was continued for approximately 30 min, before the mixture was acidified using HCl (6M). The mixture was stirred for 1 hr. and extracted with diethyl ether, which was discarded. The pH of the aqueous phase was adjusted to 11-14 using sodium hydroxide and extracted again with diethyl ether. The latter organic phase, was dried ($Na_2SO_4$), filtered and evaporated to give the title products, which were used without further purification.

General Procedure B

Preparation of Amino Acetophenones

3'- or 4'-bromoacetophenone ketal (40 mmol), amine (48 mmol), $Pd_2(dba)_3$ (0.2 mmol, 1 mol % Pd), rac-BINAP (0.6 mmol) and Na-t-OBu (68 mmol) was stirred in degassed toluene (60 mL) at 80° C. for 18 h. The darkbrown mixture was poured into ice cold hydrochloric acid (1M, 200 mL) and stirred vigorously for 2 hours at 25° C. The solution was cooled to 0° C. and pH was adjusted to 13 using 6M NaOH (aq) and extracted with $Et_2O$ (4×100 mL). The organic phase was dried ($K_2CO_3$) and the solvent was removed under reduced pressure. The resulting crude oil purified by flash chromatography using 5% $Et_3N$ in EtOAc.

General Procedure C

Preparation of (2-dimethylaminoethoxy)-acetophenones

A solution of hydroxy acetophenone (48 mmol), 2-(dimethylamino)ethyl chloride, HCl (96 mmol) and $K_2CO_3$ (48 mmol) in dry DMF (300 mL) was refluxed overnight. The reaction was cooled to room temperature and added 2 M $NH_3$ solution (aq) (600 mL) and extracted with diethyl ether. The combined organic phases were dried (Na2SO4) and evaporated in vacuo. The residue purified by column chromatography gave the title compound.

General Procedure D

Preparation of (3-dimethylaminopropoxy)-acetophenones

A solution of hydroxy acetophenone (48 mmol), 3-(dimethylamino)propyl chloride, HCl (96 mmol) and 60% NaH (48 mmol) in dry DMF (300 mL) was heated to 100° C. for 3 h. The reaction was cooled to room temperature and added 2 M $NH_3$ solution (aq) (600 mL) and extracted with $CH_2Cl_2$ (3×200 mL). The combined organic phases were dried ($Na_2SO_4$) and evaporated in vacuo. The resulting yellow solution was redissolved in water (500 mL) and extracted with diethyl ether. The combined organic phases were dried ($Na_2SO_4$) and evaporated in vacuo. The residue purified by column chromatography gave the title compound.

General Procedure E

Preparation of (2-dimethylaminoethoxy)-benzaldehydes

A stirred solution of hydroxybenzaldehyde (59.7 mmol) in dry toluene (200 mL) and DMSO (1 mL) was added 60% NaH (60 mmol) under ice cooling. The reaction was slowly heated to room temperature. 2-(dimethylamino)ethyl chloride, HCl (110 mmol) dissolved in water (50 mL) was added NaOH (110 mmol) and the aqueous phase was extracted with toluene (3×30 mL). The combined organic phases were dried ($Na_2SO_4$) and slowly added to the reaction. The solution was heated to 90° C. for 16 h. The reaction mixture was cooled to room temperature and washed with water (3×100 mL), 2N NaOH (100 mL) and dried ($Na_2SO_4$). Evaporation in vacuo gave the title products.

General Procedure F

Preparation of (3-dimethylaminopropoxy)-benzaldehydes/or -biaryl carbaldehydes

A stirred solution of hydroxybenzaldehyde/hydroxy biaryl carbaledehyde (59.7 mmol) in dry toluene (200 mL) and DMSO (1 mL) was added 60% NaH (60 mmol) under ice cooling. The reaction was slowly heated to room temperature. 3-Dimethylaminopropylchloride, HCl (110 mmol) dissolved in water (50 mL) was added NaOH (110 mmol) and the aqueous phase was extracted with toluene (3×30 mL). The combined organic phases were dried ($Na_2SO_4$) and slowly added to the reaction. The solution was heated to 90° C. for 16 h. The reaction mixture was cooled to room temperature and washed with water (3×100 mL), 2N NaOH (100 mL) and dried (Na$_2$SO$_4$). Evaporation in vacuo gave the title products.

General Procedure G

Preparation of Biaryl Carbaldehydes

A solution of Na2CO3 (44 mmol) in water, (20 mL) was added to a solution of bromobenzaldehyde (14.7 mmol) and (hetero)arylboronic acid (17.6 mmol) in DME (40 mL). The mixture was flushed with argon for 2 minutes followed by addition of Pd(PPh$_3$)$_2$Cl$_2$ (310 mg, 3 mol %). The reaction was heated at reflux and left overnight under an atmosphere of argon. The reaction was cooled, 2M Na$_2$CO$_3$ was added, and the mixture was extracted with EtOAc (3×20 mL). The title products were purified by flash chromatography.

General Procedure H

Synthesis of Chalcones

To a solution of an acetophenone (2 mmol) and a benzaldehyde (2 mmol) in 96% EtOH (10 mL) was added 8M NaOH (0.3 mL), and the mixture was stirred for 3-18 hours at 25° C. The mixture was evaporated on Celite® and the product was isolated by flash chromatography. The aminochalcone was dissolved in MeOH:Et$_2$O (1:9 v/v, 10 mL) and a solution of fumaric acid or oxalic acid in MeOH:Et$_2$O (1:9 v/v) was added. The salt was filtered off and recrystallised from MeOH or MeCN. Alternatively, the aminochalcone was dissolved in EtOH before 3M HCl in EtOH was added at room temperature. The salt was filtered off. Some aminochalcones did not undergo salt formation, and was isolated as the free base.

General Procedure I

Preparation of (2-dimethylaminoethoxy)-chalcones

A solution of hydroxy chalcone (3.5 mmol), 2-(dimethylamino)ethyl chloride, HCl (3.5 mmol) and K$_2$CO$_3$ (10.5 mmol) in dry DMF (20 mL) was heated to reflux for 3 h. The reaction was cooled to room temperature and added 2 M NH$_3$ solution (aq) and extracted with ether. The combined organic phases were dried (Na$_2$SO$_4$) and evaporated in vacuo. The residue purified by column chromatography gave the title compound.

General Procedure J

Formylation of 2-(biphenyl-4-yloxy)-ethyl]-dimethyl-amine

A solution of TiCl$_4$ in CH$_2$Cl$_2$ (3 M, 149 mmol) was added under argon at 0° C. to a solution of 1,1-dichloro methyl methyl ether (10 mL) and 2-(biphenyl-4-yloxy)-ethyl]-dimethyl-amine (13.5 mmol) in CH$_2$Cl$_2$. Allowed to warm to RT during 3 hours. Poured onto ice and the pH was adjusted to basic pH using 2M NaOH. The phases were separated and the aqueous phase was extracted with CH$_2$Cl$_2$. The combined organic phases were dried (Na$_2$SO$_4$) and evaporated to give the pure title products.

General Procedure K

Synthesis of Amines from Alkyl Halides

A solution of halide (4.5 mmol), amine (22.5 mmol) and sodium iodide (13.5 mmol) in DMF (50 mL) and water (5 mL) was heated at 95° C. overnight. The reaction was cooled and added water and extracted with ether (3×100 mL). The collected organic phases were evaporated in vacuo and redissolved in EtOAc (50 mL). The solution was added 2M HCl (50 mL) and stirred for 2 hours at room temperature. Addition of 2N NaOH to neutral pH and separation of the organic and aqueous phase gave yellow oil that was purified by flash chromatography.

General Procedure L

Alkylation of Phenols with Alkyl Dihalides

A solution of phenol (20.3 mmol) and alkyl dihalide (100 mmol) in THF (100 mL) and 2M NaOH aq (50 mL) was left overnight at 70 C under vigorous stirring. The reaction was cooled and added water and extracted with ether (3×100 mL). The title products were purified by flash chromatography.

General Procedure M

Preparation of 2-(biphenyl-4-yloxy)-ethyl]-dimethyl-amine

A solution of biphenyl-4-ol (18 mmol), 2-(dimethylamino) ethyl chloride, HCl (27 mmol) and K$_2$CO$_3$ (54 mmol) in acetone (200 mL) was refluxed overnight. The reaction was cooled to room temperature, poured into water, and extracted with ethyl acetate. The combined organic phases were dried (Na$_2$SO$_4$) and evaporated in vacuo. The residue was used without further purification.

General Procedure N

Reduction of Chalcones

Triethylsilane (0.150 mol) was added to a solution of 3,1-diphenyl propenone (0.0075 mol) in trifluoro acetic acid. Stirred at 25° C. for 30 hours, before the solution was poured into ice-cold NaOH (2M, 150 mL). Extracted with EtOAc, dried over Na$_2$SO$_4$, filtered and evaporated on Celite®. Purified by flash chromatography (EtoAc/heptane, 3% Et$_3$N). The resulting oil was dissolved in MeOH:Et$_2$O (1:9 v/v, 10 mL) and a solution of fumaric acid in MeOH:Et$_2$O (1:9 v/v) was added. Some propanones did not undergo salt formation, and was isolated as the free base. The purity was >95% determined by HPLC and the molecular weight was determined by LC-MS.

General Procedure O

Nucleophilic Aromatic Substitution on Fluoroacetophenone

A mixture of fluoroacetophenone (40, mmol), amine (50 mmol), K$_2$CO$_3$ (50 mmol) was refluxed in dry DMF (20 mL) under an argon atmosphere for 18 h. The DMF was removed using an oilpump and water (50 mL) was added to the residue. The water phase was extracted with Et$_2$O (2×100 mL) and the organic phase was dried (K$_2$CO$_3$) and evaporated to yellow oil, which was pure enough for further reaction.

Acetophenones

1-[2-(4-Methyl-piperazin-1-ylmethyl)-phenyl]-ethanone

General procedure A gave the title compound as a brown oil in 78% yleld. $^1$H-NMR (CDCl$_3$) δ 7.42-7.29 (m, 4H), 3.65 (s, 2H), 2.54 (s, 3H), 2.43 (b, 8H), 2.27 (s, 3H).

1-(2-{[(2-Dimethylamino ethyl)-methyl-amino]-methyl}-phenyl)-ethanone

General procedure A gave the title compound as brown oil in. 88% yleld. $^1$H-NMR (DMSO-d$_6$) δ 7.51 (d, 1H), 7.40-7.30 (m, 3H), 3.57 (s, 2H), 2.56 (s, 3H), 2.39-2.32 (m, 2H), 2.29-2.23 (m, 2H), 2.07 (s, 6H), 2.03 (s, 3H).

1-{2-[(tert-Butyl-methyl-amino)-methyl]-phenyl}-ethanone

General procedure A gave the title compound as brown oil in 44% yleld. $^1$H-NMR (DMSO-d$_6$) δ
7.52 (dd, 1H), 7.51 (dd, 1H), 7.40 (td, 1H), 7.30 (td, 1H), 3.63 (s, 2H), 2.48 (s, 3H), 1.91 (x, 3H), 1.03 (s, 9H).

1-[2-(4-Hydroxy-piperidin-1-ylmethyl)-phenyl]-ethanone

General procedure A gave the title, compound as brown oil in 82% yleld. $^1$H-NMR (CDCl$_3$) δ 7.32 (dt, 1H), 7.28-7.19 (m, 3H), 3.65-3.56 (m, 1H), 3.54 (s, 2H), 2.63-2.55 (m, 2H), 2.45 (s, 3H), 2.10-2.01 (m, 2H), 1.79-1.70 (m, 2H), 1.49-1.36 (m, 2H).

1-(2-Morpholin-4-ylmethyl-phenyl)-ethanone

General procedure A gave the title compound as yellow oil in 89% yield. Pure according to GCMS m/z: 219.

1-(3-Dimethylaminomethyl-4-methoxy-phenyl)-ethanone (5-Bromo-2-methoxy-benzyl)-dimethyl-amine (29 mmol), Butoxy-ethene (100 mmol), Palladium acetate (0.9 mmol), 1,3-Bis(diphenylphosphino)propane (1.8 mmol), and potassium carbonate were suspended in DMF (50 ml) and H$_2$O under argon. Heated at 80° C. overnight. Poured into hydrochloric acid (2 M) and stirred for 1 hour. The mixture was adjusted to basic pH and extracted with CH$_2$Cl$_2$. The organic phase was evaporated on celite and the residue was purified by flash chromatography to give the title product as orange oil in 42% yield. $^1$H-NMR (CDCl$_3$) δ 7.90 (s, 1H), 7.88 (dd, 1H), 6.89 (d, 1H), 3.88 (s, 3H), 3.44 (s, 2H), 2.55 (s, 3H), 2.25 (s, 6H).

1-[4-Hydroxy-3-(4-methyl-piperazin-1-ylmethyl)-phenyl]-ethanone

A solution of formaldehyde (37% w/w, 8.2 mL) was added to a solution of 4'-Hydroxy acetophenone (100 mmol), and N-methylpiperazine (110 mmol) in EtOH. Heated at reflux overnight. The solvent was evaporated on celite and the residue was purified by flash chromatography and crystallized from heptane to give the title product as white needles in 55% yield. $^1$H-NMR (DMSO-d$_6$) δ 7.76 (dd, 1H), 7.74 (s, 1H), 6.81 (d, 1H), 3.69 (s, 2H), 2.47 (br, 4H), 2.46 (s, 3H), 2.35 (br, 4H), 2.17 (s, 3H).

1-(2-Pyrrolidin-1-ylmethyl-phenyl)-ethanone

General procedure A gave the title product as colourless oil in 55% yield. $^1$H-NMR (DMSO-d$_6$) δ 7.49 (d, 1H), 7.40 (dd, 2H), 7.34-7.29 (m, 1H), 3.71 (s, 2H), 2.44 (s, 3H), 2.39-2.33 (m, 4H), 1.67-1.63 (m, 4H).

1-(3-Dimethylaminomethyl-phenyl)-ethanone

General procedure A gave the title product as yellow oil in 89% yield. $^1$H-NMR (CDCl$_3$) δ 7.89 (s, 1H), 7.85 (d, 1H), 7.52 (d, 1H), 7.42 (t, 1H), 3.47 (s, 2H), 2.61 (s, 3H), 2.25 (s, 6H).

1-[4-(2-Dimethylamino-ethylamino)-phenyl]-ethanone

General procedure B gave the title product as brown oil in 86% yield. $^1$H-NMR (CDCl$_3$) δ 7.76 (d, 2H), 6.50 (d, 2H), 4.90 (bs, 1H), 3.13 (q, 2H), 2.50 (t, 2H), 2.43 (s, 3H), 2.19 (s, 6H).

1-[3-(2-Dimethylamino-ethoxy)-phenyl]-ethanone

General procedure C gave the title product as brown oil in 26% yield. $^1$H-NMR (CDCl$_3$) δ 7.45-7.39 (m, 2H), 7.26 (t, 1H), 7.03 (ddd, 1H), 4.04.(t; 2H), 2.69 (t, 2H), 2.49 (s, 3H), 2.28 (s, 9H).

1-[2-Fluoro-4-(tetrahydro-pyran-2-yloxy)-phenyl]-ethanone

A solution of 1-(2-fluoro-4-hydroxy-phenyl)-ethanone (130 mmol), 3,4-dihydro-2H-pyran (260 mmol) and a catalytic amount of pyridinium p-toluenesulfonate in CH$_2$Cl$_2$ (200 mL) was left overnight at room temperature. The organic phase was washed with 1 N NaOH (aq) (1×50 mL) and dried (K$_2$CO$_3$). Evaporation in vacuo gave a brown oil, that was purified by vacuum distillation. The desired product was isolated as clear oil in 74% yield: bp: 130-140 ° C./0.05 mbar. $^1$H-NMR (CDCl$_3$) δ 7.86 (t, 1H), 6.87 (dd, 1H), 6.82 (dd, 1H), 5.49 (t, 1H), 3.86-3.78 (m, 1H), 3.67-3.61 (m, 1H), 2.59 (d, 3H), 1.97-1.60 (m, 6H).

1-[2-(4-Methyl-piperazin-1-yl)-4-(tetrahydro-pyran-2-yloxy)-phenyl]-ethanone General procedure O gave the title compound as an yellow oil in 66% yield. $^1$H-NMR (CDCl$_3$) δ 7.36 (d, 1H), 6.72-6.67 (m, 2H), 5.55 (t, 1H), 3.75-3.71 (m, 1H), 3.59-3.55 (m, 1H), 2.91 (t, 4H), 2.54 (s, 3H), 2.53-2.45 (m, 4H), 2.23 (s, 3H), 1.85-1.53 (m, 6H).

1-[3-(2-Dimethylamino-ethylamino)-phenyl]ethanone

General procedure B gave the title compound as yellow oil in 73% yield. $^1$H-NMR (CDCl$_3$) δ 7.28-7.18 (m, 3H), 6.85-6.78 (m, 1H), 4.45 (s, br, 1H), 4.10-3.23 (m, 2H), 2.59-2.52 (m, 5H), 2.25 (s, 6H).

1-[2-(2-Dimethylamino-ethylamino)-phenyl]ethanone

General procedure O gave the title compound as yellow oil in 58% yield.

1-{2-[(2-Dimethylamino-ethyl)-methyl-amino]-phenyl}ethanone

General procedure O gave the title compound as yellow oil in 93% yield. $^1$H-NMR (CDCl$_3$) δ 7.42-7.32 (m, 2H), 7.07 (d, 1H), 7.70-6.93 (td, 1H), 3.17 (t, 2H), 2.80 (s, 3H), 2.61 (s, 3H), 2.49-2.42 (m, 2H), 2.20 (s, 6H).

N-(3-Acetyl-phenyl)-2-dimethylamino-acetamide

A solution of 3'-amino-acetophenone (25 mmol) in THF (100 mL) was added chloroacyl chloride (30 mmol). The mixture was stirred for 30 min, poured into ice cold 2M NaOH (aq) and extracted with Et$_2$O. The organic phase was dried and the solvent was removed under reduced pressure giving the pure product. A solution of the product (10 mmol) and triethyl amine (30 mmol) in ethanol was added amine (20 mmol) and the mixture was refluxed for 4 hours. Ethanol was removed under reduced pressure and the product was dissolved in EtOAc and washed with 2M NaOH (aq). EtOAc was removed under reduced pressure giving the product as pure brown oil in 85% yield. $^1$H-NMR (CDCl$_3$) δ 9.31 (s, 1H), 8.05 (m, 2H), 7.72 (dt,1H), 7.46 (t, 1H), 3.11 (s, 2H), 2.62 (s, 3H), 2.41 (s,.6H).

1-[4-(2-Dimethylamino-ethoxy)-2,fluoro-phenyl]-ethanone

General procedure C gave the title compound as a brown oil in 14% yield. $^1$H-NMR (CDCl$_3$) δ 7.88 (t, 1H), 6.77 (dd, 1H), 6.64 (dd, 1H), 4.12 (t, 2H), 2.77 (t, 2H), 2.60 (d, 3H), 2.35 (s, 6H).

1-[4-(2-Dimethylaminoethoxy)-2-(4-methyl-piperazin-1-yl)-phenyl]-ethanone

General procedure O gave the title compound as an yellow oil in 17% yield. $^1$H-NMR (CDCl$_3$) δ 7.49 (d, 1H), 6.60 (d, 1H), 6.56 (dd, 1H), 4.08 (t, 2H), 3.02 (t, 4H), 2.73 (t, 2H), 2.62 (s, 3H), 2.35 (s, 3H), 2.34 (s, 6H).

Benzaldehydes

4-Hydroxy-2'-methyl-biphenyl-3-carbaldehyde

General procedure G gave the title compound as brown crystals in 61% yield. $^1$H-NMR (CDCl$_3$) δ 11.04 (s, 1H), 9.95 (d, 1H), 7.54-7.52 (m, 2H), 7.32-7.24 (m, 5H), 7.07 (dd, 1H), 2.30 (s, 3H).

3-[1,3]Dioxan-2-yl-2'-methyl-biphenyl-4-ol

A solution of 4-hydroxy-2'-methyl-biphenyl-3-carbaldehyde (18.8 mmol) in toluene (100 mL) was added 1,3-dihydroxypropane (65.7 mmol) and p-toluenesulfonic acid (cat) and heated at reflux overnight in a Dean-Stark set-up. The reaction was cooled and washed with a solution of Na$_2$CO$_3$ (aq, 1 M). Evaporation in vacuo gave the title product as brown oil in 89% yield. $^1$H-NMR (CDCl$_3$) δ 9.61 (bs, 1H), 7.34-7.10 (m, 6H), 6.87 (d, 1H), 5.77 (s,1H), 4.13-4.07 (m, 2H), 3.95-3.86 (m, 2H), 2.20 (s, 3H), 2.18-1.96 (m, 1H), 1.40 (d, 1H).

2-[4-(2-Chloro-ethoxy)-2'-methyl-biphenyl-3-yl]-[1,3]dioxane

General procedure L gave the title compound as colourless crystals in 92% yield. $^1$H-NMR (CDCl$_3$) δ 7.54 (d, 1H), 7.20-7.13 (m, 5H), 6.83 (d, 1H), 5.88 (s, 1H), 4.24 (dd, 2H), 4.17 (dd, 2H), 3.96 (t, 2H), 3.80 (t, 2H), 2.18-2.12 (m, 4H), 1.35 (d, 1H).

2-[4-(4-Bromo-butoxy)-2'-methyl-biphenyl-3-yl]-[1,3]dioxane

General procedure L gave the title compound as colourless crystals in 61% yield. $^1$H-NMR (CDCl$_3$) 65 7.61 (d, 1H), 7.28-7.21 (m, 5H), 6.91 (d, 1H1), 5.92 (s, 1H), 4.27 (dd, 2H), 4.12-4.00 (m, 4H), 3.58 (t; 2H), 2.28-2.01 (m, 8H), 1.45 (d, 1H).

2-[4-(5-Bromo-pentyloxy)-2'-methyl-biphenyl-3-yl]-[1,3]dioxane

General procedure L gave the title compound as colourless oil in 48% yield. $^1$-NMR (CDCl$_3$) δ 7.61 (d, 1H), 7.28-7.20 (m, 5H), 6.91 (d, 1H), 5.93 (s, 1H), 4.27 (dd, 2H), 4.09-4.00 (m, 4H), 3.50 (t, 2H), 2.27-2.22 (m, 4H), 2.06-1.69 (m, 6H), 1.44 (d, 1H).

4-[2-(tert-Butyl-methyl-amino)-ethoxy]-2'-methyl-biphenyl-3-carbaldehyde

General procedure K gave the title compound as colourless crystals in 68% yield. $^1$H-NMR (CDCl$_3$) δ 10.49 (s, 1H), 7.72 (d, 1H), 7.42 (dd, 1H), 7.18-7.13 (m, 4H), 6.97 (d, 1H), 4.09 (t, 2H), 2.81 (t, 2H), 2.29 (s, 3H), 2.18 (s, 3H), 1.05 (s, 9H).

2'-Methyl-4-(2-pyrrolidin-1-yl-ethoxy)-biphenyl-3-carbaldehyde

General procedure K gave the title compound as yellow crystals in 75% yield. $^1$H-NMR (CDCl$_3$) δ 10.35 (s, 1H), 7.61 (d, 1H), 7.32 (dd, 1H), 7.08-6.99 (m, 4H), 6.87 (d, 1H), 4.22 (bs, 2H), 2.76 (bs, 2H), 2.23 (bs, 2H), 2.06 (s, 3H), 0.98 (bs, 2H).

4-(2-Diethylamino-ethoxy)-2'-methyl-biphenyl-3-carbaldehyde

General procedure K gave the title compound as an yellow in 75°/% yield. $^1$H-NMR (CDCl$_3$) δ 10.35 (s, 1H), 7.63 (d, 1H), 7.33 (dd, 1H), 7.09-7.01 (m, 4H), 6.88 (d, 1H), 4.10 (t, 2H), 2.86 (t, 2H), 2.56 (bs, 4H), 2.08 (s, 3H), 0.97 (t, 6H).

4-[4-(tert-Butyl-methyl-amino)-butoxy]-2'-methyl-biphenyl-3-carbaldehyde

General procedure K gave the title compound as an yellow oil in 37% yield. $^1$H-NMR (CDCl$_3$) δ 10.49 (s, 1H), 7.73 (d, 1H), 7.43 (dd, 1H), 7.19-7.12 (m, 4H), 6.97 (d, 1H), 4.09 (t, 2H), 2.37 (t, 2H), 2.19 (s, 3H), 2.15 (s, 3H), 1.88-1.79 (m, 2H), 1.64-1.54 (m, 2H), 1.00 (s, 9H).

4-(4-Diethylamino-butoxy)-2'-methyl-biphenyl-3-carbaldehyde

General procedure K gave the title compound as an yellow oil in 35% yield. $^1$H-NMR (CDCl$_3$) δ 10.60 (s, 1H), 7.84 (d, 1H), 7.54 (dd, 1H), 7.30-7.22 (m, 4H), 8.07 (d, 1H), 4.20 (t, 2h), 2.62-2.53 (m, 6H), 2.30 (s, 3H), 1.96-1.89 (m, 2H), 1.75-1.69 (m, 2H), 1.07 (t, 6H).

2'-Methyl-4-(4-pyrrolidin-1-yl-butoxy)-biphenyl-3-carbaldehyde

General procedure K gave the title compound as an yellow oil in 52% yield. $^1$H-NMR (CDCl$_3$) δ 10.35 (s, 1H), 7.60 (d, 1H), 7.29 (dd, 1H), 7.06-6.98 (m, 4H), 6.83 (d, 1H), 3.96 (t, 2H), 2.36-2.29 (m, 6H), 2.06 (s, 3H), 1.76-1.71 (m, 2H), 1.61-1.52 (m, 6H).

2'-Methyl-4-(4-methylamino-butoxy)-biphenyl-3-carbaldehyde

General procedure K gave the title compound as an yellow oil in 19% yield. $^1$H-NMR (CDCl$_3$) δ 10.47 (s, 1H), 7.73 (d, 1H), 7.43 (dd, 1H), 7.19-7.13 (m, 4H), 6.68 (d, 1H), 4.09 (t, 2H), 2.63 (t, 2H), 2.40 (s, 3H), 2.19 (s, 3H), 1.90-1.83 (m, 2H), 1.69-1.63 (m, 2H).

4-[5-(tert-Butyl-methyl-amino)-pentyloxy]-2'-methyl-biphenyl-3-carbaldehyde

General procedure K gave the title compound as an yellow oil in 37% yield. $^1$H-NMR (CDCl$_3$) δ 10.49 (s, 1H), 7.73 (d, 1H), 7.43 (dd, 1H), 7.19-7.13 (m, 4H), 6.96 (d, 1H), 4.07 (t, 2H), 2.32-2.31 (m, 2H), 2.19 (s, 3H), 2.15 (s, 3H), 1.84-1.81 (m, 4H), 1.50-1.45 (m, 4H), 0.99 (s, 9H).

4-(3-Dimethylamino-propoxy)-2'-methyl-biphenyl-3-carbaldehyde

General procedure F gave the title compound as an yellow oil in 57% yield. $^1$H-NMR (CDCl$_3$) δ 10.57 (s, 1H), 7.82 (d, 1H), 7.52 (dd, 1H), 7.28-7.21 (m, 4H), 7.08 (d, 1H), 4.23 (t, 2H), 2.55 (t, 2H), 2.38-2.24 (m, 5H).

5-Bromo-2-(2-dimethylamino-ethoxy)-benzaldehyde

General procedure E gave the title compound as a yellow oil in 65% yield. $^1$H-NMR (CDCl$_3$) δ 10.43 (s, 1H), 7.94 (d, 1H), 7.63 (dd, 1H), 6.92 (d, 1H), 4.19 (t, 2H), 2.81 (t, 2H), 2.37 (s, 6H).

4-(2-Dimethylamino-ethoxy)-biphenyl-3-carbaldehyde

General procedure G gave the title compound as yellow, crystals in $^{57}$% yield. $^1$H-NMR (CDCl$_3$) δ 10.48 (s, 1H), 8.01 (d, 1H), 7.71 (dd, 1H), 7.49 (d, 1H), 7.36 (t, 2H), 7.26 (t, 1H), 7.00 (d, 1H), 4.18 (t, 2H), 2.77 (t, 2H), 2.31 (s, 6H).

4-(2-Dimethylamino-ethoxy)-2'-methyl-biphenyl-3-carbaldehyde

General procedure G gave the title compound as white crystals in 79% yield. $^1$H-NMR (CDCl$_3$) δ 10.56 (s, 1H), 7.82 (d, 1H), 7.51 (dd, 1H), 7.28-7.16 (m, 4H), 7.05 (d, 1H), 4.25 (t, 2H), 2.84 (t, 2H), 2.38 (s, 6H), 2.26 (s, 3H).

4-(2-Dimethylamino-ethoxy)-2'-methoxy-biphenyl-3-carbaldehyde

General procedure G gave the title compound as light yellow crystals in 78% yield. $^1$H-NMR (DMSO-d$_6$) δ 10.40 (s, 1H), 7.80-7.72 (m, 2H), 7.38-7.25 (m, 3H), 7.11 (d, 1H), 7.03 (t, 1H), 4.25 (t, 2H), 3.76 (s, 3H), 2.72 (t, 2H), 2.25 (s, 6H).

4-(2-Dimethylamino-ethoxy)-[1,1';4',1'']terphenyl-3-carbaldehyde

General procedure G gave the title compound as light yellow crystals in 31% yield. $^1$H-NMR (CDCl$_3$) δ 10.49 (s, 1H), 8.06 (d, 1H), 7.76 (dd, 1H), 7.59-7.55 (m, 6H), 7.39 (dd, 2H), 7.31 (dd, 1H), 7.02 (d, 1H), 4.18 (t, 2H), 2.77 (t, 2H), 2.31 (s, 6H).

4-(2-Dimethylaminoethoxy)-2'-trifluoromethoxy-biphenyl-3-carbaldehyde

General procedure G gave the title product as yellow oil in 40% yield. $^1$H-NMR (DMSO-d$_6$) δ 10.41 (s, 3H), 7.78-7.74 (m, 2H), 7.58-7.45 (m, 4H), 7.40-7.36 (m, 1H), 4.28 (t, 2H), 2.72 (t, 2H), 2.24 (s, 6H).

2'-tert-Butoxymethyl-4-(2-dimethylamino-ethoxy)-biphenyl-3-carbaldehyde

General procedure G gave the title product as yellow oil in 65% yield. $^1$H-NMR (DMSO-d$_6$) δ 10.44 (s, 1H), 7.83 (d, 1H), 7,70 (dd, 1H), 7.46-7.41 (m, 1H), 7.39-7.32 (m, 3H), 7.29-7.23 (m, 1H), 4.27 (t, 2H), 4.18 (s, 2H), 2.72 (t, 2H), 2.25 (s, 6H), 1.13 (s, 9H).

4-(2-Dimethylamino-ethoxy)-2',5'-dimethoxy-biphenyl-3-carbaldehyde

General procedure G gave the title product as yellow oil in 72% yield. $^1$H-NMR (DMSO-d$_6$) δ 10.40 (s, 1H), 7.79-7.75 (m, 2H), 7.29 (d, 1H), 7.04 (d, 1H), 6.89 (dd, 1H), 6.86 (d, 1H), 4.26 (t, 2H), 3.74 (s, 3H), 3.70 (s, 3H), 2.72 (t, 2H), 2.24 (s, 6H).

4-(2-Dimethylamino-ethoxy)-2',4'-dimethoxy-biphenyl-3carbaldehyde

General procedure G gave the title product as orange oil in 53%, yield. $^1$H-NMR (DMSO-d$_6$) δ 10.40 (s, 1H), 7.73 (s, 3H), 7.71 (dd, 1H), 7.27 (dd, 1H), 7.21 (d, 1H), 6.66 (d, 1H), 6.60 (dd, 1H), 4.25 (t, 2H), 3.80 (s, 3H), 3.76 (s, 3H), 2.71 (t, 2H), 2.24 (s, 6H).

4-(2-Dimethylamino-ethoxy)-2',4',6'-trimethyl-biphenyl-3-carbaldehyde

General procedure G gave the title product as brown crystals in 45% yield. $^1$H-NMR (DMSO-d$_6$) δ 10.41 (s, 1H), 7.40 (dd, 1H), 7.37 (d, 1H), 7.32 (d, 1H), 6.93 (s, 2H), 4.26 (t, 2H), 2.73 (t, 2H), 2.25 (s, 9H), 1.92 (s, 6H).

4-(2-Dimethylamino-ethoxy)-2'-methoxymethyl-biphenyl-3-carbaldehyde

General procedure G gave the title product as yellow oil in 51% yield. $^1$H-NMR (DMSO-d$_6$) δ 10.43 (s, 1H), 7.69 (s, 1H), 7.68 (dd, 1H), 7.51-7.46 (m, 1H), 7.41-7.26 (m, 4H), 4.27 (t, 2H), 4.23 (s, 2H), 3.23 (s, 3H), 2.73 (t, 2H), 2.24 (s, 6H).

4-(2-Dimethylamino-ethoxy)-2',6'-dimethoxy-biphenyl-3-carbaldehyde

General procedure G gave the title product as yellow oil in 13% yield. $^1$H-NMR (DMSO-d$_6$) δ 10.39 (s, 1H), 7.66-7.46 (m, 4H), 7.33-7.22 (m, 1H), 6.74 (d, 1H), 4.24 (t, 2H), 3.66 (s, 6H), 2.72 (t, 21H), 2.25 (s, 6H).

2'-Chloro-4-(2-dimethylamino-ethoxy)-biphenyl-3-carbaldehyde

General procedure G gave the title product as yellow oil in 45% yield. $^1$H-NMR (DMSO-$d_6$) δ 10.41 (s, 1H), 7.72 (s, 1H), 7.71 (dd, 1H), 7.56-7.52 (m, 1H), 7.42-7.32 (m, 4H), 4.26 (t, 2H), 2.72 (t, 2H), 2.23 (s, 6H).

2'-Bromo-4-(2-dimethylamino-ethoxy)-biphenyl-3-carbaldehyde

General procedure G, using 4-(2-dimethylamino-ethoxy)-3-formyl-benzeneboronic acid and 1-bromo-2-iodo-benzene gave the title product as yellow oil in 68% yield. $^1$H-NMR (CDCl$_3$) δ 10.51 (s, 1H), 7.90 (d, 1H), 7.70-7.65 (m, 2H), 7.41-7.20 (m, 3H), 7.09 (d, 1H), 4.40 (t, 2H), 3.04 (bs, 2H), 2.56 (s, 6H).

4-(2-Dimethylamino-ethoxy)-2'-methylsulfanyl-biphenyl-3-carbaldehyde

General procedure G gave the title product as yellow oil in 31% yield. $^1$H-NMR (DMSO-$d_6$) δ 10.41 (s, 1H), 7.66 (s, 1H), 7.65 (dd, 1H), 7.42-7.31 (m, 3H), 7.23-7.19 (m, 2H), 4.27 (t, 2H), 2.73 (t, 2H), 2.37 (s, 3H), 2.25 (s, 6H).

4-(2-Dimethylamino-ethoxy)-2'-trifluoromethyl-biphenyl-3-carbaldehyde

General procedure G gave the title product as yellow oil in 69% yield. $^1$H-NMR (DMSO-$d_6$) δ 10.41 (s, 1H), 7.82 (d, 1H), 7.72 (t, 1H), 7.65-7.56 (m, 3H), 7.41 (d, 1H), 7.34 (d, 1H), 4.27 (t, 2H), 2.73 (t, 2H), 2.24 (s, 6H).

4-(2-Dimethylamino-ethoxy)-2'-hydroxy-biphenyl-3-carbaldehyde

General procedure G gave the title product as brown oil in quantitative yield. $^1$H-NMR (DMSO-$d_6$) δ 10.42 (s, 1H), 9.63 (br, 1H), 7.89 (d, 1H), 7.83 (dd, 1H), 7.29 (d, 1H), 7.26 (dd, 1H), 7.16 (td, 1H), 6.94 (dd, 1H), 6.87 (td, 1H), 4.26 (t, 2H), 2.73 (t, 2H), 2.25 (s, 6H).

4-(2-Dimethylamino-ethoxy)-2'-ethyl-biphenyl-3-carbaldehyde

General procedure G gave the title product as brown oil in quantitative yield. $^1$H-NMR (DMSO-$d_6$) 10.42 (s, 1H), 7.61 (dd, 1H), 7.56 (d, 1H), 7.35-7.31 (m, 3H), 7.27-7.21 (m, 1H), 7.15 (d, 1H), 4.28 (t, 2H), 2.75 (t, 2H), 2.53 (q, 2H), 2.27 (s, 6H), 1.03 (t, 3H).

[2-(2',6'-Dichloro-biphenyl-4-yloxy)-ethyl]-dimethyl-amine

General procedure M gave the title product as brown oil in 90% yield. $^1$H-NMR (DMSO-$d_6$) δ 7.57 (d, 1H), 7.54 (s, 1H), 7.42-7.37 (m, 1H), 7.17 (d, 2H), 7.03 (d, 2H), 4.10 (t, 2H), 2.65 (t, 2H).

2',6'-Dichloro-4-(2-dimethylamino-ethoxy)-biphenyl-3-carbaldehyde

General procedure J gave the title product as brown crystals in 88% yield. 1H-NMR (CDCl$_3$), δ 10.61 (s, 1H), 7.83 (d, 1H), 7.52 (dd, 1H), 7.47 (d, 1H), 7.44 (s, 1H), 7.33-7.28 (m, 1H), 7.15 (d, 1H), 4.33 (t, 2H), 2.91 (t, 2H), 2.45 (s, 6H).

2',6'-Difluoro-biphenyl-4-ol

General procedure G using 4-Hydroxyphenylboronic acid O-tetrahydropyranyl ether and 2-Bromo-1,3-difluoro-benzene, followed by subsequent deprotection gave the title product as beige crystals in quantitative yield. $^1$H-NMR (DMSO-$d_6$) δ 9.72 (s, 1H), 7.45-7.35 (m, 1H), 7.27-7.22 (m, 2H), 7.20-7.13 (m, 2H), 6.87 (dt, 2H).

[2-(2',6'-Difluoro-biphenyl-4-yloxy)-ethyl]-dimethyl-amine

General procedure M gave the title product as dark brown crystals in quantitative yield. $^1$H-NMR (DMSO-$d_6$) δ 7.48-7.40 (m, 1H), 7.39-7.33 (m, 2H), 7.22-7.15 (m, 2H), 7.05 (dt, 2H), 4.10 (t, 2H), 2.64 (t, 2H), 2.22 (s, 6H).

4-(2-Dimethylamino-ethoxy)-2',6'-difluoro-biphenyl-3-carbaldehyde

General procedure J gave the title product as brown oil in 57% yield. $^1$H-NMR (DMSO-$d_6$) δ 10.41 (s, 1H), 7.77-7.72 (m, 2H), 7.66-7.37 (m, 2H), 7.23 (t, 2H), 4.29 (t, 2H), 2.73 (t, 2H), 2.25 (s, 6H).

4-(4-Dimethylamino-butoxy)-2'-methyl-biphenyl-3-carbaldehyde

General procedure K gave the title product as orange oil in 19% yield. $^1$H-NMR (DMSO-$d_6$) δ 10.43 (s, 1H), 7.64 (dd, 1H), 7.59 (d, 1H), 7.32-7.17 (m, 5H), 4.21 (t, 2H), 2.27 (t, 2H), 2.22 (s, 3H), 2.13 (s, 6H), 1.82 (p, 2H), 1.60 (p, 2H).

4-(2-Dimethylamino-ethoxy)-3',5'-dimethyl-biphenyl-3-carbaldehyde

General procedure G gave the title compound as colourless crystals in 81% yield. $^1$H-NMR (DMSO-$d_6$) δ 10.41 (s, 1H), 7.94-7.89 (m, 2H), 7.33 (d, 1H), 7.24 (bs, 2H), 6.98 (bs, 1H), 4.25 (t, 2H), 2.71 (t, 2H), 2.32 (s, 6H), 2.24 (s, 6H).

5-tert-Butyl-2-(2-dimethylamino-ethoxy)-benzaldehyde

General procedure E gave the title product as yellow oil in 93% yield. $^1$H-NMR (CDCl$_3$) δ 10.50 (s, 1H), 7.85 (d, 1H), 7.57 (dd, 1H), 6.93 (d, 1H), 4.18 (t, 2H), 2.79 (t, 2H), 2.36 (s, 6H), 1.31 (s, 9H).

2-(2-Dimethylamino-ethoxy)-5-methyl-benzaldehyde

General procedure E gave the title product as yellow oil in 95% yield. $^1$H-NMR (CDCl$_3$) δ 10.48 (s, 1H), 7.63 (d, 1H), 7.34 (dd, 1H), 6.89 (d, 1H), 4.16 (t, 2H), 2.79 (t, 2H), 2.35 (s, 6H), 2.31 (s, 3H).

3,5-Di-tert-butyl-2-(2-dimethylamino-ethoxy)-benzaldehyde

General procedure E gave the title product as yellow oil in 35% yield. $^1$H-NMR (CDCl$_3$) δ 10.39 (s, 1H), 7.72 (d, 1H), 7.63 (d, 1H), 4.05 (t, 2H), 2.83 (t, 2H), 1.45 (s, 6H), 1.33 (s, 9h), 1.29 (s, 9H).

5-tert-Butyl-2-(3-dimethylaminopropoxy)-benzaldehyde

General procedure F gave the title product as yellow oil in 56% yield. $^1$H-NMR (CDCl$_3$) δ 10.52 (s, 1H), 7.86 (d, 1H), 7.58 (dd, 1H), 6.96 (d, 1H), 4.15 (t, 2H), 2.49 (t, 2H), 2.27 (s, 6H), 2.02 (hep, 2H), 1.33 (s, 9H).

2-(2-Dimethylamino-ethoxy)-5-propyl-4-(tetrahydro-pyran-2-yloxy)-benzaldehyde General procedure E gave the title compound as brown crystals in 15% yield. $^1$H-NMR (CDCl$_3$) δ 10.36 (s, 1H), 7.65 (s, 1H), 6.78 (s, 1H), 5.56 (s, 1H), 4.24-4.12 (m, 2H), 3.88-3.64 (m, 2H), 2.81 (t, 2H), 2.61-2.55 (m, 2H), 2.38 (s, 6H), 2.05-1.57 (m, 8H), 0.96 (t, 3H).

2-Hydroxy-5-(tetrahydro-pyran-2-yloxy)-benzaldehyde

A solution of 2,5-dihydroxy-benzaldehyde (152 mmol), 3,4-dihydro-2H-pyran (167 mmol) and a catalytic amount of pyridinium p-toluenesulfonate in CH$_2$Cl$_2$ (480 mL) was left overnight at room temperature. The organic phase was washed with 1 N Na7CO$_3$ (aq) (3×100 mL) and dried (Na$_2$SO$_4$). Evaporation in vacuo gave the desired product as brown crystals that was used without further purification. $^1$H-NMR (CDCl$_3$) δ 10.72 (s, 1H), 9.88 (s, 1H), 7.32-7.29 (m, 2H), 6.96 (d, 1H), 5.38 (bs, 1H), 3.99-3.91 (m, 1H), 3.69-3.64 (m, 1H), 2.06-1.63 (m, 6H).

2-(2-Dimethylamino-ethoxy)-5-(tetrahydro-pyran-2-yloxy)-benzaldehyde

General procedure E gave the title compound as an yellow oil in 86% yield. $^1$H-NMR (CDCl$_3$) δ 10.46 (s, 1H), 7.50 (d, 1H), 7.27-7.23 (m, 1H), 6.93 (d, 1H), 5.35 (t, 1H), 4.15 (t, 2H), 3.94-3.86 (m, 1H), 3.63-3.57 (m, 2H), 2.77 (t, 2H), 2.35 (s, 6H), 2.01-1.55 (m, 6H).

5-(1,1-Dimethyl-allyl)-2-hydroxy-benzaldehyde

A solution of boron trichloride (1M in CH$_2$Cl$_2$, 39.7 mmol) was added dropwise under argon at −78° C. to a stirred solution of 5-(1,1-Dimethyl-allyl)-2-methoxy-benzaldehyde (13.2 mmol) in dry CH$_2$Cl$_2$ (120 ml). The dry ice—acetone bath was removed and reaction allowed warming to RT. Stirred at RT for 18 hours, before the reaction mixture was cooled to 0° C. and iced water (125 ml) slowly added. Extracted with CH$_2$Cl$_2$ (2×100 ml). The organic phases were washed with brine, dried (Na$_2$SO$_4$), filtered, and evaporated to black oil. Purified by flash chromatography (heptane:EtOAc) to give the title product as yellow oil in 56% yield. $^1$H-NMR (CDCl$_3$) δ 10.82 (s, 1H), 9.81 (s, 1H), 7.43 (d, 1H), 7.41 (s, 1H), 6.86 (d, 1H), 5.92 (dd, 1H), 5.02-4.96 (m, 2H), 1.34 (s, 6H).

5-(1,I-Dimethyl-allyl)-2-(2dimethylamino-ethoxy)-benzaldehyde

General procedure E gave the title product as yellow oil in 41%) yield. $^1$H-NMR (CDCl$_3$) δ 10.42 (s, 1H), 7.75 (d, 1H), 7.44 (dd, 1H), 6.85 (d, 1H), 5.96-5.86 (m, 1H),4.99-4.93 (m, 2H), 4.11 (t, 2H), 2.72 (t, 2H), 2.28 (s, 6H), 1.32 (s, 6H).

2'-Methyl-4-(5-pyrrolidin-1-yl-pentyloxy)-biphenyl-3-carbaldehyde,

General procedure K gave the title product as brown oil in 34% yield. $^1$H-NMR (CDCl$_3$) δ 10.48 (s, 1H), 7.73 (d, 1H), 7.43 (dd, 1H), 7.19-7.12 (m, 4H), 6.95 (d, 1H), 4.07 (t, 2H), 2.54-2.46 (m, 6H), 2.17 (s, 3H), 1.90-1.74 (m; 6H), 1.64-1.47 (m, 4H).

4-(2-Dimethylamino-ethoxy)-3-formyl-benzeneboronic acid

A stirred solution of [$^2$-($^4$-bromo-2-[1,3]dioxan-2-yl-phenoxy)-ethyl]-dimethyl-amine (15 mmol) in dry THF (100 mL) was cooled to −78° C. and added n-BuLi (16.5 mmol) dropwise. The reaction was left for 30 min at −78° C. and added triisopropyl borate (22.5 mmol). The reaction was heated to room temperature, was added 2M HCl (aq, 50 mL) and was left for an additional, hour. The mixture was added 1M Na$_2$CO$_3$ to neutral pH and was extracted with EtOAc. The organic phase was washed with water, dried (Na$_2$SO$_4$) and evaporated in vacuo. Addition of EtOAc afforded beige crystals that was filtered of and was used without further purification.

2-(2-Dimethylamino-ethoxy)-5-pyridin-3-yl-benzaldehyde

General procedure G using 4-(2-dimethylamino-ethoxy)-3-formyl-benzeneboronic acid and 3-bromo-pyridine gave the title product as yellow oil in 13% yield. $^1$H-NMR (CDCl$_3$) δ 10.46 (s, 1H), 8.76 (d, 1H), 8.52 (dd, 1H), 8.00 (d, 1H), 7.80 (dt, 1H), 7.72 (dd, 1H), 7.30 (ddd, 1H), 7.07 (d, 1H), 4.28 (t, 2H), 2.90 (t, 2H), 2.42 (s, 6H).

2-(2-Dimethylamino-ethoxy)-5-pyridin-2-yl-benzaldehyde

General procedure G using 4-(2-dimethylamino-ethoxy)-3-formyl-benzeneboronic acid and 2-bromo-pyridine gave the title product as yellow oil in 40% yield. $^1$H-NMR (CDCl$_3$) δ 10.47 (s, 1H), 8.60(dt, 1H), 8.34 (d, 1H), 8.26 (dd, 1H), 7.69-7.67 (m, 2H), 7.17-7.14 (m, 1H), 7.05 (d, 1H), 4.24 (t, 2H), 2.83 (t, 2H), 2.36 (s, 6H).

4-(2-Dimethylamino-ethoxy)-3'-methyl-biphenyl-3-carbaldehyde

General procedure G gave the title product as orange oil in 66% yield. $^1$H-NMR (CDCl$_3$) δ 10.27 (s, 1H), 7.80 (dd, 1H), 7.76 (d, 1H), 7.32-7.17 (m, 4H), 7.02 (d, 1H), 4.13 (t, 2H), 2.57 (t, 2H), 2.23 (s, 3H), 2.10 (s, 6H).

4-(2-Dimethylamino-ethoxy)-4'-methyl-biphenyl-3-carbaldehyde

General procedure G gave the title product as yellow oil in 58% yield. $^1$H-NMR (CDCl$_3$) δ 10.53 (s, 1H), 8.06 (d, 1H), 7.77 (dd, 1H), 7.47 (d, 2H), 7.24 (d, 2H), 7.06 (d, 1H), 4.28 (t, 2H), 2.88 (t, 2H), 2.42 (s, 6H), 2.38 (s, 3H).

3-(2-Dimethylamino-ethoxy)-2'-methyl-biphenyl-4-carbaldehyde

A solution of 2,4-dihydroxybenzaldehyde (27 mmol) in methylene chloride (10 ml) and pyridine (30 mmol) was slowly added trifluoromethanesulfonic anhydride (32 mmol)

keeping the temperature below 5° C. After 10 min the mixture was washed with water and the organic phase was concentrated under reduced pressure. The crude brown oil (5 g), ortho-tolylboronic acid (20.4 mmol), sodium carbonate (55.5 mmol) and dichlorobis(triphenylphosphine)-palladium (II) (3 mol %) was dissolved in DME (50 ml) and water (20 ml). The mixture was refluxed for 17 h under Argon, cooled to room temperature and extracted with ethyl acetate. The crude black oil (4.6 g) was dissolved in DMF (75 ml) and sodium hydride (60% in oil, 22.5 mmol) was slowly added. A solution of 2-dimethylamino ethylchloride (22.5 mmol) in toluene (120 ml) was added and the mixture was heated at 80° C. for 3 days. The mixture was washed with saturated sodium bicarbonate, concentrated under reduced pressure and purified by chromatography. The resulting yellow oil was washed with hot heptane giving the product as relative pure oil (GC-MS). $^1$H-NMR (DMSO-$d_6$) δ 10.41 (s, 1H), 7.74 (d, 2H), 7.66-7.55 (m, 1H), 7.36-6.79 (m, 4H), 4.27 (t, 2H), 2.70 (t, 2H), 2.27 (s, 3H), 2.23 (s, 6H).

5-(2-Dimethylamino-ethoxy)-biphenyl-3-carbaldehyde

A solution of 3,5-dihydroxybenzaldehyde (14.4 mmol) and pyridine (114 mmol) in methylene chloride (20 ml) was slowly added trifluoromethanesulfonic anhydride (36.2 mmol) keeping the temperature below 5° C. After 10 min the mixture was washed with water and the organic phase was concentrated under reduced pressure. The crude brown crystals (6.4 g—product and pyridine −1:1), phenylboronic acid (13.2 mmol), sodium carbonate (39.6 mmol) and dichlorobis (triphenylphosphine)-palladium (II). (3 mol %) was dissolved in DME (40 ml) and water (20 ml). The mixture was refluxed for 17 h under Argon, cooled to room temperature and extracted with ethyl acetate. Purification by chromatography yielded 5-Hydroxy-biphenyl-3-carbaldehyde as white crystals (7 mmol). $^1$H-NMR (DMSO): δ 10.11 (s, 1H), 10.00 (s, 1H), 7.69-7.66 (m, 3H), 7.51-7.46 (bt, 2H), 7.41 (m, 1H), 7.36 (t, 1H), 7.26 (t, 1H).

The product (7 mmol) and 2-dimethylamino ethylchloride, hydrochloride (14.1 mmol) was dissolved in DMF (40 ml), and sodium hydride (60% in oil, 22.6 mmol) was slowly added. The mixture was heated at 100° C. for 18 hours, partitioned between methylene chloride and saturated sodium bicarbonate, and concentrated under reduced pressure. Flash chromatography gave a crude yellow oil consisting of 5-(2-Dimethylamino-ethoxy)-biphenyl-3-carbaldehyde (~1.7 mmol) and DMF (1:10 mixture). 1H-NMR (DMSO-$d_6$): δ 10.05 (s, 1H), 7.81-7.75 (m, 3H), 7.55-7.42 (m, 5H), 4.22 (t, 2H), 2.67 (t, 2H), 2.24 (s, 6H).

Chalcone Synthesis

C001: (E)-3-[2-(2-Dimethylamino-ethoxy)-phenyl]-1-(2,3,4-trimethoxy-phenyl)-propenone General procedure I gave the title product as yellow oil in 7% yield. $^1$H-NMR (CDCl$_3$) δ 8.04 (d, 1H), 7,66 (dd, 1H), 7.54 (d, 1H), 7.47 (d, 1H), 7.38 (dd, 1H), 7.00 (t, 1H), 6.94 (d, 1H), 6.77 (d, 1H), 4.16 (t, 2H), 3.94 (s, 3H), 3.93 (s, 3H), 3.92 (s, 3H), 2.83 (t, 2H), 2.35 (s, 6H).

C002: (E)-3-[2-(2-Dimethylamino-ethoxy)-5-methyl-phenyl]-1-(2-fluoro4-methoxy-phenyl)-propenone General procedure H gave the fumarate of the title product as colourless crystals in 19% yield. $^1$H-NMR (DMSO-$d_6$) δ 7.63 (dd, 1H), 7,57 (dd, 1H), 7.36-7.30 (m, 2H), 7.00 (dd, 1H), 6.81-6.67 (m, 3H), 6.36 (s, 2H), 3.92 (t, 2H), 3.63 (s, 3H), 2.56 (t 2H), 2.06 (s, 6H), 2.04 (s, 3H).

C003: (E)-3-[2-(2-Dimethylamino-ethoxy)-5-methyl-phenyl]-1-(2,3,4trimethoxy-phenyl)-propenone General procedure H gave the fumarate of the title product as yellow crystals in 16% yield. $^1$H-NMR (DMSO-$d_6$) δ 7.89 (d, 1H), 7,67 (d, 1H), 7.55 (d, 1H), 7.43 (d, 1H), 7.33 (dd, 1H), 7.13 (d, 1H), 7.05 (d, 1H), 6.71 (s, 2H), 4.28 (t, 2H), 3.99 (s, 3H), 3.93 (s, 3H), 3.91 (s, 3H), 2.93 (t, 2H), 2.40 (s, 6H), 2.39 (s, 3H).

C004: (E)-3-[5-tert-Butyl-2-(2-dimethylamino-ethoxy)-phenyl]-1-(2-fluoro-4-methoxy-phenyl)-propenone General procedure H gave the fumarate of the title product as yellow crystals in 39% yield. $^1$H-NMR (DMSO-$d_6$) δ 7.69 (dd, 1H), 7.61 (dd, 1H), 7.52 (dd, 1H), 7.44 (dd, 1H), 7.25 (dd, 1H), 6.86 (d, 1H), 6.81-6.72 (m, 2H), 6.40 (s, 2H), 3.99 (t, 2), 3.68 (s, 3H), 2.63 (t, 2H), 2.12 (s, 6H), 1.10 (s, 9H).

C005: (E)-3-[5-tert-Butyl-2-(2-dimethylamino-ethoxy)-phenyl]-1-(2,3,4-trimethoxy-phenyl)-propenone General procedure H gave the fumarate of the title product as yellow crystals in 20% yield. $^1$H-NMR (DMSO-$d_6$) δ 7.75 (d, 1H), 7.67 (d, 1H), 7.48 (d, 1H), 7.40 (dd, 1H), 7.29 (d, 1H), 7.01 (d, 1H), 6.90 (d, 1H), 6.57 (s, 2H), 4.12 (t, 2H), 3.84 (s, 3H), 3.80 (s, 3H), 3.76 (s, 3H), 2.73 (t, 2H), 2.22 (s, 6H), 1.27 (s, 9H).

C006: (E)-3-[2-(2-Dimethylamino-ethoxy)-5-hydroxy-phenyl]-1-(2,3,4-trimethoxy-phenyl)-propenone General procedure H gave the title product as yellow crystals in 16% yield. $^1$H-NMR (CDCl$_3$) δ 9.18 (bs, 1H), 7.76 (d, 1H), 7.36 (d, 1H), 7.32 (d, 1H), 7.09 (d, 1H), 6.96-6.92 (m, 2H), 6.82 (dd, 1H), 4.02 (t, H), 3.87 (s, 3H), 3.82 (s, 3H), 3.79 (s, 3H), 2.61 (t, 2H), 2.17 (s, 6H).

C007: (E)-3-[2-(2-Dimethylamino-ethoxy)-phenyl]-1-(2-fluoro-4-methoxy-phenyl)-propenone General procedure H gave the fumarate of the title product as yellow crystals in 45% yield. $^1$H-NMR (DMSO-$d_6$) δ 7.90 (dd, 1H), 7.82-7.76 (m, 2H), 7.59 (dd, 1H), 7.43 (dd, 1H), 7.14 (d, 1H), 7.05-6.91 (m, 3H), 6.56 (s, 1H), 4.21 (t, 2H), 3.87 (s, 3H), 2.85 (t, 2H), 2.33 (s, 6H).

C008: (E)-3-[2-(2-Dimethylamino-ethoxy)-5-methyl-phenyl]-1-(2-dimethylaminomethyl-phenyl)-propenone General procedure H gave the fumarate of the title product as yellow crystals in 25% yield. $^1$H-NMR (DMSO-$d_6$) δ 7.67-7.46 (m, 6H), 7.30 (d, 1H), 7.23 (dd, 1H), 7.00 (d, 1H), 6.58 (s, 4H), 4.20 (t, 2H), 3.70 (s, 2H), 2.95 (t, 2H), 2.38 (s, 6H), 2.27 (s, 3H), 2.23 (s, 6H).

C009: N-(2-{3-[2-(2-Dimethylamino-ethoxy)-5-methyl-phenyl]-(E)-acryloyl}-phenyl)-benzenesulfonamide General procedure H gave the title product as yellow crystals in 48% yield. $^1$H-NMR (CDCl$_3$) δ 8.02-7.97 (m, 2H), 7.91-7.88 (m, 2H), 7.79 (dd, 1H), 7.70 (d, 1H), 7.55-7.41 (m, 5H), 7.24 (dd, 1H), 7.18 (dt, 1H) 6.92 (d, 1H), 4.21 (t, 2H), 2.87 (t, 2H), 2.41 (s, 6H), 2.39 (s, 3H).

C010: (E)-3-[4-(2-Dimethylamino-ethoxy)-biphenyl-3-yl]-1-(4-methoxy-phenyl)-propenone General procedure H gave the fumarate of the title product as yellow crystals in 73% yield. $^1$H-NMR (DMSO-d$_6$) δ 8.22-8.16 (m, 3H), 8.05 (d, 2H), 7.77-7.71 (m, 3H), 7.47 (t, 2H), 7.35 (t, 1H), 7.23 (d, 1H), 7.09 (d, 2H), 6.58 (s, 2H), 4.31 (t, 2H), 3.87 (s, 3H), 2.99 (t, 2H), 2.45 (s, 6H).

C011: (E)-3-[4-(2-Dimethylamino-ethoxy)-biphenyl-3-yl]-1-(2-fluoro-4-methoxy-phenyl)-propenone General procedure H gave the fumarate of the title product as yellow crystals in 77% yield. $^1$H-NMR (DMSO-d$_6$) δ 8.07 (d, 1H), 7.96 (d, 1H), 7.84 (t, 1H), 7.77-7.70 (m, 4H), 7.48 (t, 2H), 7.34 (t, 1H), 7.23 (d, 1H), 7.00-6.91 (m, 2H), 6.58 (s, 2H), 4.30 (t, 2H), 3.87 (s, 3H), 2.96 (t, 2H), 2.41 (s, 6H).

C012: (E)-3-[4-(2-Dimethylamino-ethoxy)-biphenyl-3-yl]-1-(2,3,4-trimethoxy-phenyl)-propenone General procedure H gave the fumarate of the title product as colourless crystals in 84% yield. $^1$H-NMR (DMSO-d$_6$) δ 8.03 (d, 1H), 7.85 (d, 1H), 7.74-7.70 (m, 3H), 7.61 (d, 1H), 7.45 (t, 2H), 7.36-7.30 (m, 2H) 7.22 (d, 1H), 6.94 (d, 1H), 6.58 (s, 2H), 4.27 (t, 2H), 3.87 (s, 3H), 3.82 (s, 3H), 3.79 (s, 3H), 2.92 (t, 2H), 2.36 (s, 6H).

C013: (E)-1-(2-Chloro-4-methoxy-phenyl)-3-[4-(2-dimethylamino-ethoxy)-biphenyl-3-yl]-propenone General procedure H gave the fumarate of the title product as slightly yellow crystals in 63% yield. $^1$H-NMR (DMSO-d$_6$) δ 8.10 (d, 1H), 7.79 (d, 1H), 7.75-7.71 (m, 2H), 7.62 (d, 1H), 7.54 (d, 1H), 7.45 (t, 2H), 7.34 (t, 1H), 7.20 (d, 1H), 7.16 (d, 11t), 7.04 (dd, 1H), 6.57 (s, 2H), 4.26 (t, 2H), 3.86 (s,3H), 2.91 (t, 2H), 2.35 (t, 6H).

C014: (E)-3-[4-(2-Dimethylamino-ethoxy)-2'-methoxy-biphenyl-3-yl]-1-(4-methoxy-phenyl)-propenone General procedure H gave the fumarate of the title product as slightly yellow crystals in 55% yield. $^1$H-NMR (DMSO-d$_6$) 6 8.15 (d, 2H), 8.02 (d, 2H), 7.95 (d, 1H), 7.53 (dd, 1H), 7.35 (t, 2H), 7.19-7.01 (m, 5H), 6.58 (s, 1H), 4.26, (t, 2H), 3.86 (s, 3H), 3.78 (s, 3H), 2.86 (t, 2H), 2.36 (s, 6H).

C015: (E)-3-[4-(2-Dimethylamino-ethoxy)-2'-methoxy-biphenyl-3-yl]-1-(2-fluoro-4-methoxy-phenyl)-propenone General procedure H gave the fumarate of the title product as yellow crystals in 65% yield. $^1$H-NMR (DMSO-d$_6$) δ 7.93 (d, 1H), 7.86-7.80 (m, 2H), 7.63 (dd, 1H), 7.55 (dd, 1H), 7.37-7.32 (m, 2H), 7.18 (d, 1H), 7.12 (d, 1H), 7.06-6.91 (m, 3H), 6.59 (s, 2H),4.27 (t, 2H), 3.87 (s, 3H), 3.78 (s, 3H), 2.90 (t, 2H), 2.36 (s, 6H).

C016: (E)-3-[4-(2-Dimethylamino-ethoxy)-2'-methoxy-biphenyl-3-yl]-1-(2,3,4-trimethoxy-phenyl)-propenone General procedure H gave the fumarate of the title product as slightly yellow crystals in 60% yield. $^1$H-NMR (DMSO-d$_6$) δ 7.85 (d, 1H), 7.83 (d, 1H), 7.53 (dd, 1H), 7.50 (d, 1H), 7.37-7.31 (m, 3H), 7.17 (d, 1H), 7.11 (d, 1H), 7.03 (t, 1H), 6.93 (d, 1H), 6.59 (s, 3H), 4.28 (t, 2H), 3.87 (s, 3H), 3.82 (s, 3H), 3.78 (s, 3H), 3.78 (s, 3H), 2.96 (t, 2H), 2.40 (s, 6H).

C017: (E)-1-(2-Chloro-4-methoxy-phenyl)-3-[4-(2-dimethylamino-ethoxy)-2'-methoxy-biphenyl-3-yl]-propenone General procedure H gave the fumarate of the title product as slightly yellow crystals in 37% yield. $^1$H-NMR (DMSO-d$_6$) δ 7.84 (d, 1H), 7.76 (d, 1H), 7.59 (d, 1H), 7.55 (dd, 1H), 7.40 (d, 1H), 7.36-7.31 (m, 2H), 7.16-6.99 (m, 5H), 6.59 (s, 2H), 4.21 (t, 2H), 3.85 (s, 3H), 3.77 (s, 3H), 2.78 (t, 2H), 2.26 (s, 6H).

C018: (E)-3-[2'-Chloro-4-(2-dimethylamino-ethoxy)-biphenyl-3-yl]-1-(2,3,4-trimethoxy-phenyl)-propenone General procedure H gave the fumarate of the title product as colourless crystals in 20% yield. $^1$H-NMR (DMSO-d$_6$) δ 7.86-7.81 (m, 2H), 7.58-7.39 (m, 6H), 7.35 (d, 1H), 7.22 (d, 1H), 6.93 (d, 1H), 6.59 (s, 2H), 4.26 (t, H), 3.87 (s, 3H), 3.81 (s, 3H), 3.78 (s, 3H), 2.85 (t, 2H), 2.32 (s, 6H).

C019: (E)-3-[4-(2-Dimethylamino-ethoxy)-2'-methyl-biphenyl-3-yl]-1-(4-methoxy-phenyl)-propenone General procedure H gave the fumarate of the title product as Yellow crystals in 76% yield. $^1$H-NMR (DMSO-d$_6$) δ 8.16 (d, 2H), 8.05 (s, 2H), 7.94 (d, 1H), 7.38 (dd, 1H), 7.33-7.24 (m, 4H), 7.20 (d, 1H), 7.06 (d, 2H) 6.58 (s, 2H), 4.30 (t, 2H), 3.86 (s, 3H), 2.96 (t, 2.43 (s, 6H), 2.27 (s, 3H).

C020: (E)-3-[4-(2-Dimethylamino-ethoxy)-2'-methyl-biphenyl-3-yl]-1-(2-fluoro-4-methoxy-phenyl)-propenone General procedure H gave the fumarate of the title product as slightly yellow crystals in 73% yield. $^1$H-NMR (DMSO-d$_6$) δ 7.94 (d, 1H), 7.83 (t, 1H), 7.75 (d, 1H), 7.66 (dd, 1H), 7.40 (dd, 1H), 7.32-7.19 (m, 5H), 6.98-6.89 (m, 2H), 6.58 (s, 2H), 4.29 (t, 2H), 3.86 (s, 3H), 2.94 (t, 2H), 2.39 (s, 6H), 2.26 (s, 3H).

C021: (E)-3-[4-(2-Dimethylamino-ethoxy)-2'-methyl-biphenyl-3-yl]-1-(2,3,4-trimethoxy-phenyl)-propenone General procedure H gave the fumarate of the title product as slightly yellow crystals in 73% yield. $^1$H-NMR (DMSO-d$_6$) δ 7.84 (d, 1H), 7.70 (d, 1H), 7.54 (d, 1H), 7.38 (dd, 1H), 7.34 (d, 1H), 7.30-7.22 (m, 4H), 7.19 (d, 1H, 6.92 (d, 1H), 6.59 (s, 2H), 4.24 (t, 2H), 3.86 (s, 3H), 3.80 (s, 3H), 3.78 (s, 3H), 2.83 (t, 2H), 2.30 (s, 6H), 2.26 (s, 3H).

C022: (E)-1-(2-Chloro-4-methoxy-phenyl)-3-[4-(2-dimethylamino-ethoxy)-2'-methyl-biphenyl-3-yl]-propenone General procedure H gave the fumarate of the title product as yellow crystals in 54% yield. $^1$H-NMR (DMSO-d$_6$) δ 7.79 (d, 1H), 7.76 (d, 1H), 7.60 (d, 1H), 7.45 (d, 1H), 7.40 (dd, 1H), 7.31-7.14 (m, 6H), 7.03 (dd, 1H), 6.59 (s, 2H), 4.22 (t, 2H), 3.85 (s, 3H), 2.80 (t, 2H), 2.28 (s, 6H), 2.25 (s, 3H).

C023: (E)-3-[4-(2'-Dimethylamino-ethoxy)-3',5'-dimethyl-biphenyl-3-yl]-1-(4-methoxy-phenyl)-propenone General procedure H gave the fumarate of the title product as slightly yellow crystals in 74% yield. $^1$H-NMR (DMSO-d$_6$) δ 8.19-8.01 (m, 5H), 7.69 (dd, 1H), 7.34 (bs, 2H), 7.21 (d, 1H), 7.10 (d, 2H), 6.98 (s, 1H), 6.59 (s 2H), 4.29 (t, 2H), 3.87 (s, 3H), 2.94 (t, 2H), 2.42 (s, 6H), 2.35 (s, 6H).

C024: (E)-3-[4-(2-Dimethylamino-ethoxy)-3',5'-dimethyl-biphenyl-3-yl]-1-(2-fluoro-4-methoxy-phenyl)-propenone General procedure H gave the fumarate of the title product as yellow crystals in 73% yield. $^1$H-NMR (DMSO-d$_6$) δ 8.02 (d, 1H), 7.93 (d, 1H), 7.83 (t, 1H), 7.73 (dd, 1H), 7.69 (t, 1H), 7.31 (bs, 2H), 7.20 (d, 1H), 7.00-6.91 (m, 3H), 6.59 (s, 2H), 4.27 (t, 2H), 3.87 (s, 3H), 2.90 (t, 2H), 2.36 (s, 6H), 2.33 (s, 6H).

C025: (E)-3-[4-(2-Dimethylamino-ethoxy)-3',5'-dimethyl-biphenyl-3-yl]-1-(2,3,4-trimethoxy-phenyl)-propenone General procedure H gave the fumarate of the title product as yellow crystals in 52% yield. $^1$H-NMR (DMSO-d$_6$) δ 7.99 (d, 1H), 7.83 (d, 1H), 7.68 (dd, 1H), 7.59 (d, 1H), 7.34 (d, 1H), 7.30 (bs, 2H), 7.19 (d, 1H), 696 (bs, 1H), 6.93 (d, 1H), 6.58 (s, 2H), 4.27 (t, 2H), 3.87 (s, 3H), 3.82 (s, 3H), 3.79 (s, 3H), 2.93 (t, 2H), 2.38 (s, 6H), 2.33 (s, 6H).

C026: (E)-1-(2-Chloro-4-methoxy-phenyl)-3-[4-(2-dimethylamino-ethoxy)-3',5'-dimethyl-biphenyl-3-yl]-propenone General procedure H gave the fumarate of the title product as yellow crystals in 77% yield. $^1$H-NMR (DMSO-d$_6$) δ 8.05 (d, 1H), 7.76 (d, 1H), 7.71 (dd, 1H), 7.60 (d, 1H), 7.51 (d, 1H), 7.32 (bs, 2H), 7.18 (d, 1H) 7.16 (d, 1H), 7.05 (dd, 1H), 6.96 (bs, 1H), 6.59 (s, 2H), 4.22 (t, 2H), 3.86 (s, 3H), 2.82 (t, 2H), 2.33 (s, 6H), 2.29 (s, 6H).

C027: N-(2-{3-[5-tert-Butyl-2-(2-dimethylamino-ethoxy)-phenyl]-(E)-acryloyl}-phenyl)-benzenesulfonamide General procedure H gave the title product as yellow crystals in 33% yield. $^1$H-NMR (CDCl$_3$) δ 7.97 (dd, 1H), 7.93 (d, 1H), 7.87-7.84 (m, 2H), 7.76 (dd, 1H), 7.73 (d, 1H), 7.54 (d, 1H), 7.51-7.37 (m, 5H), 7.14 (m, 1H), 6.92 (d, 1H), 4.18 (t, 2H) 2.82 (t, 2H), 2.36 (s, 6H), 1.35 (s, 9H).

C028: (E)-3-[3,5-Di-tert-butyl-2-(2-dimethylamino-ethoxy)-phenyl]-1-(2-fluoro-4-methoxy-phenyl)-propenone General procedure H gave the title product as yellow crystals in 11% yield. $^1$H-NMR (CDCl$_3$) δ 7.97 (dd, 1H), 7.79 (dd, 1H), 7.42 (d, 1H), 7.35 (d, 1H), 7.30 (dd, H), 6.72 (dd, 1H), 6.60 (dd, 1H), 3.85, (t, 2H), 3.81 (s, 3H), 2.72 (t, 2H), 2.24 (s, 6H), 1.34 (s, 9H), 1.26 (s, 9H).

C029: (E)-3-[4-(2-Dimethylamino-ethoxy)-[1,1';4',1''']terphenyl-3-yl]-1-(2-fluoro-4-methoxy-phenyl)-propenone General procedure H gave the title product as yellow crystals in 23% yield. $^1$H-NMR (CDCl$_3$) δ 8.06 (dd, 1H), 7.86-7.80 (m, 2H), 7.63-7.54 (m, 4H), 7.39 (dd, 2H), 7.31 (s, 1H), 6.96 (d, 1H), 6.72 (dd, 1H), 6.59 (dd, 1H), 4.15 (t, 2H), 3.81, (s, 3H), 2.80 (d, 2H), 2.30 (s, 2H).

C030: (E)-1-(2-Diethylaminomethyl-phenyl)-3-[4-(2-dimethylamino-ethoxy)-3',5'-dimethyl-biphenyl-3-yl]-propenone General procedure H gave the fumarate of the title product as green crystals in 33% yield. $^1$H-NMR (DMSO-d$_6$) δ 8.02 (d, 1H), 7.67 (dd, 1H), 7.61 (d, 1H), 7.47-7.38 (m 4H), 7.37 (d, 1H), 7.31 (br, 2H), 7.15 (d, 1H) 6.96 (br, 1H), 6.59 (s, 3H) 4.19 (t, 2H), 3.86 (s, 2H), 2.78 (t, 2H), 2.40 (q, 4H), 2.39 (s, 6H), 2.24 (s, 6H), 0.86 (t, 6H).

C031: (E)-3-[4-(2-Dimethylamino-ethoxy)-2'-methoxy-biphenyl-3-yl]-1-[2-(4-methyl-piperazin-1-ylmethyl)-phenyl]-propenone General procedure H gave the fumarate of the title product as yellow crystals in 40% yield. $^1$H-NMR (DMSO-d$_6$) δ 7.85 (d, 1H), 7.59 (d, 1H), 7.56-7.33 (m, 7H), 7.25 (d, 1H), 7.16-7.12 (dd, 2H), 7.04 (t, 1H), 6.61 (s, H), 4.22 (t, 2H), 3.79 (s, 3H), 3.60 (s, 2H), 2.81 (s, 2H), 2.50-2.30 (broad, 8H), 2.28 (s, 6H), 2.22 (s, 3,H).

C032: (E)-3-[4-(2-Dimethylamino-ethoxy)-2'-methyl-biphenyl-3-yl]-1-[2-(4-methyl-piperazin-1-ylmethyl)-phenyl]-propenone General procedure H gave the title product as yellow crystals in 39% yield. $^1$H-NMR (CDCl$_3$) δ 7.63 (d, 1H), 7.55 (d, 1H), 7.41-7.24 (m, 9H), 7.10 (d, 1H), 6.96 (d, 1H), 4.15 (t, 2H), 3.61 (s, 2H), 2.73 (t, 2H), 2.40 (bs, 8H), 2.30 (s, 3H), 2.27 (s, 6H), 2.18 (s, 3H).

C033: (E)-3-[2-(2-Dimethylamino-ethoxy)-5-methyl-phenyl]-1-[2-(2-dimethylamino-ethoxy)-phenyl]-propenone General procedure H gave the fumarate of the title product as colourless crystals in 15% yield. $^1$H-NMR (DMSO-d$_6$) δ 7.79 (d, 1H), 7,59 (d, 1H), 7.55-0.42 (m, 3H), 7.24-7.19 (m, 2H), 7.06 (dd, 1H), 7.00 (d, 1H), 6.58 (s, 4H), 4.23 (t, 2H), 4.15 (t, 2H), 2.84 (t, 2H), 2.80 (t, 2H), 2.33 (s, 6H), 2.27 (s, 3H), 2.26 (s, 6H).

C034: (E)-3-[4-(2-Dimethylamino-ethoxy)-biphenyl-3-yl]-1-[4-(2-dimethylamino-ethylamino)-phenyl]-propenone General procedure H gave the fumarate of the title product as yellow crystals in 14% yield. $^1$H-NMR (DMSO-d$_6$) δ 8.16 (d, 1H), 8.08 (d, 1H), 8.01 (d, 2H), 7.96 (d, 1H), 7.75 (d, 2H), 7.70 (dd, 1H), 7.47 (dd, 2H), 7.35 (dd, 1H), 7.23 (d, 1H), 6.69 (d, 2H), 6.58 (s, 2H), 4.28 (t, 1H), 3.32 (dt, 2H), 2.89 (t, 2H), 2.70 (t, 2H), 2.38 (s, 6H).

C035: (E)-3-[4-(2-Dimethylamino-ethoxy)-2'-methyl-biphenyl-3-yl]-1-(2-dimethylaminomethyl-phenyl)-propenone General procedure H gave the fumarate of the title compound as pale green crystals in 28% yield. $^1$H-NMR (DMSO-d$_6$) δ 7.79 (d, 1H), 7.69 (d, 1H), 7.55-7.37 (m, 5H), 7.28-7.22 (m, 5H), 7.16 (d, 1H), 6.59 (s, 4H), 4.24 (t, 2H), 3.67 (s, 2H), 2.87 (t, 2H), 2.32 (s, 6H), 2.26 (s, 3H), 2.17 (s, 6H).

C036: (E)-3-[4-,(2-Dimethylamino-ethoxy)-2'-methoxy-biphenyl-3-yl]-1-(2-dimethylaminomethyl-phenyl)-propenone General procedure H,gave the fumarate of the title compound as pale green crystals in 29% yield. $^1$H-NMR (DMSO-d$_6$) δ 7.86 (d, 1H), 7.68 (d, 1H), 7.55-7.43 (m, 5H), 7.37-7.31 (m, 3H), 7.12 (t, 2H), 7.05 (t, 1H), 6.58 (s, 4H), 4.25 (t, 2H), 3.76 (s, 3H) 3.68 (s, 2H), 2.91 (t, 2H), 2.34 (s, 6H), 2.19 (s, 6H).

C037: (E)-3-[4-(2-Dimethylamino-ethoxy)-biphenyl-3-yl]-1-(3-dimethylaminomethyl-phenyl)-propenone General procedure H gave the title compound as yellow oil in 42% yield. $^1$H-NMR (CDCl$_3$) δ 8.07 (d, 1H), 7.90-7.88 (m, 2H), 7.77 (d, 1H), 7.71 (d, 1H), 7.54-7.47 (m, 4H), 7.41-7.38 (m, 3H), 7.36-7.25 (m, 1H), 6.96 (d, 1H), 4.15 (t, 2H), 3.44 (s, 2H),2.80 (t, 2H), 2.31 (s, 6H), 2.20 (s, 6H).

C038: (E)-3-[5-tert-Butyl-2-(2-dimethylamino-ethoxy)-phenyl]-1-(2-diethylaminomethyl-phenyl)-propenone General procedure H gave the title compound as a green oil in 42% yield. $^1$H-NMR (DMSO-d$_6$) δ 7.68 (d, 1H), 7.52 (d, 1H), 7.43-7.32 (m, 5H), 7.20 (d, 1H), 6.98 (d, 1H), 4.04 (t, 2H), 3.59 (s, 2H), 2.54 (t (under DMSO), 2H), 2.33 (q, 4H), 2.08 (s, 6H), 1.28 (s, 9H), 0.82 (t, 6H).

C039: (E)-3-[2-(2-Dimethylamino-ethoxy)-4-hydroxy-5-propyl-phenyl]-1-(2-fluoro-4-methoxy-phenyl)-propenone General procedure H gave the title compound as yellow crystals in 14% yield. $^1$H-NMR (DMSO-d$_6$) δ 7,74-7,60 (m, 2H); 7,36-7,25 (m, 2H); 6,86-6,78 (m; 2H); 6,48-6,41 (m, 2H); 3,97 (t, 2H); 3,75 (s, 3H); 2,66 (t, 2H); 2,40-2,32 (m, 3H); 2,17 (s, 6H);1,46-1,39 (m, 2H); 0,81-0,76 (t, 2H).

C040: (E)-3-[4-(2-Dimethylamino-ethoxy)-biphenyl-3-yl]-1-(4-hydroxy-phenyl)-propenone General procedure H gave the title compound as yellow crystals in 25% yield. $^1$H-NMR (CDCl$_3$) δ 7.99 (d, 1H), 7.93 (d, 1H), 7.76 (d, 1H), 7.73 (s, 1H), 7.52-7.47 (m, 3H), 7.36 (t, 2H), 7.28-7.23 (m, 1H), 6.95 (d, 1H), 6.84 (dd, 2H), 4.14 (t, 2H), 2.79 (t, 2H), 2.31 (s, 6H).

C041: (E)-3-[5-tert-Butyl-2-(2-dimethylamino-ethoxy)-phenyl]-1-(4-hydroxy-phenyl)-propenone General procedure H gave the fumarate of the title compound as yellow crystals in 47% yield. $^1$H-NMR (DMSO-d$_6$) δ 8.05 (d, 2H), 7.95 (s, 2H), 7.82 (d, 1H), 7.42 (d, 1H), 7.05 (d, 1H), 6.91 (d, 2H), 6.58 (s, 3H), 4.24 (t, 2H), 3.00 (t, 2H), 2.46 (s, 6H), 1.32 (s, 9H).

C042: N-(2-{3-[5-tert-Butyl-2-(3-dimethylamino-propoxy)-phenyl]-(E)-acryloyl}-phenyl)-benzene-sulfonamide General procedure H gave the title compound as yellow crystals in 27% yield. $^1$H-NMR (CDCl$_3$) δ 7.94 (d, 1H), 7.89-7.83 (m, 3H), 7.76 (dd, 1H), 7.56 (d, 1H), 7.4 (d, 1H), 7.52-7.37 (m, 5H), 7.17-7.12 (m, 1H), 6.92 (d, 1H), 4.14 (t, 2H) 2.50 (t, 2H), 2.26 (s, 6H), 2.06 (pen, 1H), 1.35 (s, 9H).

C043: (E)-3-[3-(2-Dimethylamino-ethoxy)-phenyl]-1-(2,3,4-trimethoxy-phenyl)-propenone General procedure H gave the fumarate of the title compound as slightly yellow crystals in 9% yield. $^1$H-NMR (CDCl$_3$) δ 7.39 (d, 1H), 7.33-7.27 (m, 2H), 7.19-7.14 (m, 2H), 7.09 (bs, 1H), 7.00 (dd, 1H), 6.80 (d, 1H), 6.59 (s, 2H), 4.29 (t, 2H), 382 (s, 3H), 3.76 (s, 3H), 3.73 (s, 3H), 3.53 (t, 2H), 2.91 (s, 6H).

C044: (E)-3-[3-(2-Dimethylamino-ethoxy)-phenyl]-1-(2-fluoro-4-methoxy-phenyl)-propenone General procedure H gave the fumarate of the title compound as slightly yellow crystals in 24% yield. $^1$H-NMR (DMSO-d$_6$) δ 7.85 (t, 1H), 7.63 (d, 1H), 7.52 (dd, 1H), 7.38-7.35 (m, 3H), 7.06-6.92 (m,3H), 6.57(s, 2H), 4.20 (t, 2H), 3.87 (s, 3H), 2.51 (t, 2H), 2.41 (s, 6H).

C045: (E)-1-(2,4-Dimethoxy-phenyl)-3-[3-(2-dimethylamino-ethoxy)-phenyl]-propenone General procedure H gave the fumarate of the title compound as slightly yellow crystals in 24% yield. $^1$H-NMR (DMSO-d$_6$) δ 7.61 (d, 1H), 7.55 (d, 1H), 7.49 (d, 1H), 7.39-7.29 (m, 3H), 7.02 (dt, 1H), 6.69 (d, 1H), 6.65 (dd, 1H), 6.57 (s, 2H), 4.20 (t, 2H), 3.89 (s, 3H), 3.84 (s, 3H), 2.92 (t, 2H), 2.42 (s, 6H).

C046: (E)-1-(2,5-Dimethoxy-phenyl)-3-[3-(2-dimethylamino-ethoxy)-phenyl]-propenone General procedure H gave the fumarate of the title compound as yellow crystals in 33% yield. $^1$H-NMR (DMSO-d$_6$) δ 7.32 (d, 1H), 7.24 (d, 1H), 7.19-7.13 (m, 3H), 7.01-6.94 (m, 2H), 6.88-6.84 (m, 2H), 6.42 (s, 2H), 4.01 (t, 2H), 3.65 (s, 3H), 3.59 (s, 3H), 2.67 (t, 2H), 2.20 (s, 6H).

C047: (E)-3-[3-(2-Dimethylamino-ethoxy)-phenyl]-1-(2-methoxy-phenyl)-propenone General procedure H gave the fumarate of the title compound as colourless crystals in 20% yield. $^1$H-NMR (DMSO-d$_6$) δ 7.55 (dt, 1H), 7.49 (dd, 1H), 7.44 (d, 2H), 7.38 (m, 3H), 7.20 (d, 1H), 7.09-7.00 (m, 2H), 4.57 (s, 2H), 4.19 (t, 2H), 3.86 (s, 3H), 2.91 (t, 2H), 2.42 (s, 6H).

C048: (E)-3-[3-(2-Dimethylamino-ethoxy)-phenyl]-1-(4-methoxy-phenyl)-propenone General procedure H gave the fumarate of the title compound as slightly yellow crystals in 10% yield. $^1$H-NMR (DMSO-d$_6$) δ 8.39 (d, 2H), 8.17 (d, 1H), 7.89 (d, IH), 7.72-7.55 (m, 3H), 7.32-7.23 (m, 3H), 6.78 (s, 2), 4.46 (t, 2H), 4.09 (s, 3H), 3.18 (t, 2H), 2.67 (s, 6H).

C049: (E)-3-[3-(2-Dimethylamino-ethoxy)-phenyl]-1-[2-(2-dimethylamino-ethoxy)-phenyl]-propenone General procedure H gave the title compound as yellow oil in 25% yield. $^1$H-NMR (CDCl$_3$) δ 7.65 (dd, 1H), 7.60 (d, 1H), 7.47 (d, 1H), 7.47 (dt, 1H), 7.31 (t, 1H), 7.22 (d, 1H), 7.1 (t, 1H), 7.05 (dt, 1H), 7.02 (m, 2H), 4.17 (t, 2H), 4.10 (t, 2H), 2.75 (t, 2H), 2.73 (t, 2H), 2.36 (s, 3H), 2.27 (s, 3H).

C050: (E)-3-[3-(3-Dimethylamino-propoxy)-phenyl]-1-(2-fluoro-4-methoxy-phenyl)-propenone General procedure H gave the title compound as yellow oil in 32% yield. $^1$H-NMR (CDCl$_3$) δ 7.90 (t, 1H), 7.75 (dd, 1H), 7.44 (dd, 1H), 7.32 (t, 1H), 7.22 (d, 1H), 7.17 (bs, 1H), 6.7 (dd, 1H), 6.81 (dd, 1H), 6.67 (dd, 1H), 4.07 (t, 2H), 3.89 (s, 3H), 2.48 (t, 2H), 2.28 (s, 6H), 1.99 (hep, 2H).

C051: (E)-1-(2,4-Dimethoxy-phenyl)-3-[3-(3-dimethylamino-propoxy)-phenyl]-propenone General procedure H gave the title compound as yellow oil in 52% yield. $^1$H-NMR (CDCl$_3$) δ 7.77 (d, 1H), 7.65 (d, 1H), 7.49 (d, 1H), 7.30 (t, 1H), 7.20 (d, 1H), 7.13 (t, 1H), 6.4 (dd, 1H), 6.58 (dd, 1H), 6.52 (d, 1H), 4.06 (t, 2H), 3.92 (s, 3H), 3.89 (s, 3H), 2.47 (t, 2H), 2.27 (s, 6H), 1.98 (hep, 2H).

C052: (E)-3-[3-(3-Dimethylamino-propoxy)-phenyl]-1-(2-methoxy-phenyl)-propenone General procedure H gave the title compound as yellow oil in 41% yield. $^1$H-NMR (CDCl$_3$) δ 7.62 (dd, 1H), 7.58 (d, 1H), 7.50 (dt, 1H), 7.35 (d, 1H), 7.31 (t, 1H), 7.19 (d, 1H), 7.12 (t, 1H), 7.07 (dd, 1H), 7.02 (d, 1H), 6.96 (dd, 1H), 4.06 (t, 2H), 3.92 (s, 3H), 2.47 (t, 2H), 2.27 (s, 6H), 1.98 (hep, 2H).

C053: (E)-1-(2,5-Dimethoxy-phenyl)-3-[3-(3-dimethylamino-propoxy)-phenyl]-propenone General procedure H gave the title compound as yellow oil in 28% yield. $^1$H-NMR (CDCl$_3$) δ 7.58 (d, 1H), 7.36 (d, 1H), 7.28 (t, 1H), 7.17-7.15 (m, 2H), 7.10 (t, 1H), 7.02 (dd, 1H), 6.94 (d, 2H), 4.04 (t, 2H), 3.85 (s, 3H), 3.80 (s, 3H), 2.45 (t, 2H), 2.25 (s, 6H), 2.04 (hep, 2H).

C054: (E)-3-[3-(3-Dimethylamino-propoxy)-phenyl]-1-(2,3,4-trimethoxy-phenyl)-propenone General procedure H gave the title compound as yellow oil in 21% yield. $^1$H-NMR (CDCl$_3$) δ 7.65 (d, 1H), 7.50 (d, 1H), 7.47 (d, 1H), 7.31 (t, 1H), 7.20 (d, 1H), 7.15 (t, 1H), 6.5 (dd, 1H), 6.77 (d, 1H), 4.06 (t, 2H), 3.94 (s, 3H), 3.94 (s, 3H), 3.93 (s, 3H), 2.47 (t, 2H), 2.27 (s, 6H), 1.98 (hep, 2H).

C055: E)-1-(3-Dimethylaminomethyl-phenyl)-3-[3-(3-dimethylamino-propoxy)-phenyl]-propenone General procedure H gave the title compound as yellow oil in 38% yield. $^1$H-NMR (CDCl$_3$) δ 7.97-7.92 (m, 2H), 7.79 (d, 1H), 7.59-7.57 (m, 2H), 7.49 (t, 1H), 7.34 (t, H), 7.26-7.20 (m, 2H), 6.98 (dd, 1H), 4.09 (t, 2H), 3.53 (s, 2H), 2.51 (t, 2H), 2.30 (s, 6H), 2.29 (s, 6H), 2.01 (m, 2H).

C056: (E)-3-[4-(2-Dimethylamino-ethoxy)-phenyl]-1-(2,3,4-trimethoxy-phenyl)-propenone General procedure H gave the fumarate of the title compound as slightly yellow crystals in 22% yield. $^1$H-NMR (CDCl$_3$) δ 7.69 (d, 2H), 7.51 (d, 1H), 7.36-7.29 (m, 2H), 7.01 (d, 2H), 6.92 (d, 1H), 6.57 (s, 2H), 4.19 (t, 2H), 3,.87 (s, 3H), 3.83 (s, 3H), 379 (s, 3H), 2.89 (t, 2H), 2.40 (s, 6H).

C057: (E)-3-(2,5-Dimethoxy-phenyl)-1-[2-(2dimethylamino-ethoxy)-phenyl]-propenone General procedure H gave the title compound as yellow-brown oil in 18% yield. $^1$H-NMR (CDCl$_3$) δ 7.93 (d, 1H), 7.62 (dd, 1H), 7.47-7.41 (m, 2H), 7.17 (d, 1H), 7.04 (dt, 1H), 6.99 dd, 1H), 6.90 (d, 1H), 6.84 (d, 1H), 4.17 (t, 2H), 3.83 (s, 3H), 3.80 (s, 3H), 2.74 (t, 2H), 2.27 (s, 6H).

C058: (E)-1-[2-(2-Dimethylamino-ethoxy)-phenyl]-3-(3-dimethylaminomethyl-phenyl)-propenone General procedure H gave the fumarate of the title compound as yellow crystals in 32% yield. $^1$H-NMR (CDCl$_3$) δ 7.73-7.70 (m, 2H), 7.62-7.43 (m, 6H), 7.23 (d, 1H), 7.09 (t, 1H), 6.60 (s, 4H), 4.27 (t, 2H), 3.63 (s, 2H), 2.83 (t, 2H), 2.29 (s, 12H).

C059: (E)-1-[2-(2-Dimethylamino-ethoxy)-phenyl]-3-(2-dimethylaminomethyl-phenyl)-propenone General procedure H gave the title compound as brown oil in 20% yield. $^1$H-NMR (CDCl$_3$) δ 8.10 (d, 1H), 7.77-7.74 (m, 1H), 7.63 (dd, 1H), 7.47-7.27 (m, 5H), 7.06-6.97 (m, 2H), 4.15 (t, 2H), 3.47 (s, 2H), 2.71 (t, 2H), 2.25 (s, 6H), 2.19 (s, 6H).

C060: (E)-3-(2,4-Dichloro-phenyl)-1-[2-(2-dimethylamino-ethoxy)-phenyl]-propenone General procedure H gave the title compound as yellow crystals in 9% yield. $^1$H-NMR (CDCl$_3$) δ 8.00 (d, 1H), 7.77 (d, 1H), 7.72 (dd, 1H), 7.57 (d, 1H), 7.50 (dt, 1H), 7.47 (d, 1H), 7.30-7.26 (m, 1H), 7.07 (dt, 1H), 7.01 (d, 1H), 4.19 (t, 2H), 2.73 (t, 2H), 2.28 (s, 6H).

C061: (E)-3-(2,5-Dimethoxy-phenyl)-1-[2-(3-dimethylamino-propoxy)-phenyl]-propenone General procedure H gave the title compound as yellow oil in 58% yield. $^1$H-NMR (CDCl$_3$) δ 7.56 (d, 1H), 7.33-7.22 (m, 3H), 7.08 (d, 1H), 6.94 (d, 1H), 6.85-6.76 (m, 3H), 3.88 (t, H), 3.58 (s, 3H), 3.54 (s, 3H), 2.29 (t, 2H), 1.74 (s, 6H), 1.59 (hep, 2H).

C062: (E)-3-(2,4-Dichloro-phenyl)-1-[2-(3-dimethylamino-propoxy)-phenyl]-propenone General procedure H gave the title compound as orange oil in 34% yield. $^1$H-NMR (CDCl$_3$) δ 7.96 (d, 1H), 7.66 (dd, 1H), 7.65 (d, 1H), 7.51 (m, 2H), 7.41 (d, 1H), 7.28 (dd, 1H), 7.07-6.99 (m, 2H), 4.13 (t, 2H), 2.37 (t, 2H), 2.14 (s, 6H), 1.94 (hep, 2H).

C063: (E)-3-(2,5-Dimethoxy-phenyl)-1-[3-(2-dimethylamino-ethoxy)-phenyl]-propenone General procedure I gave the title compound as yellow oil in 6% yield. $^1$H-NMR (CDCl$_3$) δ 8.08 (d, 1H), 7.60-7.53 (m, 3H), 7.39 (t, 1H), 7.17 (d, 1H), 7.15 (dd, 1H), 6.94 (dd, 1H), 6.87 (d, 1H), 4.15 (t, 2H), 3.87 (s, 3H), 3.83 (s, 3H), 2.77 (t, 2H), 2.35 (s, 6H).

C064: (E)-3-(2,5-Dimethoxy-phenyl)-1[4-(2-dimethylamino-ethoxy)-phenyl]-propenone General procedure H gave the fumarate of the title compound as yellow crystals in 37% yield. $^1$H-NMR (DMSO-d$_6$) δ 8.15 (d, 2H), 8.00 (d, 1H), 7.89 (d, 1H), 7.54 (d, 1H), 7.07 (d, 2H), 7.04-7.01 (m, 2H), 6.57 (s, 2H1), 4.26 (t, 2H), 3.84 (s, 3H),380 (s, 3H), 2.92 (t, 2H), 2.41 (s, 6H).

C065: (E)-3-[4-(2Dimethylamino-ethoxy)-3',5'-dimethyl-biphenyl-3-yl]-1-(2-ethoxy-phenyl)-propenone General procedure H gave the title compound as yellow crystals in 67% yield. $^1$H-NMR (DMSO-d$_6$) δ 7.98 (d, 1H), 7.85 (d, 1H), 7.69-7.61 (m, 2H), 7.55-7.49 (m, 2H), 7.29 (bs, 2H), 7.05 (t, 1H), 6.96 (bs, 1H), 4.18-4.11 (m, 4H), 2.65 (t, 2H), 2.33 (5, 6H), 2.19 (s, 6H), 1.33 (t, 3H).

C066: (E)-3-[4-(2-Dimethylaminoethoxy)-2'-methyl-biphenyl-3-yl]-1-(2-ethoxy-phenyl)-propenone General procedure H gave the fumarate of the title compound as yellow crystals in 34% yield. $^1$H-NMR (CDCl$_3$) δ 7.85 (d, 1H), 7.71 (d, 11H), 7.55-7.46 (m, 3H), 7.39 (dd, 1H), 7.30-7.13 (m, 6H), 7.03 (t, 1H), 6.59 (s, 3H), 4.27 (t, 2H), 4.11 (q, 2H), 2.94 (t, 2H), 239 (s, 6H), 2.25 (s, 3H); 1.26 (t, 3H).

C067: (E)-3-[4-(2-Dimethylamino-ethoxy)-3',5'-dimethyl-biphenyl-3-yl]-1(2-isopropoxy-phenyl)-propenone General procedure H gave the fumarate of the title compound as yellow crystals in 26% yield. $^1$H-NMR (DMSO-d$_6$) 6 7.99 (d, 11H), 7.87 (d, 1H), 7.70 (dd, 1H), 7.60 (d, 1H), 7.54-7.48 (m, 2H), 7.29 (bs, 2H), 7.19 (bd, 2H), 7.03 (t, 1h), 6.97 (bs, 1H), 6.59 (s, 3H), 4.8 (m, 1H), 4.25 (t, 2H), 2.90 (t, 2H), 2.37 (s, 6H), 2.33 (s, 6H), 1.31 (s, 3H), 1,29 (s, 3H)

C068: (E)-3-[4-(2-Dimethylamino-ethoxy)-2'-m ethyl-biphenyl-3-yl]-1-[2-(1-hydroxy-ethylamino)-phenyl]-propenone General procedure H gave the fumarate of the title compound as orange powder in 5% yield. $^1$H$^1$-NMR (DMSO-d$_6$) δ 9.28 (t, 1H), 8.19-8.10 (m, 2H), 7.96 (d, 1H), 7.89 (d, 1H), 7.42-7.24 (m, 6H), 7.19 (d, 1H), 6.81 (d, 1H), 6.59 (t, 1H), 6.59 (s, 2H), 4.26 (t, 2H), 3.28 (q, 2H), 2.86 (t, 2H), 2.36 (s, 6H), 2.27 (s, 3H).

C069: (E)-3-[4-(2-Dimethylamino-ethoxy)-3',5'-dimethyl-biphenyl-3-yl]-1-[2-(2-hydroxy-ethylamino)-phenyl]-propenone General procedure H gave the title compound as orange powder in 39% yield. $^1$H-NMR (DMSO-d$_6$) δ 9.27 (t, 1H), 8.21-8.16 (m, 2H), 8.10 (d, 1H), 7.95 (d, 1H), 7.66 (dd, 1H), 7,41 (t, 1H), 7.33 (bs, 2H), 7.20 (d, 1H), 6.98 (bs, 1H), 6.82 (d, 1H), 6.64(t, 1H), 4.89 (t, 1H), 4.22 (t, 2H), 3.66 (q, 2H), 3.29 (t, 2H), 2.75 (t, 2H), 2.35 (s, 6H), 2.27 (s, 6H).

C070: (E)-3-[3-(2-Dimethylamino-ethoxy)-phenyl]-1-(2-dimethylaminomethyl-phenyl)-propenone General procedure H gave the title compound as brownish oil in 54% yield. $^1$H-NMR (DMSO-d$_6$) δ 7.48-7.37 (m, 4H), 7.33-7.31 (m, 2H), 7.28-7.24 (m, 3H), 6.98 (dt, 1H), 4.08 (t, 2H), 3.51 (s, 2H), 2.61 (t, 2H), 2.20 (s, 6H), 2.02 (s, 6H).

C071: (E)-1-(2-Dimethylaminomethyl-phenyl)-3-[3-(3-dimethylamino-propoxy)-phenyl]-propenone General procedure H gave the title compound as yellow oil in 55% yield. $^1$H-NMR (DMSO-d$_6$) δ 7.49-7.38 (m, 4H), 7.32 (d, 1H), 7.30-7.28 (m, 2H), 7.24 (bs, 2H), 6,97 (dt, 1H), 4.03 (t, 2H), 3.51 (s, 2H), 2.34 (t, 2H), 2.13 (s, 6H), 2.02 (s, 6H), 0.83 (p, 2H).

C072: 3-[4-(2-Dimethylamino-ethoxy)-3',5'-dimethyl-biphenyl-3-yl]-1-(4-fluoro-phenyl)-propan-1-one General procedure N gave the title compound as colourless oil in 33% yield. $^1$H-NMR (CDCl$_3$) δ 8.05 (m, 2H), 7.43 (m, 2H), 7.2-7.08 (m, 4H), 7.00 (bs, 1H), 6.94 (bd, 1H), 4.18 (t, 2H), 3.32 (t, 2H), 3.12 (t, 2H), 2.80 (t, 2H), 2.40 (s, 6H), 2.35 (s, 6H).

C073: 3-[4-(2-Dimethylamino-ethoxy)-2'-methyl-biphenyl-3-yl]-1-(2-dimethylaminomethyl-phenyl)-propan-1-one General procedure N gave the fumarate of the title compound as white crystals in 39% yield. $^1$H-NMR (DMSO-d$_6$) δ 7.47 (d, 1H), 7.45-7.30 (m, 3H), 7.25-7.10 (m, 6H),7.02 (t, 1H), 6.60 (s, 5H), 4.15 (t, 2H), 3.53 (bs, 2H), 3.15 (t, 2H), 2.90 (t, 2H), 2.80 (t, 2H), 2.33 (s, 6H), 2.20 (s, 3H), 2.06 (s, 6H).

C074: (E)-3-[4-(2-Dimethylamino-ethoxy)-3',5'-dimethyl-biphenyl-3-yl]-1-[2-(2-dimethylamino-ethylamino)-phenyl]-propenone General procedure H gave the fumarate of the title compound as orange powder in 45% yield. $^1$H-NMR (DMSO-d$_6$) δ 9.18 (t,1H), 8.22-8.10 (m,3H), 7.96 (d,1H), 7.68 (dd,1H), 7.43 (t,1H), 7.33 (s,2H), 7.21 (d,1H), 6.98 (s, 1H), 6.85 (d, 1H), 6.67 (t, 1H), 6.58 (s, 5), 4.31 (t, 2H), 3.50-3.35 (m, 2H), 3.01 (t,2H), 2.76 (t,2H), 2.45 (s,6H), 2.42 (s, 6H), 2.35 (s, 6H).

C075: (E)-3-[4-(2-Dimethylamino-ethoxy)-3',5'-dimethyl-biphenyl-3-yl]-1-[3-(2-dimethylamino-ethylamino)-phenyl]-propenone General procedure H gave the fumarate of the title compound as orange powder in 34% yield. $^1$H-NMR (DMSO-d$_6$) δ 8.13 (d, 1H), 8.08-7.95 (m, 2H), 7.70 (dd, 1H), 7.42 (d, 1H), 7.37-7.18 (m, 5H), 6.97 (s, 1H), 6.90 (dd, 1H), 6.58 (s, 4H), 4.31 (t, 2H), 3.50-3.35 (m, 2H), 2.96 (t, 2H), 2.88 (t, 2H), 2.41 (s, 6H), 2.35 (s, 6H).

C076: (E)-3-[4-(2-Dimethylamino-ethoxy)-3',5'-dimethyl-biphenyl-3-yl]-1-{2-[(2-dimethylamino-ethyl)-methyl-amino]-phenyl}-propenone General procedure H gave the fumarate of the title compound as yellow crystals in 35% yield. $^1$H-NMR (DMSO-$d_6$) δ 7.98 (d, 1H), 7.65 (d, 1H), 7.52 (dd, 1H), 7.37 (d, 1H), 7.30-7.30 (m, 2H), 7.08 (s, 2H), 7.00-6.92 (m, 2H), 6.80 (s, 1H), 6.74 (s, 1H), 6.33 (s, 4H). 4.05 (t, 2H), 3.05 (t, 2H), 2.70 (t, 2H), 2.88 (t, 2H), 2.15 (s, 6H), 2.10 (s, 6H), 2.05 (s, 6H).

C077: (E)-1-(2-Butoxy-phenyl)-3-[4-(2-dimethyl-lamino-ethoxy)-3',5'-dimethyl-biphenyl-3-yl]-propenone General procedure H gave the fumarate of the title compound as yellow crystals in 66% yield. $^1$H-NMR (DMSO-$d_6$) δ 8.00 (d, 1H), 7.88 (d, 1H), 7.69 (dd, 1H), 7.60 (d, 1H), 7.56-7.47 (m, 2H), 7.30 (s, 2H), 7.22-7.13 (m, 2H), 7.05 (t, 1H), 6.96 (s, 1H), 6.59 (s, 3H), 4.28 (t, 2H), 4.09 (t, 2H), 2.98 (t, 2H), 2.42 (s, 6H), 2.32 (s, 6H), 1.74-1.60 (m, 2H), 1.43-1.28 (m, 2H), 0.70 (t, 3H).

C078: (E)-3-[4-(2-dimethylamino-ethoxy)-3',5'-dimethyl-biphenyl-3-yl]-1-(2-fluoro-phenyl)-propenone General procedure H gave the fumarate of the title compound as yellow powder in 83% yield. $^1$H-NMR (DMSO-$d_6$) δ 8.05 (d, 1H), 7.92 (d, 1H), 7.80-7.60 (m, 3H), 7.43-7.30 (m, 3H), 7.20 (d, 1H), 6.97 (s, 1H), 6.59 (s, 2H), 4.25 (t, 2H), 2.90 (t, 2H), 2.35 (s, 6H), 2.3 (s, 6H).

C079: (E)-3-[4-(2-Dimethylamino-ethoxy)-3',5'-dimethyl-biphenyl-3-y]-1-(3-fluoro-phenyl)-propenone General procedure H gave, the fumarate of the title compound as yellow powder in 48% yield. $^1$H-NMR (DMSO-$d_6$) δ 8.18 (d, 1H), 8.10 (s, 2H), 8.02 (d, 1H), 7.93 (dt, 1H), 7.75-7.60 (m, 2H), 7.53 (td, 1H), 7.33 (s, 2H), 7.22 (d, 1H), 6.98 (s, 1H), 6.58 (s, 1H), 4.2 (t, 2H), 2.85 (t, 2H), 2.35 (s, 12H).

C080: (E)-3-[4-(2-Dimethylamino-ethoxy)-3',5'-dimethyl-biphenyl-3-yl]-1-(4-fluoro-phenyl)-propenone General procedure H gave the title compound as yellow powder in 82% yield. $^1$H-NMR (DMSO-$d_6$) δ 8.30-8.20 (m, 2H), 8.18-8.01 (m, 3H), 7.68 (dd, 1H), 7.41 (t, 2H), 7.32 (s, 2H), 7.20 (d, 1H), 6.97 (s, 1H), 4.21 (t, 2H), 2.73 (t, 2H), 2.34 (s, 6H), 2.27 (s, 6H).

C081: (E)-1-(2-Bromo-phenyl)-3-[4-(2-dimethyl-lamino-ethoxy)-3',5'-dimethyl-biphenyl-3-yl]-propenone General procedure H gave the fumarate of the title compound as yellow crystals in 58% yield. $^1$H-NMR (DMSO-$d_6$) δ 8.07 (d, 1H), 7.78-7.63 (m, 3H), 7.58-7.38 (m, 4H), 7.33 (s, 2H), 7.17 (d, 1H), 6.96 (s, 1H), 6.59 (s, 2H), 4.20 (t, 2H), 2.78 (t, 2H), 2.33 (s, 6H), 2.27 (s, 6H).

C082: (E)-1-(3-Bromo-phenyl)-3-[4-(2-dimethyl-lamino-ethoxy)-3',5'-dimethyl-biphenyl-3-yl]-propenone General procedure H gave the fumarate of the title compound as yellow crystals in 23% yield. $^1$H-NMR (DMSO-$d_6$) δ 8.25 (s, 1H), 8.22-8.01 (m, 4H), 7.87 (d, 1H), 7.72 (dd, 1H), 7.55 (t, 1H), 7.33 (s, 2H), 7.22 (d, 1H), 6.98 (s, 1H), 6.59 (s, 3H), 4.31 (t, 2H), 3.00 (t, 2H), 2.45 (s, 6H), 2.34 (s, 6H).

C083: (E)-1-(4-Bromo-phenyl)-3-[4-(2-dimethyl-lamino-ethoxy)-3',5'-dimethyl-biphenyl-3-yl]-propenone General procedure H gave the title compound as yellow powder in 93% yield. $^1$H-NMR (DMSO-$d_6$) δ 8.16-8.05 (m, 5H), 7.79 (d, 2H), 7.69 (dd, 1H), 7.32 (s, 2H), 7.20 (d, 1H), 6.97 (s, 1H), 4.20 (t, 2H), 2.71 (t, 2H), 2.33 (s, 6H), 2.25 (s, 6H).

C084: (E)-3-[4-(2-Dimethylamino-ethoxy)-3',5'-dimethyl-biphenyl-3-yl]-1-(2-hydroxy-phenyl)-propenone General procedure H gave the title compound as yellow powder in 40% yield. $^1$H-NMR (DMSO-$d_6$) δ 12.68 (s, 1H), 8.30-8.20 (m, 2H), 8.20-8.10 (m, 2H), 7.72 (dd, 1H), 7.59 (t, 1H), 7.32 (s, 2H), 7.21 (d, 1H), 7.10-6.95 (m, 3H), 4.23 (t, 2H), 2.75 (t, H), 2.35 (s, 6H), 2.28 (s, 6H).

C085: (E)-3-[4-(2-Dimethylamino-ethoxy)-3',5'-dimethyl-biphenyl-3-yl]-1-(3-hydroxy-phenyl)-propenone General procedure H gave the title compound as yellow, crystals in 87% yield. $^1$H-NMR (DMSO-$d_6$) δ 9.75 (s, 1H), 8.15-7.95 (m, 3H), 7.72-7.55 (m, 2H), 7.44 (s, 1H), 7.40-7.25 (m, 3H), 7.20 (d, 1H), 7.05 (dd, 1H), 6.95 (s, 1H), 4.22 (t, 2H), 2.74 (t, 2H), 2.35 (s,6H), 2.27 (s, 6H).

C086: (E)-3-[4-(2-Dimethylamino-ethoxy)-3',5'-dimethyl-biphenyl-3-yl]-1-(4-hydroxy-phenyl)-propenone General procedure H gave the fumarate of the title compound as yellow crystals in 48% yield. $^1$H-NMR (DMSO-$d_6$) δ 8.15-7.93 (m, 5H), 7.67 (dd, 1H), 7.32 (s, 2H), 7.19 (d, 1H), 6.97 (s, 1H), 6.91 (d, 2H), 6.57 (s, 1H), 4.25 (t, 2H), 2.87 (t, 2H), 2.36 (s, 6H), 2.33 (s, 6H).

C087: (E)-1-(4-Cyclohexyl-phenyl)-3-[4-(2-dimethylamino-ethoxy)-3',5'-dimethyl-biphenyl-3-yl]-propenone General procedure H gave the title compound as yellow crystals in 59% Yield. H-NMR (DMSO-$d_6$) δ 8.15-7.97 (m, 5H), 7.67 (dd, 1H), 7.40 (d, 2H), 7.32 (s, 2H), 7.18 (d, 1H), 6.96 (s, 1H), 4.20 (t, 2H), 2.73 (t, 2H), 2.65-2.52 (m, 1H), 2.33,(s, 6H) 2.25 (s, 6H), 1.85-1.63 (m, 5H), 1.52-1.12 (m, 5H).

C088: N-(3-{3-[4-(2-Dimethylamino-ethoxy)-3',5'-dimethyl-biphenyl-3-yl]-(E)-acryloyl}-phenyl)-acetamide General procedure H gave the title compound as yellow crystals in 64% yield. $^1$H-NMR (DMSO-$d_6$) δ 10.15 (s, 1H), 8.23 (s, 1H), 8.10 (d, 1H), 8.02 (d, 2H), 7.92-7.82 (m, 2H), 7.69 (dd, 1H), 7.50 (t, 1H), 7.32 (s, 2H), 7.21 (d, 1H), 6.96 (s, 1H), 4.1 (t, 2H), 2.74 (t, 2H), 2.32 (s, 6H), 2.25 (s, 6H), 2.07 (s, 3H).

C089: (E)-3-[4-(2-Dimethylamino-ethoxy)-3',5'-dimethyl-biphenyl-3-yl]-1-(3-dimethylaminomethyl-phenyl)-propenone General procedure H gave the fumarate of the title compound as yellow crystals in 59% yield. $^1$H-NMR (DMSO-$d_6$) δ 8.14 (m, 2H), 8.10-8.01 (m, 3H), 7.70 (dd, 1H), 7.65 (dt, 1H), 7.57 (t, 1H), 7.33 (bs, 2H), 7.22 (d, 11H), 6.98 (bs, 1H), 6.57 (s, 4H), 4.34 (t, 2H), 3.77 (s, 2H), 3.05 (t, 2H), 2.48 (s, 6H), 2.35 (s, 6H), 2.34 (s, 6H).

C090: (E)-3-[4-(2-Dimethylamino-ethoxy)-3',5'-dimethyl-biphenyl-3-yl]-1-(3-dimethylaminomethyl-4-methoxy-phenyl)-propenone General procedure H gave the fumarate of the title compound as yellow crystals in 38% yield. $^1$H-NMR (DMSO-$d_6$) δ 8.23 (dd, 1H), 8.14-8.11 (m, 2H), 8.08 (d, 1H), 8.02 (d, 1H), 7.70 (dd, 1H), 7.34 (bs, 2H), 7.20 (t, 2H), 6.98 (bs, 2H), 6.56 (s, 4H), 4.31 (t, 2H), 3.92 (s, 3H), 3.74 (s, 2H), 2.97 (t, 2H), 2.42 (s, 6H), 2.37 (s, 6H), 2.35 (s, 6H).

C091: (E)-3-[4-(2-Dimethylamino-ethoxy)-3',5'-dimethyl-biphenyl-3-yl]-1-(2-dimethylaminomethyl-phenyl)-propenone General procedure H gave the title compound as off-white crystals in 58% yield. $^1$H-NMR (DMSO-$d_6$) δ 8.01 (d, 1H), 7.66 (dd, 1H), 7.59 (d, 1H), 7.46-7.36 (m, 5H), 7.32 (bs, 2H), 7.14 (d, 1H), 6.96 (bs, 1H), 4.12 (t, 2H), 3.50 (S; 2H, 2.59 (t, 2H), 2.33 (s, 6H), 2.11 (s, 6H), 2.03 (s, 6H).

C092: (E)-3-[4-(2-Dimethylamino-ethoxy)-3',5'-dimethyl-biphenyl-3-yl]-1-(2-dimethylaminomethyl-4-methoxy-phenyl)-propenone General procedure H gave the title compound as off-white crystals in 48% yield. $^1$H-NMR (DMSO-$d_6$) δ 8.01 (d, 1H), 7.68-7.63 (m, 2H), 7.51 (d, 1H), 7.47 (d, 1H), 7.32 (bs, 2H), 7.15 (d, 1H), 7.04 (d, 1H), 6.96 (bs, 1H), 6.92 (dd, 1H, 4.15 (t, 2H), 3.82 (s, 3H), 3.55 (s, 2H), 2.63 (t, 2H), 2.33 (s, 6H), 2.15 (s, 6H), 2.07 (s, 6H).

C093: (E)-1-(2-Amino-phenyl)-3-[4-(2-dimethylamino-ethoxy)-3',5'-dimethyl-biphenyl-3-yl]-propenone General procedure H gave the fumarate of the title compound as yellow crystals in 53% yield. $^1$H-NMR (DMSO-$d_6$) δ 8.18-8.05 (m, 3H), 7.94 (d, 1H), 7.66 (dd, 1H), 7.45-7.23 (m, 5H), 7.19 (d, 1H), 6.97 (s, 1H), 6.80 (d, 1H), 6.64-6.53 (m, 2H), 4.25 (t, 2H), 2.84 (t, 2), 2.33 (s, 6H).

C094: (E)-1-(4-Amino-phenyl)-3-[4-(2-dimethylamino-ethoxy)-3',5'-dimethyl-biphenyl-3-yl]-propenone General procedure H gave the fumarate of the title compound as yellow crystals in 20% yield. $^1$H-NMR (DMSO-$d_6$) δ 8.17-8.02 (m, 2H), 8.02-7.90 (m,3H), 7.68 (dd, 1H), 7.37 (s, 2H), 7.23 (d, 1H), 7.02 (s, 1H), 6.66 (d, 1H), 6.63 (s, 2H), 6.17 (s, 2H), 4.30 (t, 2H), 2.95 (t, 2H), 2.43 (s, 6H), 2.38 (s, 6H).

C095: (E)-3-[4-(2-Dimethylamino-ethoxy)-3',5'-dimethyl-biphenyl-3-yl]-1-(3-dimethylaminomethyl-4-hydroxy-phenyl)-propenone General procedure H gave the fumarate of the title compound as yellow crystals in 32% yield. $^1$H-NMR (DMSO-$d_6$) δ 8.06 (dd, 1H), 7.80-7.60 (m 3H), 7.53-7.41 (m, 1H), 7.39-7.22 (m, 3H), 7.17 (t, 1H), 7.04-6.85 (m, 2H), 6.59 (s, 2H), 4.20 (t, 2H), 2.70 (t, 2h), 2.31 (s, 6H), 2.20 (s, 6H), 2.05 (s, 6H).

C096: (E)-3-[4-(2-Dimethylamino-ethoxy)-2'-methoxy-biphenyl-3-yl]-1-[4-hydroxy-2-(4-methyl-piperazin-1-yl)-phenyl]-propenone General procedure H gave the fumarate of the title compound as yellow crystals in 6% yield. $^1$H-NMR (DMSO-$d_6$) δ 8.10-7.93 (m, 5H), 7.57 (dd, 1H), 7.43-7.35 (m, 2H), 7.21 (d, 1H), 7.17 (d, 1H), 7.08 (t, 1H), 6.95 (d, 1H), 6.63 (s, 4H), 4.40 (t, 2H), 3.80 (s, 3H), 3.74 (s, 2H), 3.18 (t, 2H), 2.78 (s, br, 4H), 2.65 (s, br, 4H), 2.60 (s, 6H), 2.44 (s, 3H).

C097: (E)-3-[2'-Chloro-4-(2-dimethylamino-ethoxy)-biphenyl-3-yl]-1-(4-methoxy-phenyl)-propenone General procedure H gave the fumarate of the title compound as off-white powder in 35% yield. $^1$H-NMR (DMSO-$d_6$) δ 8.16 (d, 2H), 8.02 (dd, 3H), 7.60-7.57 (m, 1H), 7.51-7.38 (m, 4H), 7.23 (d, 1H), 7.07 (d, 2H), 6.59 (s, 2H), 4.31 (t, 2H), 3.86 (s, 3H), 2.95 (t, 2H), 2.42 (s, 6H).

C098: (E)-3-[2'-Chloro-4-(2-dimethylamino-ethoxy)-biphenyl-3-yl]-1-(2-fluoro-4-methoxy-phenyl)-propenone General procedure H gave the fumarate of the title compound as yellow powder 10% yield. $^1$H-NMR (DMSO-$d_6$) δ 7.94 (d, 1H), 7.87-7.80 (m, 2H), 7.66 (dd, 1H), 7.59-7.37 (m, 5H), 7.24 (d, 1H), 6.99-6.89 (m, 2H), 6.59 (s, 3H), 4.32 (t, 2H), 3.86 (s, 3H), 2.99 (t, 2H), 2.42 (s, 6H).

C099: (E)-3-[4-(2-Dimethylamino-ethoxy)-3',5'-dimethyl-biphenyl-3-yl]-1-[4-hydroxy-3-(4-methyl-piperazin-1-ylmethyl)-phenyl]-propenone General procedure H gave the title compound as off-white powder in 58% yield. $^1$H-NMR (DMSO-$d_6$) δ 7.99 (d, 1H), 7.66 (dd, 1H), 7.57 (d, 1H), 7.43-7.35 (m, 4H), 7.14 (d, 1H), 6.96 (bs, 1H), 4.12 (t, 2H), 3.53 (s, 2H), 2.58 (t, 2H) 2.50 (t, 4H), 2.33 (s, 6H), 2.24 (bs, 4H), 2.11 (s, 6H), 1.99 (s, 3H).

C100: (E)-3-[4-(2-Dimethylamino-ethoxy)-3',5'-dimethyl-biphenyl-3-yl]-1-[4-(2-dimethylamino-ethylamino)-phenyl]-propenone General procedure H gave the oxalate of the title compound as yellow crystals in 27% yield. $^1$H-NMR (DMSO-$d_6$) δ 8.20 (d, 1H), 8.05-8.02 (m, 4H), 7.69 (dd, 1H), 7.35 (bs, 2H), 7.22 (d, 1H), 6.99 (bs, 1H), 6.93 (bs, 1H), 6.73 (d, 2H), 4.47 (t, 2), 3.56-3.51 (m, 4H), 3.20 (t, 2H), 2.83 (s, 6H), 2.78 (s, 6H), 2.36 (s, 6H).

C101: (E)-3-[4-(2-Dimethylamino-ethoxy)-3',5'-dimethyl-biphenyl-3-yl]-1-[2-(2-dimethylamino-ethoxy)-phenyl]-propenone General procedure H gave the oxalate of the title compound as yellow powder in 14% yield. $^1$H-NMR (DMSO-$d_6$) δ 8.09 (d, 1H), 7.82 (d, 1H), 7.73 (dd, 1H), 7.58-7.49 (m, 3H), 7.33 (bs, 2H), 7.24-7.20 (m, 2H), 7.12 (t, 1H), 6.98 (bs, 1H), 4.44-443 (m, 4H), 3.46 (t, 2H), 3.36 (t, 2H), 2.75 (s, 6H), 2.65 (s, 6H), 2.33 (s, 6H).

C102: (E)-3-[4-(2-Dimethylamino-ethoxy)-3',5'-dimethyl-biphenyl-3-yl]-1-(3-hexyloxy-phenyl)-propenone General procedure H gave the fumarate of the title compound as yellow crystals in 33% yield $^1$H-NMR (DMSO-$d_6$) δ 8.17 (d, 1H). 8.06 (bs, 2H). 7.75 (d, 1H). 7.70 (dd, 1H). 7.59 (bs, 1H). 7.47 (t, 1H). 7.33 (bs, 2H). 7.24-7.19 (m, 2H). 6.97 (s, 1H). 6.59 (s, 2H). 4.31 (t, 2H). 4.04 (t, 2H). 2.99 (t, 2H). 2.44 (s, 6H). 2.34 (s, 6H). 1.73 (p, 2H). 1.43 (p, 2H). 1.34-1.29 (m, 4H). 0.87 (t, 3H).

C103: (E)-3-[4-(2-Dimethylamino-ethoxy)-3',5'-dimethyl-biphenyl-3-yl]-1-[3-(4-methyl-piperazin-1-yl)-phenyl]-propenone General procedure H gave the fumarate of the title compound as yellow crystals in 34% yield. $^1$H-NMR (DMSO-$d_6$) δ 8.16 (d, 1H), 8.04 (d, 2H), 7.72 (dd, 1H), 7.63 (d, 1H), 7.55 (bs, 1H), 7.42 (t, 1H), 7.34 (s, 2H), 7.27 (dd, 1H), 7.22 (d, 1H), 6.98 (s, 1H), 6.67 (d, 1H), 6.59 (s, 2H), 4.32 (t, 2H), 3.33-3.27 (m, 4H), 3.04 (t, 2H), 2.69-2.64 (m, 4H). 2.47 (s, 6H), 2.36 (s, 3H), 2.34 (s, 6H).

C104: (E)-3-[4-(2-Dimethylamino-ethoxy)-3',5'-dimethyl-biphenyl-3-yl]-1-[2-(3-dimethylamino-propoxy)-phenyl]-propenone General procedure H gave the fumarate of the title compound as yellow crystals in 57% yield. $^1$H-NMR (DMSO-$d_6$) δ 8.06 (d, 1H), 7.82 (d, 1H), 7.69 (dd, 1H), 7.57 (d, 1H), 7.51 (d, 1H), 7.47 (dd, 1H), 7.31 (s, 2H), 7.18 (q, 2H), 7.08 (t, 1H), 6.96 (s, 1H),6.55 (s, 4H), 4.29 (t, 2H), 4.13 (t, 2H), 2.93 (t, 2H),2.74 (t, 2H), 2.37 (s, 6H), 2.33 (s, 6H), 2.25 (s, 6H), 1.96 (p, 2H).

C105: (E)-3-[4-(2-dimethylamino-ethoxy)-3',5'-dimethyl-biphenyl-3-yl]-1-(2-fluoro-4-hydroxy-phenyl)-propenone General procedure H gave the title compound as yellow powder in 26% yield. $^1$H-NMR (DMSO-$d_6$) δ 10.82 (bs, 1H), 8.99 (d, 2H), 7.90 (bd, 1H), 7.78-7.66 (m, 3H), 7.33 (s, 2H), 7.19 (d, 1H), 6.97 (bs, 1H), 6.74 (dd, 1H), 6.66 (dd, 1H), 4,20 (t,2H), 2.72 (t, 2H), 2.33 (s, 6H), 2.33 (s, 6H).

C106: (E)-1-(6-Amino-benzo[1,3]dioxol-5-yl)-3-[4-(2-dimethylamino-ethoxy)-3',5'-dimethyl-biphenyl-3-yl]-propenone General procedure H gave the fumarate of the title compound as orange powder in 60% yield. $^1$H-NMR (DMSO-$d_6$) δ 8.13 (d, 1H), 8.04 (d, 1H), 0.91 (d, 1H), 7.76-7.67 (m, 3H), 7.64 (dd, 1H), 7.33 (s, 2H), 7.18 (d, 1H), 6.98 (s, 2H), 6.60 (s, 2H), 6.37 (s, 1H), 5.97 (s, 2H), 4.26 (t, 2H), 2.90 (t, 2H), 2.39 (s, 6H), 2.35 (s, 6H).

C107: (E)-3-[4-(2-Dimethylamino-ethoxy)-3',5'-dimethyl-biphenyl-3-yl]-1-phenyl-propenone General procedure H gave the title compound as yellow powder in 35% yield. $^1$H-NMR (DMSO-$d_6$) δ 8.22-8.12 (m, 3H), 8.05 (d, 1H), 7.82-7.62 (m, 3H), 7.61-7.55 (m, 2H), 7.40-7.32 (m, 2H), 7.21 (d, 1H), 6.98 (s, 1H), 4.23 (t, 2H), 2.74 (t, 2H), 2.35 (s, 6H), 2.27 (s, 6H).

C108: (E)-3-[4-(2-Dimethylamino-ethoxy)-2'-methyl-biphenyl-3-yl]-1-(3-dimethylaminomethyl-4-hydroxy-phenyl)-propenone General procedure H gave the fumarate of the title product as yellow foam in 14% yield. $^1$H-NMR (DMSO-$d_6$) δ 8.07-7.97 (m, 4H), 7.90 (d, 1H), 7.37 (dd, 1H), 7.27-7.24 (m, 4H), 7.20 (d, 1H), 6.89 (d, 1H), 6.59 (s, 4H), 4.29 (t, 2H), 3.81 (br s, 2H), 2.94 (br t, 2H), 2.41 (d, 6H), 2.37 (s, 6H), 2.27 (s, 3H).

C109: (E)-3-[4-(2-Dimethylamino-ethoxy)-2'-methyl-biphenyl-3-yl]-1-(3-dimethylaminomethyl-4-methoxy-phenyl)-propenone General procedure H gave the fumarate of the title product as yellow powder in 32% yield. $^1$H-NMR (DMSO-$d_6$) δ 8.22 (dd, 1H), 8.11 (d, 1H), 8.03 (dd, 2H), 7,90 (d, 1H), 7.39 (dd, 1H), 7.32-7.25 (m, 4H), 7.21 (d, 1H), 7.14 (d, 1H), 6.57 (s, 4H), 4.30 (t, 2H), 3.90 (s, 3H), 3.69 (s, 2H), 2.95 (t, 2H), 2.41 (s, 6H), 2.33 (s, 6H), 2.27 (s, 3H).

C110: 2-Dimethylamino-N-(3-{3-[4-(2-dimethylamino-ethoxy)-2'-methyl-biphenyl-3-yl]-(E)-acryloyl}-phenyl)-acetamide General procedure H gave the fumarate of the title product as yellow powder in 21% yield. $^1$H-NMR (DMSO-$d_6$) δ 10.04 (br s, 1H), 8.33 (t, 1H), 8.09 (d, 1H), 7.96 (d, 1H), 7.96 (d, 1H), 4.35 (t, 2H), 7.92-7.86 (m, 2H), 7.49 (t, 1H), 7.41 (dd, 1H), 7.33-7.20 (m, 5H), 5.59 (s, 4H), 4.35 (t, 2H), 3.20 (s, 2H), 3.07 (t, 2H), 2.49 (s, 6H), 2.34 (s, 6H), 2.27 (s, 3H).

C111: (E)-3-[4-(4-Dimethylamino-butoxy)-2'-methyl-biphenyl-3-yl]-1-(2-dimethylaminomethyl-phenyl)-propenone General procedure H gave the title product as yellow oil in 25% yield. $^1$H-NMR (CDCl$_3$) δ 7.65 (d, 1H), 7.53 (d, 1H), 7.44-7.38 (m, 3H), 7.33 (dd, 1H), 7.30-7.22 (m, 5H), 7.13 (d, 1H), 6.95 (d, 1H), 4.07 (t 2H), 3.57 (s, 2H), 2.33 (t, 2H), 2.30 (s, 3H), 2.25 (s, 6H), 2.16 (s, 6H), 1.83 (p, 2H), 1.61 (p, 2H).

C112: (E)-3-[2'-Chloro-4-(2-dimethylamino-ethoxy)-biphenyl-3-yl]-1-(2-dimethylaminomethyl-5-methoxy-phenyl)-propenone General procedure H gave the fumarate of the title product as yellow crystals in 40% yield. $^1$H-NMR (DMSO-$d_6$) δ 7.81 (d, 1H), 7.81 (d, 1H), 7.59-7.36 (m, 8H), 7.20 (t, 2H), 6.58 (s, 4H), 4.28 (t, 2H), 3.85 (s; 3H), 3.71 (s, 2H), 2.90 (t, 2H), 2.35 (s, 6H), 2.34 (s, 6H).

C113: (E)-3-[4-(2-Dimethylamino-ethoxy)-2'-methyl-biphenyl-3-yl]-1-(2-dimethylaminomethyl-5-methoxy-phenyl)-propenone General procedure H gave the hydrochloride of the title product as yellow powder in 8% yield. $^1$H-NMR (DMSO-$d_6$)

δ 11.10 (br, 1H), 10.95 (br, 1H), 7.86 (d, 1H), 7.80-7.68 (m, 3H), 7.46 (d, 1H), 7.44 (dd, 1H), 7.31-7.20 (m, 6H), 4.55 (t, 2H), 4.26 (d, 2H), 3.86 (s, 3H), 3.61-3.53 (m, 2H), 2.83 (d, 6H), 2.66.(d, 6H), 2.26 (s, 3H).

C114: (E)-3-[4-(2-Dimethylamino-ethoxy)-2'-methyl-biphenyl-3-yl]-1-(2-imethylaminomethyl-4-methoxy-phenyl )-propenone General procedure H gave the hydrochloride of the title product as yellow powder in 22% yield. $^1$H-NMR (DMSO-$d_6$) δ 11.29 (br, 1H), 9.56 (br, 1H), 8.29 (d, 1H), 8.08 (d, 1H), 8.02 (d, 1H), 7.85 (d, 1H), 7.46 (dd, 1H), 7.40 (d, 1H), 7.33-7.23 (m, 5H), 7.17 (dd, 1H), 4.59 (t, 2H), 4.44 (d, 2H), 3.91 (s, 3H), 3.62-3.56 (m, 2H), 2.87 (d, 6H), 2.80 (d, 6H), 2.27 (s, 3H).

C115: (E)-3-[5-(1,1-Dimethyl-allyl)-2-(2-dimethylamino-ethoxy)-phenyl]-1-[4-(tetrahydro-pyran-2-yloxy)-phenyl]-propenone General procedure H gave the fumarate of the title product as white crystals in 41% yield. $^1$H-NMR (DMSO-$d_6$) δ 8.11 (d, 2H), 8.01 (d, 1H), 7.92 (d, 1H), 7.74 (d, 1H), 7.34 (dd, 1H), 7.17 (d, 2H), 7.07 (d, 1H), 6.60 (s, 2H), 6.06 (dd, 1H), 5.65 (br, 1H), 5.06 (dd, 1H), 5.01 (s, 1H), 3.78-3.70 (m, 1H), 4.25-4.18 (m, 2H), 2.85-2.72 (m, 2H), 2.32 (s, 6H), 1.40 (s, 6H).

C116: 3-[5-(1,1-Dimethyl-allyl)-2-(2-dimethylamino-ethoxy)-phenyl]-1-(4-hydroxy-phenyl)-propenone The fumarate of 3-[5-(1,1-Dimethyl-allyl)-2-(2-dimethylamino-ethoxy)-phenyl]-1-[4-(tetrahydro-pyran-2-yloxy)-phenyl]-propenone was suspended in $H_2O$ and MeOH was added to give a solution. Stirred at 55° C. for 72 hr, until the deprotection was complete according to TLC. Co-evaporation of the solvent with MeCN gave a yellow solid. Recrystallisation from $H_2O$ gave the fumarate of the title compound as yellow crystals in 51% yield. LCMS and $^1$H-NMR showed a mixture of E- and Z- isomers in approximately 1:1 ratio. $^1$H-NMR (DMSO-$d_6$) δ 8.03 (d, 2H), 7.97 (d, 1H), 7.89 (d, 1H), 7.72 (d, 1H), 7.69 (s, 1H), 7.66 (s, 2H), 7.33 (dd, 1H), 7.11 (dd, 1H), 7.06 (d, 1H), 7.05 (s, 2H), 6.90 (d, 2H), 6.81 (d, 1H), 6.73 (d, 2H), 6.58)s, 4H), 6.06 (dd, 1H), 5.89 (dd, 1H), 5.03 (dd, 1H), 4.86 (dd, 1H), 4.54 (t, 1H), 4.20 (t, 2H), 3.97 (t, 1H), 3.72 (t, 2H), 2.86 (t, 2H), 2.36 (s, 6H), 2.29 (t, 2H), 2.11 (s, 6H), 1.40 (s, 6H), 1.22 (s, 6H).

C117: (E)-3-[6-(2-Dimethylamino-ethoxy)-2,3,3-trimethyl-2,3-dihydro-benzofuran-5-yl]-1-(2-dimethylaminomethyl-phenyl)-propenone General procedure H gave the fumarate of the title product as yellow crystals in 55% yield. $^1$H-NMR (DMSO-$d_6$) δ 7.70 (s, 1H), 7.62 (d, 1H), 7.50-7.40 (m, 4H), 7.18 (d, 1H), 6.59 (s, 4H), 6.55 (s, 1H), 4.44 (q, 1H), 4.09 (t, 2H), 3.62 (s, 2H), 2.74 (t, 2H), 2.23 (s, 6H), 2.17 (s, 6H), 1.31 (d, 3H), 1.30 (s, 3H), 1.06 (s, 3H).

C118: (E)-3-[4-(2-Dimethylamino-ethoxy)-2'-methyl-biphenyl-3-yl]-1-(2-{[(2-dimethylamino-ethyl)-methyl-amino]-methyl}-phenyl)-propenone General procedure H gave the fumarate of the title product as brown crystals in 44% yield. $^1$H-NMR (DMSO-$d_6$) δ 7.78 (d, 1H), 7.68 (d, 1H), 7.50-7.43 (m, 3H), 7.41-7.35 (m, 2H), 7.35 (d, 1H), 7.30-7.20 (m, 4H), 7.15 (d, 1H), 6.54 (s, 6H), 4.22 (t, 2H), 3.64 (s, 2H), 2.81 (m, 4H), 2.54 (t, 2H), 2.44 (s, 6H), 2.28 (s, 6H), 2.25 (s, 3H), 2.01 (s, 3H).

C119: (E)-3-[4-(2-Dimethylamino-ethoxy)-2'-methyl-biphenyl-3-yl]-1-(2-pyrrolidin-1-ylmethyl-phenyl)-propenone General procedure H gave the fumarate of the title product as yellow crystals in 23% yield. $^1$H-NMR (DMSO-$d_6$) δ 7.77 (d, 1H), 7.68 (d, 1H), 7.54 (d, 1H), 7.51-7.47 (m, 2H), 7.44-7.34 (m, 3H), 7.30-7.20 m, 4H), 7.16 (d, 1H), 6.58 (s, 4H), 4.24 (t, 2H), 3.87 (s, 2H), 2.86 (t, 2H), 2.57 (br t, 4H), 2.31 (s, 6H), 2.24 (s, 3H), 1.64 (br p, 4H).

C120: (E)-1-{2-[(tert-Butyl-methyl-amino)-methyl]-phenyl}-3-[4-(2-dimethylamino-ethoxy)-2'-methyl-biphenyl-3-yl]-propenone General procedure H gave the title product as yellow oil in 17% yield. $^1$H-NMR (DMSO-$d_6$) δ 7.70 (d, 1H), 7.60 (d, 1H), 7.49 (d, 1H), 7.45-7.20 (m, 9H), 7.13 (d, 1H), 4.12 (t, 2H), 3.61 (s, 2H), 2.58 (t, 2H), 2.24 (s, 3H), 2.11 (s, 6H), 1.86 (s, 3H), 0.98 (s, 9H).

C121: (E)-3-[4-(2-Dimethylamino-ethoxy)-2'-trifluoromethoxy-biphenyl-3-yl]-1-(2-dimethylaminomethyl-phenyl)-propenone General procedure H gave the title product as yellow crystals in 43% yield. $^1$H-NMR (DMSO-$d_6$) δ 7.86 (d, 1H), 7.61-7.56 (m, 2H), 7.51 (d, 1H), 7.51 (d, 1H), 7.49-7.35 (m, 6H), 7.27 (d, 1H), 7.18 (d, 1H), 4.14 (t, 2H), 3.49 (s, 2H), 2.59 (t, 2H), 2.11 (s, 6H), 2.01 (s, 6H).

C122: (E)-3-[2'-tert-Butoxymethyl-4-(2-dimethylamino-ethoxy)-biphenyl-3-y]-1-(2-dimethylaminomethyl-phenyl)-propenone General procedure H gave the title product as green oil in 28% yield. $^1$H-NMR (DMSO-$d_6$) δ 7.80 (d, 1H), 7.56 (d, 1H), 7.46-7.40 (m, 4H), 7.37-7.32 (m, 4H), 7.30-7.26 (m, 1H), 7.23 (d, 1H), 7.15 (d, 1H), 4.24 (s, 2H), 4.13 (t, 2H), 3.47 (s, 2H), 2.59 (t, 2H), 2.12 (s, 6H), 2.01 (s, 6H), 1.10 (s, 9H).

C123: (E)-3-[4-(Z-Dimethylaminoethoxy)-2',5'-dimethoxy-biphenyl-3-yl]-1-(2-dimethylaminomethyl-phenyl)-propenone General procedure H gave the title product as yellow crystals in 27% yield. $^1$H-NMR (CDCl$_3$) δ 7.78 (d, 1H), 7.64 (d, 1H), 7.54 (dd, 1H), 7.49-7.32 (m, 4H), 7.16 (d, 1H), 6.97-6.84 (m, 4H), 4.15 (t, 2H), 3.83 (s, 3H), 3.78 (s, 3H), 3.61 (s, 2H), 2.73 (t, 2H), 2.27 (s, 6H), 2.18 (s, 6H).

C124: (E)-3-[4-(2-Dimethylamino-ethoxy)-2',4'-dimethoxy-biphenyl-3-yl]-1-(2-dimethylaminomethyl-phenyl)-propenone General procedure H gave the title product as green crystals in 36% yield. $^1$H-NMR (DMSO-$d_6$) δ 7.75 (d, 1H), 7.56 (d, 1H), 7.48-7.35 (m, 5H), 7.24 (d, 1H), 7.23 (d, 1H), 7.08 (d, 1H), 6.66 (d, 1H), 6.60 (dd, 1H), 4.11 (t, 2H), 3.80 (s, 3H), 3.76 (s, 3H), 3.50 (s, 2H), 2.58 (t, 2H), 2.11 (s, 6H), 2.02 (s, 6H).

C125: (E)-3-[4-(2-Dimethylamino-ethoxy)-2',4',6'-trimethyl-biphenyl-3-yl]-1-(2-dimethylaminomethyl-phenyl)-propenone General procedure H gave the title product as yellow oil in 52% yield. $^1$H-NMR (DMSO-d$_6$) δ 7.60 (d, 1H), 7.52 (br s, 1H), 7.46-7.31 (m, 4H), 7.26 (d, 1H), 7.12 (br s, 2H), 6.92 (br s, 2H), 4.12 (t, 2H), 3.49 (s, 2H), 2.59 (t, 2H), 2.26 (s, 3H), 2.11 (s, 6H), 2.02 (s, 6H), 1.95 (s, 6H).

C126: (E)-3-[4-(2-Dimethylamino-ethoxy)-2'-methoxymethyl-biphenyl-3-yl]-1-(2-dimethylaminomethyl-phenyl)-propenone General procedure H gave the title product as green crystals in 21% yield. $^1$H-NMR (DMSO-d$_6$) δ 7.76 (d, 1H), 7.58 (d, 1H), 7.51-7.30 (m, 9H), 7.25 (d, 1H), 7.15 (d, 1H), 4.30 (s, 2H), 4.13 (t, 2H), 3.49 (s, 2H), 3.24 (s, 3H), 2.60 (t, 2H), 2.12,(s, 6H), 2.02 (s, 6H).

C127: (E)-3-[4-(2-Dimethylamino-ethoxy)-2',6'-dimethoxy-biphenyl-3-yl]-1-(2-dimethylaminomethyl-phenyl)-propenone General procedure H gave the title product as green crystals in 84% yield. $^1$H-NMR (DMSO-d$_6$) δ 7.57 (d, 1H), 7.54 (d, 1H), 7.45-7.20 (m, 7H), 7.15 (d, 1H), 7.06 (d, 1H), 6.75 (s, 1H), 6.73 (s, 1H), 4.11 (t, 2H), 3.67 (s, 6H), 3.49 (s, 2H), 2.59 (t, 2H), 2.12 (s, 6H), 2.02 (s, 6H).

C128: (E)-3-[2'-Chloro-4-(2-dimethylamino-ethoxy)-biphenyl-3-yl]-1-(2-dimethylaminomethyl-phenyl)-propenone General procedure H gave the title product as yellow oil in 18% yield. $^1$H-NMR (DMSO-d$_6$) δ 7.82 (d, 1H), 7.48 (d, 1H), 7.58-7.54 (m, 1H), 749-7.35 (m, 8H), 7.28 (d, 1H), 7.17 (d, 1H), 4.15 (t, 2H), 3.50 (s, 2H), 2.60 (t, 2H), 2.12 (s, 6H), 2.02 (s, 6H).

C129: (E)-3-[4-(2-Dimethylamino-ethoxy)-2'-methylsulfanyl-biphenyl-3-yl]-1-(2-dimethylaminomethyl-phenyl)-propenone General procedure H gave the title product as yellow oil in 25% yield. $^1$H-NMR (DMSO-d$_6$) δ 7.73 (d, 1H), 7.57 (d, 1H), 7.45-7.31 (m, 7H), 7.23 (d, 1H), 7.24-7.20 (m, 2H), 7.13 (d, 1H), 4.13 (t, 2H), 3.49 (s, 2H), 2.59 (t, 2H), 2.37 (s, 3H), 2.12 (s, 6H), 2.02 (s, 6H).

C130: (E)-3-[4-(2-Dimethylamino-ethoxy)-2'-trifluoromethyl-biphenyl-3-yl]-1-(2-dimethylaminomethyl-phenyl)-propenone General procedure H gave the title product as yellow oil in 43% yield. $^1$H-NMR (DMSO-d$_6$) δ 7.83 (d, 1H), 7.75-7.68 (m, 2H), 7.61 (t, 1H), 7.56 (d, 1H), 7.47-7.30 (m, 6H), 7.23 (d, 1H), 7.14 (d, 1H), 4.14 (t, 2H), 3.49 (s, 2H), 2.60 (t, 2H), 2.12 (s, 6H), 2.02 (s, 6H).

C131: (E)-3-[4-(2-Dimethylamino-ethoxy)-2'-hydroxy-biphenyl-3-yl]-1-(2-dimethylaminomethyl-phenyl)-propenone General procedure H gave, the title product as yellow crystals in 14% yield. $^1$H-NMR (DMSO-d$_6$) δ 9.55 (br, 1H), 7.87 (d, 1H), 7.59 (dd, 1H), 7,47 (d, 1H), 7.47-7.35 (m, 4H), 7.30 (dd, 1H), 7.22 (d, 1H), 7.15 (td, 1H), 7.11 (d, 1H), 6.93 (dd, 1H), 6.87 (td, 1H), 4.12 (t, 2H), 3.49 (s, 2H), 2.59 (t, 2H), 2,12 (s, 6H), 2.03 (s, 6H).

C132: (E)-3-[4-(2-Dimethylamino-ethoxy)-2'-ethyl-biphenyl-3-yl]-1-(2-dimethylaminomethyl-phenyl)-propenone General procedure H gave the title product as yellow oil in 35% yield. $^1$H-NMR (DMSO-d$_6$) δ 7.69 (d, 1H), 7.60 (d, 1H), 7.45-7.10 (m, 11H), 4.13 (t, 2H), 3.49 (s, 2H), 2.59 (t, 2H), 2.59 (q, 2H), 2.12 (s, 6H), 2.02 (s, 6H), 1.98 (t, 3H).

C133: (E)-3-[2',6'-Dichloro-4-(2-dimethylamino-ethoxy)-biphenyl-3-yl]-1-(2-dimethylaminomethyl-phenyl)-propenone General procedure H gave the title product as yellow oil in 14% yield. $^1$H-NMR (DMSO-d$_6$) δ 7.73 (d, 1H), 7.60 (d, 1H), 7.59 (d, 1H), 7.57 (d, 1H), 7.46-7.35 (m, 5H), 7.29 (dd, 1H), 7.28 (d, 1H), 7,17 (d, 1H), 4.15 (t, 2H), 3.50 (s, 2H), 2.61 (t, 2H), 2.12 (s, 6H), 2.02 (s, 6H).

C134: (E)-3-[4-(2-Dimethylamino-ethoxy)-2',6'-difluoro-biphenyl3-yl]1-(2-dimethylaminomethyl-phenyl)-propenone General procedure H gave the title product as yellow crystals in 11% yield. $^1$H-NMR (DMSO-d,) δ 7.93 (br s, 1H), 7.65 (d, 1H), 7.52-7.40 (m, 6H), 7.35 (d, 1H), 7.25-7.18 (m, 3H), 6.58 (s, 4H), 4.24 (t, 2H), 3.63 (s, 2H), 2.83 (t, 2H), 2.27 (s, 6H), 2.13 (s, 6H).

C135: (E)-3-{4-[2-(tert-Butyl-methyl-amino)-ethoxy]-2'-methyl-biphenyl-3-yl}-1-(2-dimethylaminomethyl-phenyl)-propenone General procedure H gave the title compound as yellow crystals in 15% yield. $^1$H-NMR (CDCl$_3$) δ 7.48 (d, 1H), 7.33 (d, 1H), 7.22-7.01 (m, 9H), 6.90 (d, 1H), 6.76 (d, 1H), 3.92 (bs, 2H), 3.38 (s, 2H), 2.62 (bs, H), 2.08 (s, 6H), 1.97 (s, 6H), 0.90 (s, 9H).

C136: (E)-1-(2-Dimethylaminomethyl-phenyl)-3-[2'-methyl-4-(2-pyrrolidin-1-yl-ethoxy)-biphenyl-3-yl]-propenone General procedure H gave the hydrochloride of the title compound as yellow crystals in 55% yield. $^1$H-NMR (DMSO-d$_6$) δ 11.53 (bs, 1H), 9.63 (bs, 1H), 8.20 (d, 1H), 8.08 (d, 1H), 8.02 (d, 1H), 7.80-7.65 (m, 4H), 7.47 (dd, 1H), 7.34-7.24 (m, 5H), 4.5 (t, 2H), 4.42 (d, 2H), 3.67-3.59 (m, 4H), 3.12-3.09 (m, 2H), 2.79 (d, 6H), 2.27 (s, 3H), 2.02-1.89 (m, 4H).

C137: (E)-3-[4-(2-Diethylamino-ethoxy)-2'-methyl-biphenyl-3-yl]-1-(2-dimethylaminomethyl-phenyl)-propenone General procedure H gave the hydrochloride of the title compound as yellow crystals in 46% yield. $^1$H-NMR (DMSO-d$_6$) δ 11.21 (bs, 1H), 9.71 (bs, 1H), 8.20 (d, 1H), 8.07 (d, 1H), 8.02 (d, 1H), 7.82-7.65 (m, 4H), 7.47 (dd, 1H), 7.34-7.23 (m, 5H), 4.5 (t, 2H), 4.41 (d, 2H), 3.59-3.57 (m, 2H), 3.27-3.19 (m, 4H), 2.79 (d, 6H), 2.27 (s, 3H), 1.30 (t, 6H).

C138: (E)-3-[4-(3-Dimethylamino-propoxy)-2'-methyl-biphenyl-3-yl]-1-(2-fluoro-4-methoxy-phenyl)-propenone General procedure H gave the fumarate of the title compound as colourless crystals in 7% yield. $^1$H-NMR (DMSO-d$_6$) δ 7.94 (d, 1H), 7.84 (t, 1H), 7.74 (d, 1H), 7.64 (dd, 2H), 7.39 (dd, 1H), 7.31-7.21 (m, 40), 7.18 (d, 1H), 6.98-6.90 (m, 2H), 6.56 s, 2H), 4.19 (t, 2H), 2.71 (t, 2H), 2.50 (s, 6H), 2.38 (s, 3H), 2.08-2.03 (m, 2H).

C139: (E)-3-[4-(2-Dimethylamino-ethoxy)-2'-methoxy-biphenyl-3-yl]-1-(3-fluoro-4-hydroxy-phenyl)-propenone General procedure H gave the title compound as yellow crystals in 22% yield. $^1$H-NMR (DMSO-d$_6$) δ 8.01-7.86 (m, 5H), 7.53 (dd, 1H), 7.36-7.31 (m, 2H), 7.18-7.01 (m, 4H), 4.25 (t, 2H), 3.77 (s, 3H), 2.84 (t, 2H), 2.34 (s, 6H).

C140: (E)-3-[4-(2-Dimethylamino-ethoxy)-3',5'-dimethyl-biphenyl-3-yl]-1-(3-fluoro-4-hydroxy-phenyl)-propenone General procedure H gave the title compound as yellow crystals in 22% yield. $^1$H-NMR (CDCl$_3$) δ 8.26 (d, 1H), 8.12 (d, 1H), 8.03-7.94 (m, 3H), 7.72 (dd, 1H), 7.35 (bs, 2H), 7.24 (d, 1H), 7.15 (t, 1H), 7.00 (bs, 1H), 4.52 (t, 2H), 3.58 (t, 2H), 2.87 (s, 6H), 2.36 (s, 6H).

C141: (E)-3-[5-tert-Butyl-2-(2-dimethylamino-ethoxy)-phenyl]-1-(3-fluoro-4-hydroxy-phenyl)-propenone General procedure H gave the title compound as yellow crystals in 22% yield. $^1$H-NMR (CDCl$_3$) δ 11.00 (s, 1H), 10.69 (bs, 1H), 8.08 (d, 1H), 7.99-7.91 (m, 3H), 7.86 (d, 1H), 7.16 (t, 1H), 7.09 (d, 1H), 4.47 (t, 2H), 3.59 (t, 2H), 2.88 (s, 6H), 1.34 (s, 9H).

C142: (E)-3-[2-(2-Dimethylamino-ethoxy)-5-methyl-phenyl]-1-(3-fluoro-4-hydroxy-phenyl)-propenone General procedure H gave the title compound as yellow crystals in 46% yield. $^1$H-NMR (DMSO-d$_6$) δ 8.05 (d, 1H), 7.98-7.89 (m, 3H), 7.85 (d, 1H), 7.28 (dd, 1H), 7.13 (t, 1H), 7.06 (d, 1H), 4.44 (t, 2H), 3.57 (t, 2H), 2.87 (s, 6H), 2.32 (s, 3H).

C143: (E)-3-[2-(2-Dimethylamino-ethoxy)-5-methyl-phenyl]-1-(3-fluoro-4-methoxy-phenyl)-propenone General procedure H gave the title compound as yellow crystals in 12% yield. $^1$H-NMR (CDCl$_3$) δ 8.04 (d, 1H), 7.92-7.84 (m, 3H), 7.77 (d, 1H), 7.42 (d, 1H), 7.17 (dd, 1H), 7.05 (t, 1H), 6.87 (d, 1H), 4.17 (t, 2H), 3.99 (s, 3H), 2.85 (t, 2H), 2.39 (s, 6H), 2.34 (s, 3H).

C144: (E)-3-[5-tert-Butyl-2-(2-dimethylamino-ethoxy)-phenyl]-1-(3-fluoro-4-methoxy-phenyl)-propenone General procedure H gave the title compound as yellow crystals in 20% yield. $^1$H-NMR (CDCl$_3$) δ 8.04 (d, 1H), 7.92-7.87 (m, 2H), 7.83 (d, 1H), 7.61 (d, 1H), 7.42 (dd, 1H), 7.07 (t, 1H), 6.93 (d, 1H), 4.21 (t, 2H), 4.01 (s, 3H), 2.88 (t, 21H), 2.41 (s, 6H), 1.37 (s, 9H).

C145: (E)-3-[4-(2-Dimethylamino-ethoxy)-3',5'-dimethyl-biphenyl-3-yl]-1-(3-fluoro-4-methoxy-phenyl)-propenone General procedure H gave the title compound as yellow crystals in 20% yield. $^1$H-NMR (CDCl$_3$) δ 7.97 (d, 1H), 7.79-7.66 (m, 4H), 7.44 (dd, 1H), 7.06 (bs, 2H), 6.94-6.87 (m, 3H), 4.12 (t, 2H), 3.85 (s, 3H), 2.78 (t, 2H), 2.30 (s, 6H), 2.27 (s, 6H).

C146: (E)-3-(2,4-Dichloro-phenyl)-1-[4-(2-dimethylamino-ethoxy)-phenyl]-propenone General procedure H, gave the title compound as yellow crystals in 36% yield. $^1$H-NMR (CDCl$_3$) δ 7.94 (d, 1H), 7.87 (d, 2H), 7.53 (d, 1H), 7.33 (d, 1H), 7.32 (d, 1H), 7.15 (dd, 1H), 6.86 (d, 2H), 4.03 (t, 2H), 2.65 (t, 2H), 2.23 (s, 6H).

C147: (E)-3-{4-[5-(tert-Butyl-methyl-amino)-pentyloxy]-2'-methyl-biphenyl-3-yl}-1-(2-dimethylaminomethyl-phenyl)-propenone General procedure H gave the title compound as yellow/brown oil in 22% yield. $^1$H-NMR (CDCl$_3$) δ 7.43 (d, 1H), 7.31 (d, 1H), 7.19-7.01 (m, 9H), 6.90 (d, 1H), 6.72 (d, 1H), 3.82 (t, 2H), 3.34 (s, 2H), 2.14-2.08 (m, 5H), 2.00 (s, 3H), 1.93 (s, 6H), 1.61 (m, 2H), 1.28-1.08 (m, 4H), 0.86 (s, 9H).

C148: (E)-3-[4-(4-Diethylamino-butoxy)-2'-methyl-biphenyl-3-yl]-1-(2-dimethylaminomethyl-phenyl)-propenone General procedure H gave the title compound as yellow/brown oil In 32% yield. $^1$H-NMR (CDCl$_3$) δ 7.52 (d, 1H), 7.37 (d, 1H), 7.28-7.06 (m, 9H), 6.99 (d, 1H), 6.80 (d, 1H), 3.92 (t, 2H), 3.42 (s, 2H), 2.43-2.34 (m, 6H), 2.14 (s, 3H)) 2.00 (s, 6H), 1.70-1.66 (m, 2H), 1.49 (bs, 2H), 0.92 (t, 6H).

C149: (E)-3-{4-[4-(tert-Butyl-methyl-amino)-butoxy]-2'-methyl-biphenyl-3-yl}-1-(2-dimethylaminomethyl-phenyl)-propenone General procedure H gave the title compound as yellow/brown oil in 65% yield. $^1$H-NMR (CDCl$_3$) δ 7.53 (d, 1H), 7.40 (d, 1H), 7.29-7.10 (m, 9H), 7.02 (d, 1H), 6.83 (d, 1H), 3.94 (t, 2H), 3.44 (s, 2H), 2.26 (t, 2H), 2.17 (s, 3H), 2.06 (s, 3H), 2.03 (s, 6H), 1.72-1.67 (m, 2H), 1.45-1.40 (m, 2H), 0.95 (t, 9H).

C150: (E)-1-(2-Dimethylaminomethyl-phenyl)-3-[2'-methyl-4-(4-pyrrolidin-1-yl-butoxy)-biphenyl-3-yl]-propenone General procedure H gave the title compound as an yellow/brown oil in 44% yield. $^1$H-NMR (CDCl$_3$) δ 7.63 (d, 1H), 7.50 (d, 1H), 7.39-7.19 (m, 9H), 7.11 (d, 1H), 6.93 (d, 1H), 4.05 (t, 2H), 3.54 (s, 2H), 2.49-2.47 (m, 6H), 2.27 (s, 3H), 2.13 (s, 6H), 1.86-1.75 (m, 6H), 1.65-1.60 (m, 2H).

C151: (E)-1-(2-Dimethylaminomethyl-phenyl)-3-[2'-methyl-4-(4-methylamino-butoxy)-biphenyl-3-yl]-propenone General procedure H gave the title compound as an yellow oil in 26% yield. $^1$H-NMR (DMSO-d$_6$) δ 7.72 (d, 1H), 7.70 (d, 1H), 7.69-7.21 (m, 10H), 7.11 (d, 1H), 6.67 (bs, 1H), 4.07 (m, 2H), 2H), 3.49 (s, 2H), 2.46 (t, 2H), 2.26 (s, 3H), 2.02 (s, 6H), 1.75 (s, 3H), 1.72-1.67 (m, 2H), 1.51-1.44 (m, 2H).

C152: (E)-3-[4-(2-Dimethylamino-ethoxy)-2'-methyl-biphenyl-3-yl]-1-(4-dimethylaminomethyl-phenyl)-propenone General procedure H gave the title compound as orange oil in 29% yield. $^1$H-NMR (CDCl$_3$) δ 8.25 (d, 1H), 8.14 (d, 2H), 7.85 (d, 1H), 7.72 (d, 1H), 7.59 (d, 2H), 7.47-7.37 (m, 5H), 7.13 (d, 1H), 4.42 (t, 2H), 3.69 (s, 2H), 3.13 (t, 2H), 2.62 (s, 6H), 2.43 (s, 6H), 2.41 (s, 3H).

C153: (E)-3-[4-(2-Dimethylamino-ethoxy)-2'-methyl-biphenyl-3-yl]-1-(3-dimethylaminomethyl-phenyl)-propenone General procedure H gave the title compound as yellow oil in 64% yield. $^1$H-NMR (CDCl$_3$) δ 8.16 (d, 1H), 7.97 (m, 2H), 7.73-7.62 (m, 3H), 7.49, (t, 1H), 7.34 (dd, 1H), 7.30-7.22 (m, 4H), 7.01 (d, H), 4.36 (t, 2H), 3.66 (bs, 2H), 3.09 (bs, 2H), 2.57 (bs, 6H), 2.37 (bs, 6H), 2.29 (s, 3H).

C154: (E)-3-[4-(2-Dimethylamino-ethoxy)-3',5'-dimethyl-biphenyl-3-yl]-1-[4-hydroxy-2-(4-methyl-piperazin-1-yl)-phenyl]-propenone General procedure H gave the title compound as yellow oil in 26% yield. $^1$H-NMR (CDCl$_3$) δ 8.11 (d, 1H), 7.89 (d, 1H), 7.69 (d, 1H), 7.56 (d, 1H), 7.54 (dd, 1H), 7.19 (bs, 2H), 6.99-6.96 (m, 2H), 6.50-6.46 (m, 2H), 4.21 (t, 2H), 3.05 (t, 4H), 2.89 (t, 2H), 2.54 (bs, 4H), 2.40 (s, 6H), 2.36 (s, 6H), 2.18 (s, 3H).

C155: (E)-3-(3,5-Di-tert-butyl-2-methoxy-phenyl)-1-[4-(2-dimethylamino-ethoxy)-2-(4-methyl-piperazin-1-yl)-phenyl]-propenone General procedure H gave the title compound as yellow crystals in 70% yield. $^1$H-NMR (CDCl$_3$) δ 8.01 (d, 1H), 7.62-7.54 (m, 3H), 7.38 (d, 1H), 6.62-6.58 (m, 2H), 4.12 (t, 2H), 3.77 (s, 3H), 3.07 (t, 4H), 2.76 (t, 2H), 2.50 (bs, 4H), 2.35 (s, 6H), 2.34 (s, 3H), 1.40 (s, 9H), 1.34 (s, 9H).

C156: (E)-3-[4-(2-Dimethylamino-ethoxy)-3',5'-dimethyl-biphenyl-3-yl]-1-(2-fluoro-4-hydroxy-phenyl)-propenone General procedure H gave the fumarate of the title compound as yellow crystals in 59% yield. $^1$H-NMR (DMSO-d$_6$) δ 7.95 (d, 1H), 7.91 (d, 1H), 7.74 (t, 1H), 7.69-7.60 (m, 2H), 7.26 (bs, 2H), 7.18 (d, 1H), 6.96 (bs, 1H), 6.75 (dd, 1H), 6.67 (dd, 1H), 6.47 (s,2H), 4.31 (t, 2H), 3.13 (t, 2H), 2.53 (s, 6H), 2.30 (s, 6H).

C157: (E)-3-[4-(2-Dimethylamino-ethoxy)-3',5'-dimethyl-biphenyl-3-yl]-1-[4-(2-dimethylamino-ethoxy)-2-fluoro-phenyl]-propenone General procedure H gave the title compound as yellow crystals in 36% yield. $^1$H-NMR (DMSO-d$_6$) δ 8.00 (d, 1H), 7.91 (d, 1H), 7.81 (t, 1H), 7.76 (d, 1H), 7.71-7.67 (m, 1H), 7.31 (bs, 2H), 7.20 (d, 1H), 7.01-6.91 (m, 3H), 4.20 (t, 2H), 4.17 (t, 2H), 2.71 (t, 2H), 2.64 (t, 2H), 2.33 (s, 6H), 2.22 (s, 6H), 2.21 (s, 6H).

C158: (E)-3-(2,4-Dichloro-phenyl)-1-[4-(2-dimethylamino-ethoxy)-2-fluoro-phenyl]-propenone General procedure H gave the fumarate of the title compound as yellow crystals in 37% yield. $^1$H-NMR (DMSO-d$_6$) δ 8.05 (d, 1H), 7.91-7.83 (m, 2H), 7.75 (d, 1H), 7.60 (dd, 1H), 7.52 (dd, 1H), 7.03-6.93 (m, 2H), 6.58 (s, 2H), 4.25 (t, 2H), 2.86 (t, 2H), 2.37 (s, 6H).

C159: (E)-3-(2,4-Dichloro-phenyl)-1-[3-(2-dimethylamino-ethoxy)-phenyl]-propenone, General procedure H gave the fumarate of the title compound as white crystals in 8% yield. $^1$H-NMR (DMSO-d$_6$) δ 8.04 (d, 1H), 7.62 (d, 1H), 7.54-7.49 (m, 2H), 7.39 (d, 1H), 7.38 (d, 1H), 7.33 (d, 1H), 7.24 (ddd, 1H), 7.19 (s, 2H), 7.10 (ddd, 1H), 4.11 (t, 2H), 2.75 (t, 2H), 2.33 (s, 6H).

C160: (E)-3-[5-tert-Butyl-2-(2-dimethylamino-ethoxy)-phenyl]-1-(4-hydroxy-phenyl)-propenone General procedure H gave the fumarate of the title compound as yellow crystals in 42% yield. $^1$H-NMR (DMSO-d$_6$) δ 8.05 (d, 2H), 7.95 (, 2H), 7.82 (d, 1H), 7.42 (d, 1H), 7.05 (d, 1H), 6.91 (d, 2H), 6.58 (s, 3H), 4.24 (t, 2H), 3.00 (t, 2H), 2.46 (s, 6H), 1.32 (s, 9H).

C161: (E)-3-[4-(2-Dimethylamino-ethoxy)-biphenyl-3-yl]-1-(4-hydroxy-phenyl)-propenone General procedure H gave the title compound as yellow crystals in 25% yield. $^1$H-NMR (CDCl$_3$) δ 7.99 (d, 1H), 7.93 (d, 1H), 7.76 (d, 1H), 7.73 (s, 1H), 7.52-7.47 (m, 3H), 7.36 (t 2H), 7.28-7.23 (m, 1H), 6.95 (d, 1H), 6.84 (dd, 2H), 4.14 (t, 2H), 2.79 (t, 2H), 2.31 (s. 6H).

C162: (E)-1-(2-Dimethylaminomethyl-phenyl)-3-[2'-methyl-4-(5-pyrrolidin-1-yl-pentyloxy)-biphenyl-3-yl]-propenone General procedure H gave the title product as yellow crystals in 43% yield. $^1$H-NMR (CDCl$_3$) δ 7.57 (d, 1H), 7.43 (d, 1H), 7.36-7,13 (m, 9H), 7.05 (d, 1H), 6.86 (d, 1H), 3.97 (t, 2H), 3.48 (s, 2H), 2.72 (bs, 2H), 2.57 (bs, 2H), 2.21 (s, 3H), 2.07 (s, 6H), 1.95 (s, 4H), 1.85 (bs, 4H), 1.79-1.71 (m, 2H), 1.62 (bs, 2H), 1.43-1.37 (m, 2H),

C163: (E)-3-[2-(2-Dimethylamino-ethoxy)-5-pyridin-3-yl-phenyl]-1-(2-dimethylaminomethyl-phenyl)-propenone General procedure H gave the title product as yellow oil in 25% yield. $^1$H-NMR (DMSO-d$_6$) δ 8.74 (d, 1H), 8.51 (dd, 1H), 7.77 (dt, 1H), 7.69 (d, 1H), 7.56 (d, 1H), 7.48 (dd, 1H), 7.36-7.26 (m, 5H), 7.13 (d, 1H), 6.94 (d, 1H), 4.09 (t, 2H), 3.53 (s, 2H), 2.67 (t, 2H), 2.20 (s, 6H), 2.10 (s, 6H).

C164: (E)-3-[2-(2-Dimethylamino-ethoxy)-5-pyridin-2-yl-phenyl]-1-(2-dimethylaminomethyl-phenyl)-propenone General procedure H gave the title product as yellow oil in 48% yield. $^1$H-NMR (CDCl$_3$) δ 8.61-8.58 (m, 1H), 8.16 (d, 1H), 7.92 (dd, 1H), 7.68-7.56 (m, 3H), 7.43-7.12 (m, 6.93 (d, 1H), 4.11 (t, 2H), 3.57 (s, 2H), 2.69 (t, 2H), 2.22 (s, 6H), 2.14 (s, 6H).

C165: (E)-3-[4-(2-Dimethylamino-ethoxy)-3'-methyl-biphenyl-3-yl]-1-(2-dimethylaminomethyl-phenyl)-propenone General procedure H gave the title product as yellow crystals in 12% yield. $^1$H-NMR (DMSO-d$_6$) δ 11.40 (bs, 1H), 9.93 (bs, 1H), 8.24 (d, 1H), 8.15 (dd, 1H), 8.03 (d, 1H), 7.99-7.67 (m, 5H), 7.54 (d, 2H), 7.34 (d, 1H), 7.28 (d, 1H), 4.58 (t, 2H), 4.43 (d, 2H), 3.59-3.55 (m, 2H), 2.82 (d, 6H), 2.78 (d, 6H), 2.39 (s, 3H).

C166: (E)-3-[3-(2-Dimethylamino-ethoxy)-2'-methyl-biphenyl-4-yl]-1-(2-dimethylaminomethyl-phenyl)-propenone General Procedure H gave the title product at yellow oil in 32% yield. $^1$H-NMR (DMSO-d$_6$) δ 7.81 (d, 1H), 7.57 (d, 1H), 7.47-7.40 (m, 2H), 7.40-7.34 (m, 2H), 7.33-7.20 (m, 5H), 7.01 (d, 1H), 6.96 (dd, 1H), 4.12 (t, 2H), 3.50 (s, 2H), 2.55 (t, 2H), 2.27 (s, 3H), 2.09 (s, 6H), 2.04 (s, 6H).

C167: (E)-3-[2'-Bromo-4-(2,-dimethylamino-ethoxy)-biphenyl-3-yl]-1-(2-dimethylaminomethyl-phenyl)-propenone General procedure H gave the title product as brown oil in 8% yield. $^1$H NMR (300 MHz, CDCl$_3$): δ 7.62-7.57 (m, 4H), 7.44-7.06 (m, 8H), 6.89 (d, 1H), 4.12 (bs, 2H), 3.60 (s, 2H), 2.72 (bs, 2H), 2.36 (s, 6H), 2.17 (s, 6H).

C168: (E)-3-[4-(2-Dimethylamino-ethoxy)-4'-methyl-biphenyl-3-yl]-1-(2-dimethylaminomethyl-phenyl)-propenone General procedure H gave the hydrochloride of the title product as yellow crystals in 57% yield. $^1$H-NMR (300 MHz, DMSO-d$_6$) δ 11.93 (br, 1H), 10.31 (br, 1H), 8.00 (d, 1H), 8.00-7.95 (m, 1H), 7.89 (d, 1H), 7.87-7.83 (m, 1H), 7.63-7.56 (m, 3H); 7.50 (d, 1H), 7.42 (d, 2H), 7.18 (s, 2H), 7.08 (d, 1H), 4.57 (t, 2H), 4.44 (d, 2H), 3.59 (dt, 2H1), 2.88 (d, 6H), 2.83 (d, 6H), 2.31 (s, 3H).

C169: (E)-3-[5-(2-Dimethylamino-ethoxy)-biphenyl-3-yl]-1-(2-dimethylaminomethyl-phenyl)-propenone General procedure H gave the title compounds as a yellow oil in 60% yield. $^1$H-NMR (DMSO-d$_6$): δ 7.74 (bd, 2H), 7.60 (bs, 1H), 7.48-7.30 (m, 10H), 7.24 (t, 1H), 4.17 (t, 2H), 3.53 (s, 2H), 2.64 (t, 2H), 2.23 (s, 6H), 2.03 (s, 6H).

Determination of Metabolic Stability

Incubations were performed with Wistar rat liver microsomes (0.25 mg/ml) in 2% sodium bicarbonate solution. NADP (0.13 mg/ml), glucose-6-phosphate (0.63 mg/ml) and glucose-6-phosphate dehydrogenase (0.38 units/ml) were used as NADPH generation system and UDPGA (0.48 mg/ml) was added to include the phase II reaction, glucuronic acid conjugation, in the assay. After 5 minutes of pre-incubation the reaction was started by addition of the test article to give a final concentration of 20 μM. Samples were incubated for 15 min at 37° C. and the reactions were terminated by addition of equal volumes of acetonitrile. Blank incubations were performed at the same concentration but without addition of microsomes. Both blank and microsome-containing samples were made in replicats of three. Prior to analysis samples were centrifuged for 10 min. at 3500 rpm,HPLC system:

The fraction of compound metabolised during the 15 min of incubation was determined by comparison of blank and microsome-containing samples using a Waters Alliance 2690 separation module and Waters 996 PDA-detector(Waters. Milford, Mass., USA.) Separation was performed on a XTerra MS C$_{18}$ column (150*2.1 mm I.D., 3,5 μm particle size) (Waters Milford, Mass., USA) by. Initial conditions were 40% mobile phase A (acetonitrile) and 60% mobile phase B (10 mM ammonium acetate pH 9.5). During the first 20 minutes, the mobile phase was changed via a linear gradient to 90% A and 10% B. This was followed by a 5 minutes linear gradient to initial conditions, which were maintained for 5 min. The flow rate was 0.20 m)/min and injection volume 10 μl.

Determination of Solubility

Solubility of the compounds was determined by preparing a saturated solution of compound in 0.3 M phosphate buffer (pH 7.4±0.3) in a brown glass tube. The suspensions were rotated slowly for 24 hours. Aliquots were centrifuged for 10 minutes at 14.000 rpm and supernatants were diluted in 40% (v/v) acetonitrile in water prior to HPLC analysis. Concentrations of analytes were quantified against a standard curve and used as term of solubility. The HPLC-UV method used for the assessment of solubility is the same as used in the in vitro metabolism assay.

Pharmacokinetic Studies

Evaluation of the pharmacokinetic properties of the compounds was done using female NMRI mice (weighing app. 30 g). Test articles were administrated intravenously and orally as a cassette dose formulations containing three compounds or as individual compounds. Samples of serum were taken at defined timepoints.

Standards and QC-samples in plasma were prepared and the serum concentrations of the test compounds quantified by HPLC-MS.

Prior to analysis, proteins were precipitated by deluding the samples (1:1) (v/v) with 100% acetonitrile followed by centrifugation at 14.000 rpm in 10 min. The supernatant was used for the analysis.

HPLC-MS System:

A Waters Alliance HPLC-system (Milford, Mass., USA) was coupled to a Quatro Micro triple quadropl mass spectrometer (Micromass, Manchester, UK) operating in positive (ESI) mode. Separation was performed on a XTerra MS C$_{18}$ column (150*2.1 mm I.D., 3,5 μm particle size) (Waters Milford, Mass., USA).

Mobile phase A: 0.1% (v/v) formic acid or 10 mM ammonium acetate pH-adjusted to 9.5 in MilliQ-water, mobile phase B: 100% methanol. The gradient was as follows: 0-min=70% A-30% B, 0-10 min. a linear gradient to 10% A and 90% B this was maintained till 11 min, 11-13 linear gradient to 70% A and 30% B this was maintained till 18 min. The flow rate was 0.20 m/min, injection volume 10 μl.

Biological Testing

General Methods

In vitro Microbiological Testing

MIC Determination in Broth Microdilution Assay

Compounds were screened for activity against a panel of 10 different non-fastidious bacteria growing aerobically (*Staphylococcus aureus* ATCC29213; *Staphylococcus aureus* ATCC33591;*Staphylococcus* intermedius #2357(clinical isolate from the Copenhagen area); *Enterococcus faecalis* ATCC29212;*Enterococcus faecium* #17501 (vancomycin-resistant clinical isolate); *Streptococcus pneumoniae* #998 (clinical isolate); *Streptococcus pyogenes* #14813 (clinical isolate); *Streptococcus agalactiae* #19855 (clinical isolate); *Eschericia coli* ATCC25922 and *Eschericia coli* ESS). The screening assay was done in 200 µl MH-broth cultures in microtitre plates. For compounds exhibiting activity in the initial screen MIC was determined in a microdilution assay using MH-broth as described by NCLLS (National Committee for Clinical Laboratory Standards. Methods for Dilution Antimicrobial Susceptibility Tests for Bacteria That Grow Aerobically; Approved Standard—Fifth Edition. M7-A5 NCCLS 2000) modified to include uninoculated dilution series of test compounds to facilitate MIC determination if the test compound should precipitate. MIC was determined as the lowest concentration of test compound able to inhibit visible growths of bacteria. MICs for ATCC type strains fell within the limits posted by the NCCLS (National Committee for Clinical Laboratory Standards. Performance Standards for Antimicrobial Susceptibility Testing; Eleventh Informational Supplement. M100-S11 NCCLS 2001) when tested against vancomycin, tetracycline, gentamycin.

MIC and MBC Determination in Broth Macrodilution Assay

MIC and MBC of test compounds were determined in a broth macrodilution assay using 2 ml MH-broth cultures and an inoculum of approximately 5×10E5 CFU/ml as described by Amsterdam (Amsterdam, D. Susceptibility testing of antimicrobials in liquid media. In V. Lorian (ed.): Antibiotics in Laboratory Medicin 4. edition. Williams & Wilkins 1996). MIC was determined as the minimal concentration of test compound able to inhibit visible growth of bacteria. Samples from cultures inhibited by test compound were plated onto unselective blood agar plates. MBC was determined as the minimal concentration of test compound able to decrease colony count on these plates below 0.1% compared to the original inoculum.

Killing Curve Determination

Figure 2:
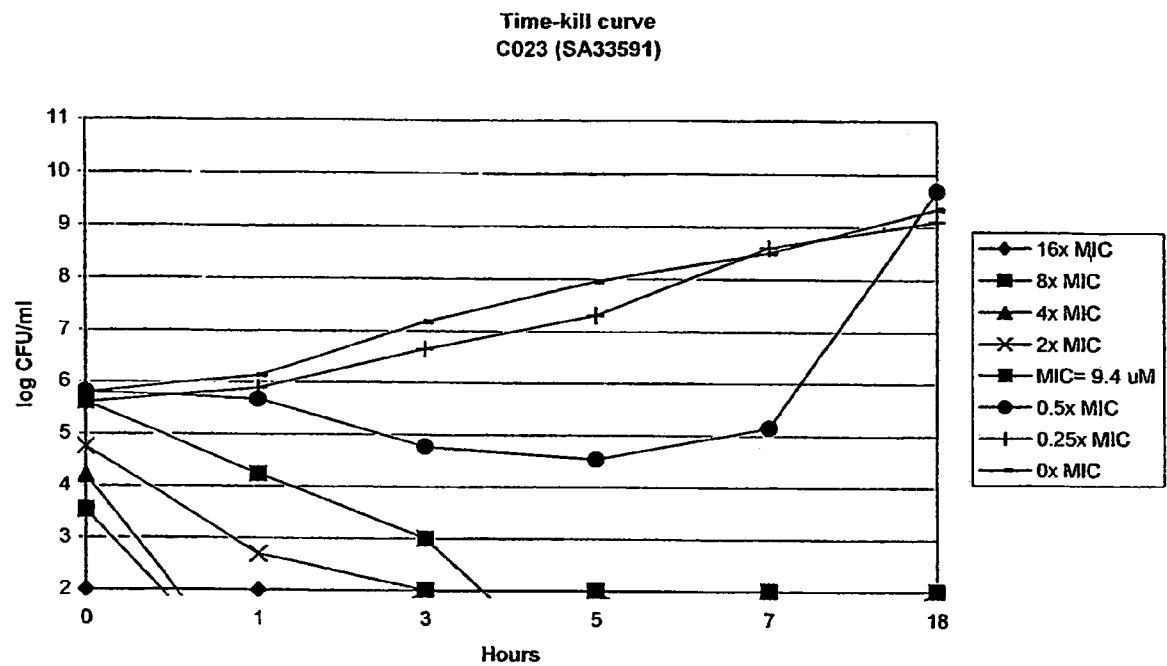
FIG. 2 illustrates a time-kill curve of C023 against *S. aureus* ATCC33591. Bacterial growth is inhibited at concentrations at or above the MIC (MIC=9.4 µM). As CFU counts per ml decreases at concentrations of compound above the MIC, the compound is bactericidal. The reduction in CFU/ml is faster as the concentration of test compound increases above the MIC. This indicates that the bactericidal action of the compound is primarily dependent on the concentration of the test compound.
Figure 3:
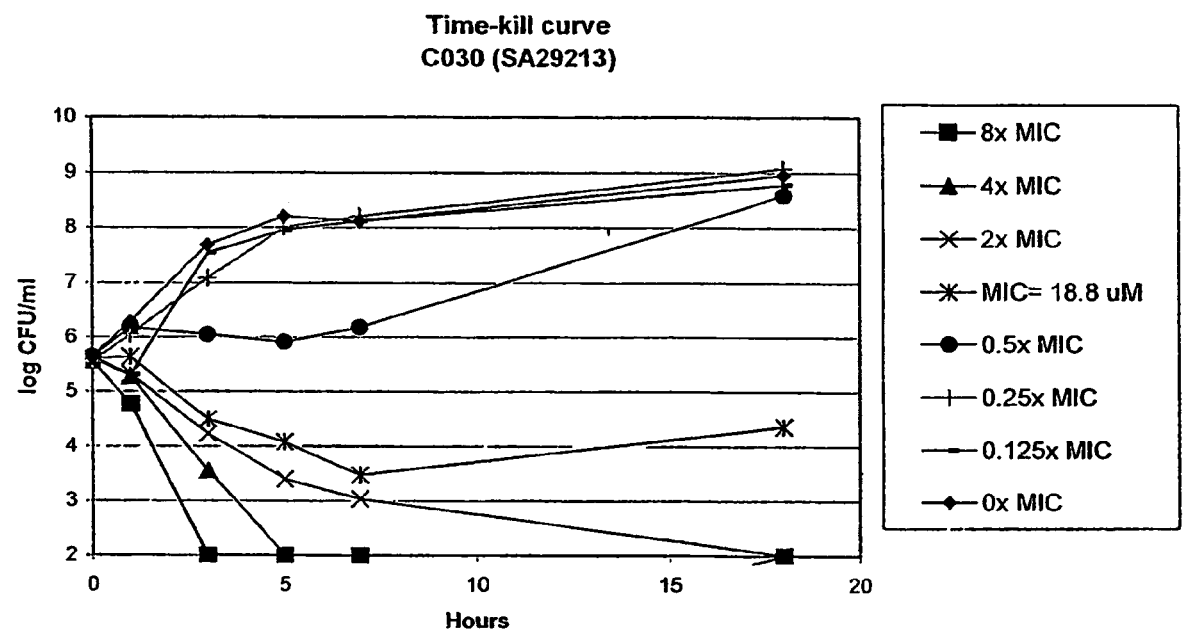
FIG. 3 illustrates a time-kill curve of C030 against *S. aureus* ATCC29213. Bacterial growth is inhibited at concentrations at or above the MIC (MIC=18.8 µM). As CFU counts per ml decreases at concentrations of compound above the MIC, the compound is bactericidal. The reduction in CFU/ml is faster as the concentration of test compound increases above the MIC. This indicates that the bactericidal action of the compound is primarily dependent on the concentration of the test compound.

For the determination of the killing curve of a test compound a dilution series of test compound was made and inoculated with approximately 5×10E5 CFU/ml as described for the MIC macrodilution assay above. At the timepoints indicated 100 µl samples was withdrawn from the test tubes, serially diluted and spotted in duplicate on unselective agar plates to determine CFU. Test compounds with bactericidal activity is capable of decreasing surviving colony counts (CFU/ml) when incubated with bacteria. Bactericidal activity may be either primarily dependent on concentration of test compound or on incubation time with test compound. An example of a bactericidal compound (C023), which is primarily dependent on the concentration of the test compound is shown in FIG. 2. An example of a bactericidal compound (C030) which is primarily dependent on the incubation time with the compound is shown in FIG. 3.

MIC Determination Against *Helicobacter pylori*

Six strains of *Helicobacter pylori* were used in an agar dilution assay according to the standards of NCCLS (National Committee for Clinical Laboratory Standards. Methods for Dilution Antimicrobial Susceptibility Tests for Bacteria That Grow Aerobically; Approved Standard—Fifth Edition. M7-A5 NCCLS 2000). MH-agar plates supplemented with 5% horse blood and containing a dilution series of the test compound were inoculated in duplicate with 10 µl spots of a 2 McF suspension of the different strains of *H.pylori*. This inoculum corresponds to approximately 10E6 CFU/spot. Plates were then incubated in a microaerophilic atmosphere at 35° C. for 72 hours. The MIC endpoint was determined as the lowest concentration of test compound able to completely inhibit or most significantly reduce growth compared to growth control plates not containing test compounds.

Activity Determination Against Anaerobic Bacteria

Screening for activity against anaerobic bacteria was done against two isolates of *Bacteroides fragilis*, an isolate of *Clostridium difficile* and an isolate of *Clostridium perfringens* in an agar dilution assay as described by NCCLS (National Committee for Clinical Laboratory Standards. Methods for Antimicrobial Susceptibility Testing of Anaerobic Bacteria; Approved Standard—Fifth Edition. M11-A5 NCCLS 2000) with the exception that Mueller-Hinton agar was used in place of supplemented Brucella broth. Plates containing test compound at a single concentration (either 100 or 150 µM) were prepared in duplicate along with appropriate control plates. Activity was present if growth in the presence of test substance was absent or most significantly reduced compared to growth control plates not containg test compound.

*Leishmania* Promastigote Assay

A WHO reference vaccine strain of *L.major* originally isolated from a patient in Iran were cultured in Medium 199 with Hanks' Salts containing 0.02 mg/ml gentamycin, 25 mM HEPES, 4 mM L-glutamine, and 10% heat inactivated fetal calf serum (FCS). Incubation was carried out at 27° C. Promastigotes were harvested at day 3 of culture and used for the assay of inhibition of parasite growth.

The effect of test compounds on promastigotes was assessed by a method modified from Pearson et al. Briefly, promastigotes (0.8×$10^6$/well) were incubated in 200 µl duplicate cultures either with a dilution series of test compound or medium alone In 96 wells flat buttom microtiter plates. After 2 h of incubation, 1.5 µCi of 3H-thymidine was added to each well and further incubated for 18 hours. The cultures were then harvested on Unifilter-GF/C microtiter filter plates (Packard Instruments), washed extensively and counted in a TopCount-NXT microplate scintillation counter (Packard Instruments).

*Plasmodium falciparum* Assay

*Plasmodium falciparum* 3D7 was maintained in culture by a modification of the method originally described by Trager and Jensen. In brief, the parasites were grown in suspensions of human blood group 0 erythrocytes (RBC) maintained in RPM11640 medium supplemented with 4.5 g/l Albumax II (Invitrogen), 10 mM hypoxantine, 1.4 mM L-glutamine and 0.05 mg/ml gentamicin. Cultures were incubated at 37° C. in atmosphere of 92.5% nitrogen, 5.5% carbon dioxide, and 2% oxygen. To obtain synchronized cultures og parasites erythrocytes infected with late trophozoite and schizont stages were separated from ring stages and uninfected RBC by magnet-activated cell sorting (MACS; Miltenyi BioTec) (Staalsoe, T., H. A. Giha, D. Dodoo, T. G. Theander, and L. Hviid.

1999. Detection of antibodies to variant antigens on *Plasmodium falciparum*-infected erythrocytes by flow cytometry. Cytometry 35:329-336). Because of their high content of paramagnetic haemozoin, erythrocytes infected with late developmental stages of malaria parasites are specifically retained within the column. The column was washed with PBS supplemented with 2% foetal calf serum and then the column was removed from the magnet and the retained late developmental stages of parasites were eluted and cultured for an additional 18 hours. At this time the culture is highly synchronous containing more than 90% ring stages.

These synchronized cultures of ring stage parasites were used to assay for antimalarial parasites. Briefly, cultures of ring stage parasites were adjusted to 1% parasitemia by addition of uninfected RBC. Then, these were incubated in 12 µl duplicate cultures containing $2.5 \times 10^7$ RBC/well with either a dilution series of test compound or with medium alone. Plates were then incubated at 37° C. for 24 hours when cultures were labelled by the addition 1.1 µCi 3H-phenylalanine and incubated overnight. Then, the cultures were harvested on Unifilter-GF/C microfilter plates (Packard Instruments) and washed extensively with water followed by a wash with 10% $H_2O_2$ to bleach hemoglobin. Filter plates were counted in a TopCount-NXT microplate scintillation counter (Packard Instruments).

DHODH Assay

100 µl chalcone or 0.1 M Tris-HCl pH 8.0 is added to a well in a 96-wells microtiter plate. Then 50 µl enzyme dilution is added. The microtiter plate is placed in the Powerwave$_x$340 and the enzymatic reactions starts when adding 100 µl assay mixture. The reaction are measured every 20 sec. for 10 min. The samples with chalcones are compared with the samples with 0.1 M Tris-HCl pH 8.0 and the percent inhibition is calculated.

Enzyme dilution: The solution of recombinant purified enzyme is dissolved in 0.1 M Tris-HCl pH 8 to give an initial velocity of 0.04-0.05 ΔA/min.

2,6-dichlorophenolindophenol (DCIP)-stock solution: 40 mg DCIP and 10 ml 99% Ethanol are mixed for 10 min at RT. Then 100 µl 1.0 M Tris-HCl pH 8 and miliQ H2O are added to a final volume of 100 ml. The $A_{600}$ of the DCIP-stock solution are measured in a microtiter plate on the Powerwave$_x$340 (Bio-Tek instruments,Inc.)

Dihydroorotate dehydrogenase (DHODH)-stock solution: 25 mM dihydroorotate stock-solution is prepared by first dissolving in the same amount of mol NaOH and then miliQ $H_2O$ is added to the final volume.

Assay mix (10 ml solution): 600 µl of DHODH-stock solution and X ml (depending on the $A_{600}$ value of stock-solution) DCIP to a final $A_{600}$=2.5 are mixed. Then 0.1 M Tris-HCl pH 8.0 are added to a final volume of 10 ml.

Preparation of compound soluton: A 10 mM stock-solution of compound (e.g. a chalcone derivative) is made in dimethylsulfoxid (DMSO). The compound is then diluted in 0.1 M Tris-HCl pH 8 to the test concentrations. The final DMSO concentration in the sample is 10%

Biological Results

Licochalcone A (LicA) and 4'-methoxy chalcone (4'MC) described in WO 93/17671 are used as reference compounds in the following discussion.

Activity Against Non-fastidious Bacteria

Licochalcone A exhibits moderate bactericidal activity against common pathogenic Gram-positive non-fastidious bacteria including *Staphylococcus aureus*, *Enterococcus faecalis*, *Enterococcus faecium*, *Streptococcus pneumoniae*, *Streptococcus pyogenes*, and *Streptococcus agalactiae*. Licochalcone A maintains its activity also against antibiotic resistant bacteria, e.g. *Staphylococcus aureus* ATCC33591 (resistant to methicillin) and *Enterococcus faecium* #17051 (resistant to vancomycin). In contrast, Licochalcone A has only modest or no activity against the prototype,pathogenic Gram-negative bacterium, *Eschericia coli*. 4'MC as a representative of non-hydroxyl chalcones exhibits no antibacterial effect at all.

In comparison with Licochalcone A, aminoalkoxy-functional chalcones retain the activity of Licochalcone A against pathogenic Gram-positive bacteria including antibiotic-resistant strains (cf. Table 1). The aminoalkoxy-functional chalcones exhibit increased potency against Gram-positive pathogens (e.g. C004, C015, C023, C030, C037, C042). In contrast to Licochalcone A, aminoalkoxy-functional chalcones exhibit activity against *Eschericia coli*. Thus, several aminoalkoxy-functional chalcones (e.g. C074, C075, C103) exhibit high activity against *E coli* ATCC25922 and against the generally more susceptible ESS strain of *E.coli* (cf. Table 1). This indicates the potential use of aminoalkoxy-functional chalcones in the treatment of infections associated with Gram-negative bacteria.

In the treatment of severe infections in immunocompromised patients bacteriocidal action of an antibiotic is a necessity. As exemplified in FIGS. 2 and 3, aminoalkoxy chalcones retain the bactericidal action of Licochalcone A. For aminoalkoxy chalcones the bactericidal action is predominantly dependent on the concentration of the compound (e.g. C023 and C030; cf. FIGS. 2 and 3). This knowledge is helpful when designing dosing regimens for in vivo efficacy trials.

TABEL 1

Comparison of the effect of aminoalkoxy-chalcones and Licochalcone/4'MC on bacteria; MIC values in µM.

|  | A | B | C | D | E | F | G | H |
|---|---|---|---|---|---|---|---|---|
| LICA | 37.5 | 37.5 | 37.5 | 37.5 | 37.5 | 75.0 |  | 300.0 |
| 4'-MC | NA | NA | NA | NA | NA | NA | NA | NA |
| C004 | 9.4 | 9.4 | 18.8 | 18.8 | 18.8 | 18.8 | 75.0 | 9.4 |
| C023 | 4.7 | 4.7 | 4.7 | 4.7 | 4.7 | 18.8 |  | 9.4 |
| C039 | 9.4 | 18.8 | 18.8 | 18.8 | 18.8 | 18.8 | 75.0 | 9.4 |
| C074 | 9.4 | 9.4 | 9.4 | 9.4 | 9.4 |  | 9.4 | 4.7 |
| C075 | 4.7 | 4.7 | 9.4 | 9.4 | 9.4 |  | 9.4 | 4.7 |
| C085 | 4.7 | 4.7 | 4.7 | 4.7 | 4.7 | 75 |  | 4.7 |
| C157 | 4.7 | 9.4 | 9.4 | 9.4 | 9.4 | 9.4 | 18.8 | 4.7 |
| C089 | 9.4 | 9.4 | 18.8 | 9.4 | 9.4 | 9.7 | 37.5 | 4.7 |
| C092 | 4.7 | 9.4 | 18.8 | 4.7 | 4.7 | 4.7 | 75 | 4.7 |
| C093 | 4.7 | 4.7 | 4.7 | 9.4 | 4.7 | 18.8 |  | 4.7 |
| C072 | 9.4 | 18.8 | 9.4 | 18.8 | 18.8 | 37.5 |  | 9.4 |
| C103 | 4.7 | 4.7 | 9.4 | 9.4 | 9.4 |  | 18.8 | 4.7 |
| C104 | 9.4 | 18.8 | 18.8 | 9.4 | 9.4 | 9.4 | 18.8 | 9.4 |
| C067 | 4.7 | 4.7 | 4.7 | 4.7 | 4.7 | 18.8 |  | 18.8 |

A: *Staphylococcus aureus* ATCC29213;
B: *Staphylococcus aureus* ATCC33591(resistant to methicillin);
C: *Staphylococcus intermedius* #2357(clinical isolate from the Copenhagen area);
D: *Enterococcus faecalis* ATCC29212;
E: *Enterococcus faecium* #17501 (vancomycin-resistant clinical isolate);
F: *Streptococcus pneumoniae* #998 (clinical isolate);
G: *Eschericia coli* ATCC25922 and
H: *Eschericia coli* ESS.
NA: no activity.

Activity Against *Helicobacter pylori*

Colonisation of the gastric mucosa with *Helicobacter pylori* is an important pathogenic determinant for the development of gastritis and peptic ulcer. Aminoalkoxychalcones exhibit activity against *Helicobacter pylori*. Several aminoalkoxychalcones (e.g.C004, C010, C014, C022, C030, C088, C094) exhibit MICs in the range between 12 μM and 25 μM when tested against a panel of six strains *Helicobacter pylori*, that includes strains resistant to metronidazole. Metronidazol is an antibiotic commonly included in treatment regimens designed to eradicate *Helicobacter* colonization for the treatment of peptic ulcer. The activity of aminoalkoxychalcones against both metronidazole-resistant and sensitive *Helicobacter pylori* clearly indicates the potential use of these compounds in the treatment of *Helicobacter* infections.

Activity Against Anaerobic Bacteria

Aminoalkoxychalcones have been assayed in a single concentration of compound (100 μM) for activity against a panel of anaerobic bacteria containing common human pathogenic bacteria (*Bacteroides fragilis, Clostridium perfringens, Clostridium difficele*). Several aminoalkoxychalcones (e.g. C015, C025, C026, C028 and C042, C074, C079) exhibit activity against all microorganisms within the test panel. This clearly indicates the potential use of aminoalkoxychalcones in treatment of infection caused by anaerobic bacteria.

Activity Against Protozoa

Activity Against *Plasmodium falciparum*

Figure 4:
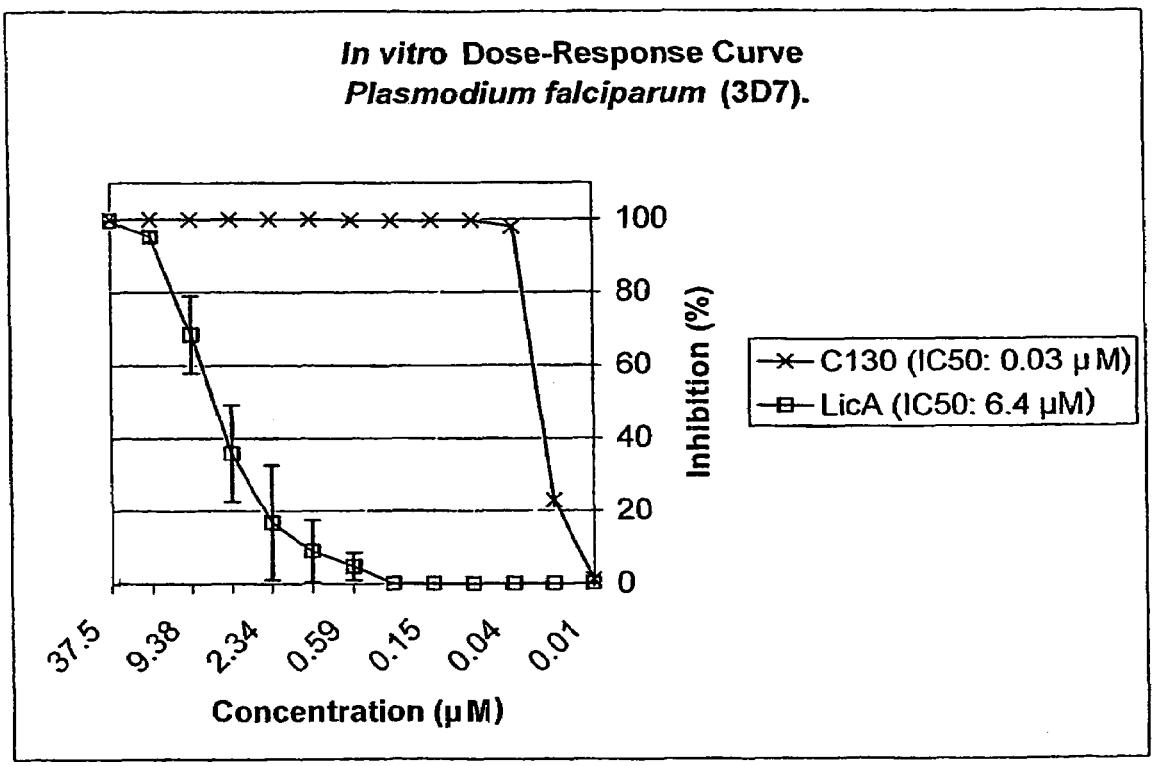
FIG. 4 illustrates a dose-response curve of LicA and one of the novel aminoalkoxy-chalcones (C130) at *Plasmodium falciparum*. As shown in the figure, C130 is 213 times more potent than LicA.
Figure 5:
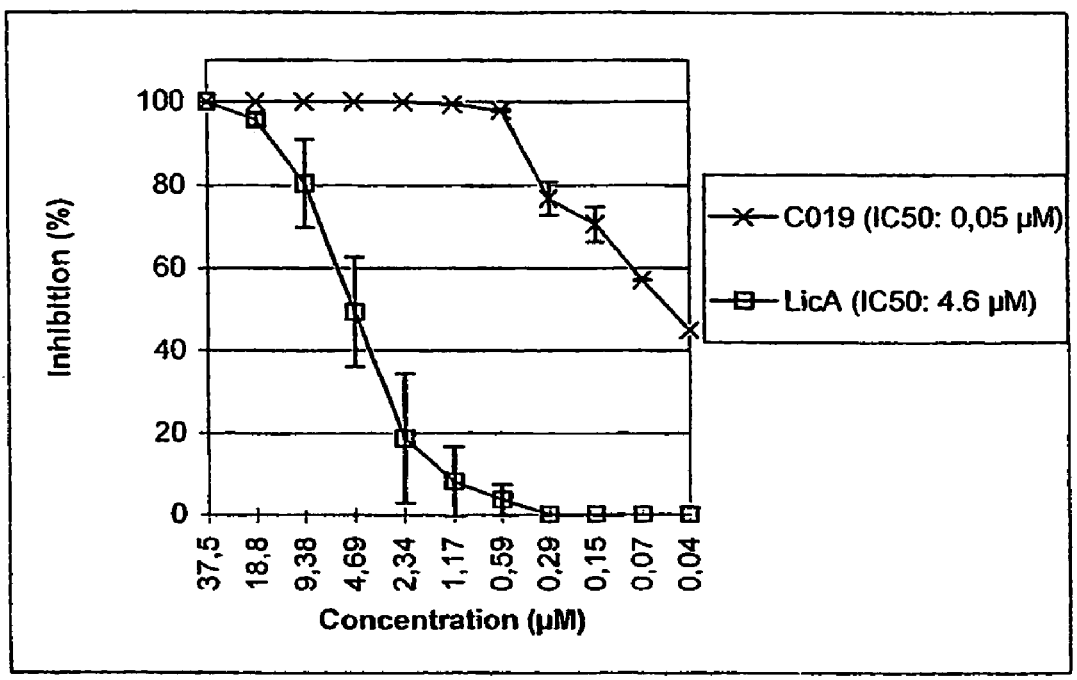
FIG. 5 illustrates a dose-respons curve of LicA and one of the novel chalcones (C019) at *Leishmania Major*. As shown at the figure, C019 is 100 times more potent than LicA.

*Plasmodium falciparum* is a protozoan parasite transmitted by the mosquito *Anopheles*, and causing malignant or severe malaria in humans. Licochalcone A exhibits activity against *Plasmodium falciparum* in vitro and protects mice from infection with *P.yoelii* and *P.berghei* (Chen et al., 1994). Aminoalkoxychalcones exhibit activity in vitro against *Plasmodium falciparum* and several aminochalcones exhibit improved potency compared to Licochalcone A (cf. Table 2 and FIG. 4). Furthermore, the compounds are potent against chloroquine resistant parasites as shown in Table 3. The results clearly indicate the potential use of aminoalkoxychalcones in the treatment of malaria.

Activity Against *Leishmania major*

*Leishmania major* is a protozoan parasite transmitted by the sandfly *Phlebotomus*, and causing cutaneous leishmaniasis or kala-azar in humans. Licochalcone A exhibits activity against *Leishmania* parasites and has shown efficacy in experimental animal models of cutaneous and visceral *Leishmania* infection (Chen et al., 1994). Aminoalkoxychalcones exhibit activity in vitro against *Leishmania major* with significantly improved potency compared to Licochalcone A and 4'MC (cf. Table 4). The results clearly indicate the potential use of aminoalkoxychalcones in the treatment of *Leishmania* infection.

TABLE 4

Effect of aminoalkoxy-chalcones on L. major.

| Comp. | LicA | 4'MC | C004 | C011 | C015 | C020 | C024 | C032 | C037 | C042 | C140 |
|---|---|---|---|---|---|---|---|---|---|---|---|
| $IC_{50}$ (μM) | 4.6 | 5.6 | 0.2 | 0.1 | 0.1 | 0.03 | 0.04 | 0.7 | 0.5 | 0.2 | 0.2 |

Inhibition of DHODH

Several of the aminoalkoxy-chalcones prepared are potent inhibitors of DHODH. The compounds are as potent as LicA and by far more potent than ordinary chalcones exemplified by 4'MC.

TABLE 5

Inhibition of DHODH at 10 μM.

| Comp. | LicA | 4'MC | C019 | C020 | C022 | C026 | C027 | C028 |
|---|---|---|---|---|---|---|---|---|
| Inhibition | 25% | 7% | 18% | 18% | 21% | 19% | 22% | 23% |

Metabolism

The usefulness of chalcones as drug candidates have been limited by the metabolism of the compounds resulting in short half-lives in vivo (Lica: 100% turn-over in vitro and $t_{1/2}$=10 min in vivo).

The introduction of a aminoalkoxy group in the chalcone changes the metabolic properties; this is clear from Table 6 where the metabolic turn-over of a number of aminoalkoxy-chalcones are compared to LicA. The aminoalkoxy-chalcones prepared are expected to show low or no metabolism in vivo as the metabolic turn-over are between 0-10% (compared to 100% turn-over for Lica). Consequently the half-life of a aminoalkoxy-chalcone will be longer, reducing the dose needed for treatment.

TABLE 2

Activity against *Plasmodium falciparum* 3D7.

| Comp. | LicA | 4'MC | C032 | C035 | C036 | C038 | C160 | C075 | C156 | C090 | C130 | C131 |
|---|---|---|---|---|---|---|---|---|---|---|---|---|
| $IC_{50}$ (μM) | 6.4 | 40.0 | 0.5 | 0.1 | 0.2 | 0.2 | 0.3 | 0.5 | 0.1 | 0.5 | 0.03 | 0.3 |

TABLE 3

Activity against resistant strains of *Plasmodium falciparum*.

| | *Plasmodium falciparum* $IC_{50}$ (μM) | | | |
|---|---|---|---|---|
| | 3D7(Cq-sen) | DD2(Cq-res) | 7G8(Cq-res) | K1(Cq-res) |
| C130 | 0.03 | 0.06 | 0.05 | 0.04 |
| Chloroquine | 0.13 | 1.0 | 1.09 | >1.56 |

TABLE 6

| | Metabolic turn-over (rat) in vitro (%). | | | | | | |
|---|---|---|---|---|---|---|---|
| Comp. | LicA | C130 | C024 | C074 | C075 | C089 | C092 | C071 |
| Turn-over | 100% | 6% | 3% | 7% | 8% | 9% | 4% | 3% |

Solubility

The aqueous solubility of the neutral chalcones described in WO 93/17671 is very low. A representative chalcone 4'-methoxy-chalcone has a solubility of <<0.05 mg/ml. A few chalcones have a higher solubility due to (metabolically unstable) hydroxyl groups in the molecule. LicA has a solubility of approximately 0.01 mg/ml.

The aminoalkoxy-chalcones described in this application are superior having solubility numbers in sub-mg/ml. Representative examples are shown in table 7.

TABLE 7

| | Solubility in aqueous buffer at pH 7.4. | | | | | | |
|---|---|---|---|---|---|---|---|
| Comp. | C018 | C036 | C037 | C075 | C108 | C136 | C073 |
| Solubility (mg/ml) | 1.5 | 1.8 | 1.5 | 4.1 | 18.1 | 5.5 | >10 |

The high aqueous solubility means that dissolution and hence absorption will be no problem. This will inevitably cause a dramatic reduction of the dose needed making the aminoalkoxy-chalcones very usefull as drug candidates.

Bioavailability

The bioavailability of the aminoalkoxy chalcones are markedly higher than seen for LicA. The compound C043 has a bioavailability of 42% in mice compared with <6% for LicA.

Bioavailabiblity

The bioavailability of the aminoalkoxy chalcones in mice is in generally very high (e.g. $^{42}$% for C043). As the mouse is a very fast metabolizer of the amino chalcones, compared to rat and human (e.g. C130 mice: 77%; rat:. 6%; human: in general lower than rat), the bioavailability in rat and man is expected to be even higher due to limited first pass metabolism.

In vivo Results

Figure 6:
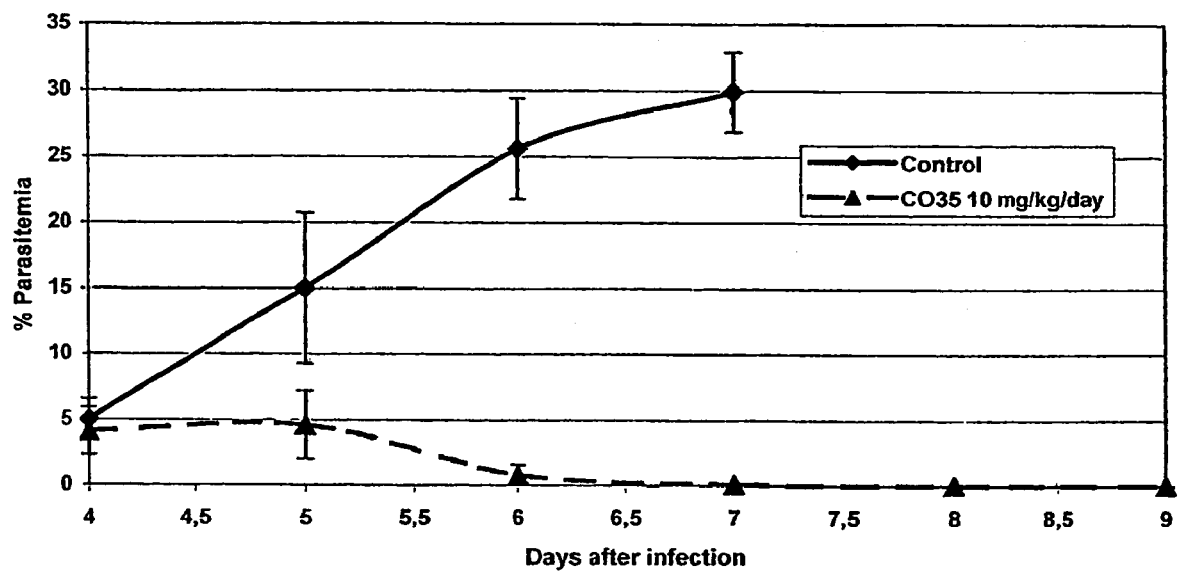
FIG. 6 illustrates an effect curve of C035 in *Plasmodium berghei* K173 infected NMRI female mice following multiple intra venous administrations. As shown at the figure, treatment with C035 causes a significant decrease in the parasitaemia.
Figure 7:
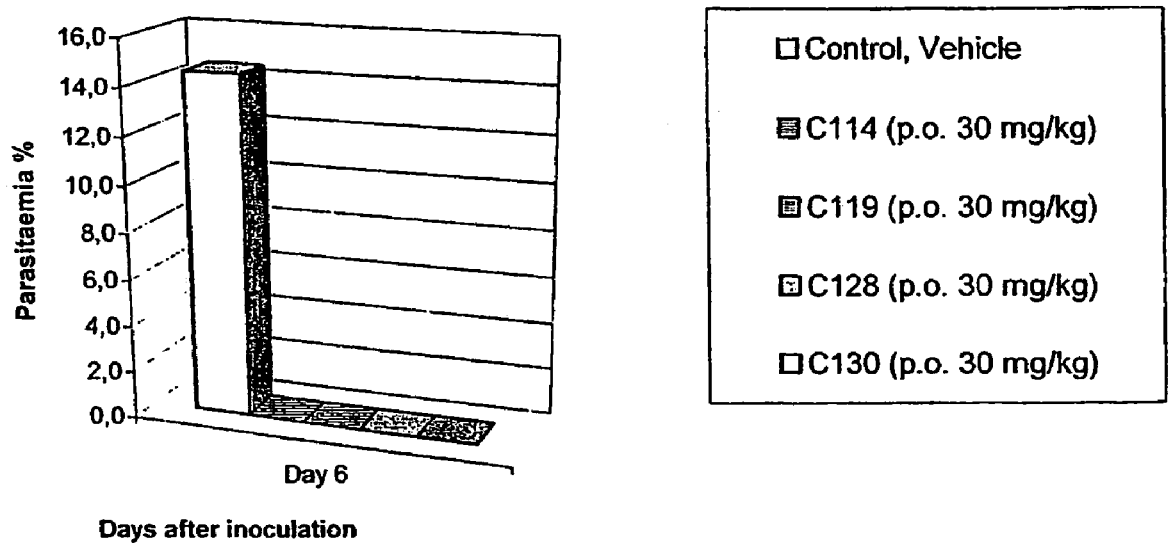
FIG. 7 illustrates an effect curve of C114, C119, C128, C130 in *Plasmodium berghei* K173 infected NMRI female mice following multiple oral administrations. As shown at the figure, treatments with these chalcones inhibit the development of the infection.

A number of amino-chalcones have significant effect in the in vivo models. As illustrated in FIGS. 6 and 7, the compounds cause a significant reduction of parasitaemia in *plasmodium* infected mice, showing the potential of the compounds as drug candidates.

CONCLUSION

The use of chalcones as drug candidates for the treatment of parasitic or bacterial infections has been limited by the low in vivo potency (50mg/kg for LicA) of the compounds and a narrow spectrum of activity.

Several factors contribute to the low in vivo potency: Fast metabolism resulting in short half-lives in vivo; low/no solubility in the intestine and consequently low/no absorption; and medium potency of the compounds against parasites and no activity against bacteria (except for LicA).

The aminoalkoxy-chalcones in this application are expected to fulfill the criteria for a drug candidate. The metabolism is slow, the solubility is High and the compounds are potent against parasites as well as (resistant) Gram positive and Gram negative bacteria.

The invention claimed is:

1. A compound of the formula $$(Y^1)_m-Ar^1(X^1)-C(=O)VAr^2(X^2)-(Y^2)_p$$

and salts thereof, wherein
$Ar^1$ and $Ar^2$ are aryl;
V designates —CH=CH—,
m is 0,
p is 1,
$Y^1$ is not present,
$Y^2$ represents an aminoalkoxy-functional substituent of the formula

—O-Z-N($R^1$)$R^2$, wherein Z is a biradical —$(C(R^H)_2)_n$—, wherein n is 2 and $R^H$ is hydrogen;
$R^1$ and $R^2$ are independently selected from optionally substituted $C_{1-12}$-alkyl;
$X^1$ designates a substituent present 1 time and $X^2$ designates a substituent present 1 time, wherein $X^1$ and $X^2$ are independently selected from the group consisting of optionally substituted $C_{1-12}$-alkyl and optionally substituted aryl.

2. The compound of claim 1, wherein $R^1$ and $R^2$ are independently selected from optionally substituted $C_{1-6}$-alkyl.

3. The compound of claim 1, wherein $X^1$ and $X^2$ are independently selected from the group consisting of optionally substituted $C_{1-6}$-alkyl and optionally substituted aryl.

4. The compound of claim 1, wherein at least one of $Ar^1$ and $Ar^2$ is phenyl.

5. The compound of claim 1, wherein $Ar^1$ and $Ar^2$ are phenyl, $Y^2$ is located in the 2-position of $Ar^2$, and $X^2$ is located in the 4- or 5-position of $Ar^2$.

6. The compound of claim 1,
wherein $R^1$ and $R^2$ are independently selected from $C_{1-6}$-alkyl.

7. The compound of claim 6, wherein $Ar^1$ and $A^2$ are phenyl.

8. The compound of claim 1 selected from
3-[4-(2-Dimethylamino-ethoxy)-2'-trifluoromethyl-biphenyl-3-yl]-1-(2-dimethylaminomethyl-phenyl)-propenone,
and salts thereof.

9. A composition comprising a compound of claim 1 and a pharmaceutically acceptable carrier.

10. A method for treating bacterial infections in a mammal comprising administering to the mammal a compound of claim 1.

11. A method for treatment of infections associated with protozoa in a mammal comprising administering to the mammal a compound of claim 1.

* * * * *